United States Patent
Ogawa et al.

(10) Patent No.: US 10,385,045 B2
(45) Date of Patent: Aug. 20, 2019

(54) COMPOUND HAVING EP2 AGONIST ACTIVITY

(71) Applicant: ONO PHARMACEUTICAL CO., LTD., Osaka (JP)

(72) Inventors: Seiji Ogawa, Osaka (JP); Toshihide Watanabe, Osaka (JP); Isamu Sugimoto, Osaka (JP); Kousuke Tani, Osaka (JP); Kazumi Moriyuki, Osaka (JP); Yoshikazu Goto, Osaka (JP); Shinsaku Yamane, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/746,617

(22) PCT Filed: Jul. 22, 2016

(86) PCT No.: PCT/JP2016/071611
§ 371 (c)(1),
(2) Date: Jan. 22, 2018

(87) PCT Pub. No.: WO2017/014315
PCT Pub. Date: Jan. 26, 2017

(65) Prior Publication Data
US 2018/0215747 A1 Aug. 2, 2018

(30) Foreign Application Priority Data

Jul. 23, 2015 (JP) .................. 2015-145776

(51) Int. Cl.
| | | |
|---|---|---|
| *C07D 417/04* | (2006.01) | |
| *C07D 407/04* | (2006.01) | |
| *C07D 409/04* | (2006.01) | |
| *C07D 417/14* | (2006.01) | |
| *A61K 31/352* | (2006.01) | |
| *A61K 31/381* | (2006.01) | |
| *A61K 31/427* | (2006.01) | |
| *A61K 31/428* | (2006.01) | |
| *A61P 27/06* | (2006.01) | |
| *A61P 27/10* | (2006.01) | |

(Continued)

(52) U.S. Cl.
CPC .......... *C07D 417/04* (2013.01); *A61K 31/352* (2013.01); *A61K 31/381* (2013.01); *A61K 31/427* (2013.01); *A61K 31/428* (2013.01); *A61P 27/02* (2018.01); *A61P 27/06* (2018.01); *A61P 27/10* (2018.01); *A61P 27/12* (2018.01); *C07D 407/04* (2013.01); *C07D 409/04* (2013.01); *C07D 417/14* (2013.01)

(58) Field of Classification Search
CPC .. A61K 31/352; A61K 31/381; A61K 31/427; A61K 31/428; C07D 407/04; C07D 409/04; C07D 417/04; C07D 417/14
See application file for complete search history.

(56) References Cited

U.S. PATENT DOCUMENTS

| | | | | |
|---|---|---|---|---|
| 4,281,113 A | * | 7/1981 | Axen | .................... C07C 405/00 549/396 |
| 4,312,810 A | | 1/1982 | Axen et al. | |
| 4,490,537 A | | 12/1984 | Johnson | |

(Continued)

FOREIGN PATENT DOCUMENTS

| | | |
|---|---|---|
| EP | 0193260 A2 | 9/1986 |
| JP | 55-89261 A | 7/1980 |

(Continued)

OTHER PUBLICATIONS

Wolff, Manfred E., Burger's Medicinal Chemistry and Drug Discovery, Fifth Ed., vol. 1: Principles and Practice, John Wiley & Sons, 1995, 975. (Year: 1995).*

(Continued)

*Primary Examiner* — Erich A Leeser
(74) *Attorney, Agent, or Firm* — Sughrue Mion, PLLC

(57) ABSTRACT

Provided is an EP2 agonist having excellent safety. A compound represented by general formula (I)

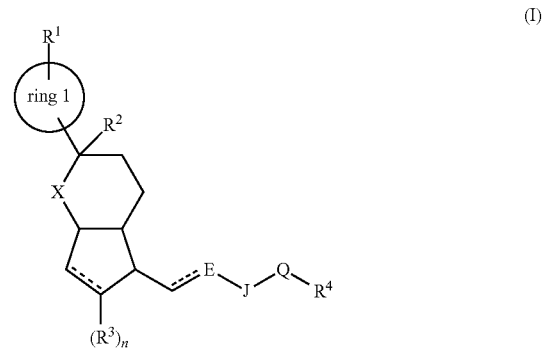

(wherein all symbols are as defined in the description), a salt or N-oxide of the compound, or a solvate or prodrug of the compound or the salt or N-oxide has an EP2 agonist activity and is highly safe, and is therefore useful as a medicine, particularly a therapeutic agent for diseases associated with EP2 receptors, such as immune diseases, allergic diseases, neuronal death, dysmenorrhea, premature birth, miscarriage, baldness, ocular diseases, erectile dysfunction, arthritis, lung injury, pulmonary fibrosis, pulmonary emphysema, bronchitis, chronic obstructive pulmonary disease, bone diseases and cartilage injury.

11 Claims, No Drawings

(51) Int. Cl.
    *A61P 27/12* (2006.01)
    *A61P 27/02* (2006.01)

(56) References Cited

U.S. PATENT DOCUMENTS

| | | |
|---|---|---|
| 4,740,523 A | 4/1988 | Galambos et al. |
| 5,877,211 A | 3/1999 | Woodward |
| 6,262,293 B1 | 7/2001 | Tani et al. |
| 2002/0044953 A1 | 4/2002 | Michelet et al. |
| 2008/0015219 A1 | 1/2008 | Old et al. |
| 2008/0015231 A1 | 1/2008 | Old et al. |
| 2008/0119538 A1 | 5/2008 | Old et al. |
| 2012/0122964 A1 | 5/2012 | Kambe et al. |
| 2013/0310438 A1 | 11/2013 | Maruyama et al. |
| 2017/0015657 A1 | 1/2017 | Ogawa et al. |

FOREIGN PATENT DOCUMENTS

| | | |
|---|---|---|
| JP | 61-218588 A | 9/1986 |
| JP | 2009-541340 A | 11/2009 |
| JP | 2009-543792 A | 12/2009 |
| JP | 2009-543794 A | 12/2009 |
| JP | 2009-543795 A | 12/2009 |
| JP | 2010-516779 A | 5/2010 |
| JP | 2010-532379 A | 10/2010 |
| WO | 99/33794 A1 | 7/1999 |
| WO | 2007/149829 A2 | 12/2007 |
| WO | 2007/149829 A3 | 12/2007 |
| WO | 2008/091860 A1 | 7/2008 |
| WO | 2009/006370 A1 | 1/2009 |
| WO | 2011/013651 A1 | 2/2011 |
| WO | 2011/162562 A2 | 12/2011 |
| WO | 2012/102355 A1 | 8/2012 |
| WO | 2015/129782 A1 | 9/2015 |
| WO | 2017/014315 A2 | 1/2017 |

OTHER PUBLICATIONS

Banker, Gilbert S. et al., Modem Pharmaceutics, Marcel Dekker, New York, 1996. (Year: 1996).*
West, Anthony R., Solid State Chemistry and Its Applications, Wiley, New York, 1988, 358. (Year: 1988).*
Nataraj C.et al., "Receptors for prostaglandin E2 that regulate cellular immune responses in the mouse", The Journal of Clinical Investigation, Oct. 2001;108(8):1229-35.
Sheller, J.R. et al., "EP2 receptor mediates bronchodilation by PGE2 in mice", J Appl Physiol., Jun. 2000;88(6):2214-18.
Andrade Da Costa BL et al, "The localization of PGE2 receptor subtypes in rat retinal cultures and the neuroprotective effect of the EP2 agonist butaprost", Neurochem Int. Sep. 2009;55(4):199-207.
Hillock, C. J. et al, "Inhibitory prostanoid EP receptors in human non-pregnant myometrium", European Journal of Pharmacology 378, 1999.99-108.
Senior, J. et al, "In vitro characterization of prostanoid EP-receptors in the non-pregnant human myometrium", Br J Pharmacol. Mar. 1991;102(3):747-53.
Woodward,D.F. et al, "Molecular Characterization and Ocular Hypotensive Properties of the Prostanoid EP2 Receptor", J Ocul Pharmacol Ther. 1995 Fall;11(3):447-54.
Kurihara, Y. et al, "Up-regulation of prostaglandin E receptor EP2 and EP4 subtypes in rat synovial tissues with adjuvant arthritis", Clin Exp Immunol 2001; 123:323-330.
Armstrong, R. A., Investigation of the inhibitory effects of PGE2 and selective EP agonists on chemotaxis of human neutrophils, Br J Pharmacol. Dec. 1995;116(7):2903-08.
Talpain, E. et al., "Characterization of the PGE receptor subtype mediating inhibition of superoxide production in human neutrophils", Br J Pharmacol. Apr. 1995;114(7):1459-65.
Keerthisingam, C. B. et al, "Cyclooxygenase-2 Deficiency Results in a Loss of the Anti-Proliferative Response to Transforming Growth Factor-ß in Human Fibrotic Lung Fibroblasts and Promotes Bleomycin-Induced Pulmonary Fibrosis in Mice", Am J Pathol. Apr. 2001;158(4):1411-22.
Tsuji, T. et al, "Promotion of adipogenesis by an EP2 receptor agonist via stimulation of angiogenesis in pulmonary emphysema", Prostaglandins & Other Lipid Mediators, Aug. 2014;112:9-15.
Fennekohl, A. et al, "Contribution of the two Gs-coupled PGE2-receptors EP2-receptor and EP4-receptor to the inhibition by PGE2 of the LPS-induced TNFa-formation in Kupffer cells from EP2-or EP4-receptor-deficient mice. Pivotal role for the EP4-receptor in wild type Kupffer cells", Journal of Hepatology 36, 3 , Mar. 2002, 328-334.
Hartner, A. et al, "Upregulation of cyclooxygenase-1 and the PGE2 receptor EP2 in rat and human mesangioproliferative glomerulonephritis", Inflamm Res. Jul. 2000,49(7),345-54.
Breyer, M. D. et al, "Prostaglandin E receptors and the kidney", Am J Physiol Renal Physiol. Jul. 2000;279(1):F12-23.
Breyer, M. D. et al, "Functional and Molecular Aspects of Renal Prostaglandin Receptors", J Am Soc Nephrol. Jan. 1996;7(1):8-17.
Kennedy, C. R.J. et al, "Salt-sensitive hypertension and reduced fertility in mice lacking the prostaglandin EP2 receptor", Nat Med Feb. 1999;5(2):217-220.
Németh, K. et al, "Bone marrow stromal cells attenuate sepsis via prostaglandin E2—dependent reprogramming of host macrophages to increase their interleukin-10 production", Nat Med Jan. 2009;15(1):42-49.
Ikegami, R. et al, "The Expression of Prostaglandin E Receptors EP2 and EP4 and Their Different Regulation by Lipopolysaccharide in C3H/HeN Peritoneal Macrophages", J Immunol. Apr. 1, 2001;166(7):4689-96.
Suzawa, T. et al, "The Role of Prostaglandin E Receptor Subtypes (EP1, EP2, EP3, and EP4) in Bone Resorption: An Analysis Using Specific Agonists for the Respective EPs", Endocrinology. Apr. 2000,141(4),1554-59.
Otsuka, S. et al, "PGE2 signal via EP2 receptors evoked by a selective agonist enhances regeneration of injured articular cartilage", Osteoarthritis and Cartilage Apr. 2009;17(4):529-538.
Thota Ganesh: "Prostanoid Receptor EP2 as a Therapeutic Target"; Journal of Medicinal Chemistry, 2014, 57, 4454-4465.
Birrell et al: "At last, a truly selective EP2 receptor antagonist"; British Journal of Pharmacology 2011, 164, 1845-1846.
Prasanna et al: "Effect of PF-04217329 a prodrug of a selective prostaglandin EP2 agonist on intraocular pressure in preclinical models of glaucoma"; Experimental Eye Research 2011, 93, 256-264.
Schacar et al: "A Phase 2, Randomized, Dose-Response Trial of Taprenepag Isopropyl (PF-04217329) Versus Latanoprost 0.005% in Open-Angle Glaucoma and Ocular Hypertension"; Current Eye Research, 2011, 36, 809-817.
International Search Report dated Apr. 14, 2015 issued by International Searching Authority in Related International Application No. PCT/JP2015/055523 (PCT/ISA/210).
Written Opinion dated Apr. 14, 2015 issued by International Searching Authority in related International Application No. PCT/JP2015/055523 (PCT/ISA/237).
Ogawa S. et al.: "Discovery of G Protein-Biased EP2 Receptor Agonists", ACS Medicinal Chemistry Letters, Jan. 4, 2016, vol. 7, pp. 306-311, (6 pages total).
Ogawa S. et al.: "Structural optimization and structure—functional selectivity relationship studies of G protein-biased EP2 receptor agonists", Bioorganic & Medicinal Chemistry Letters, Mar. 31, 2016, vol. 26, pp. 2446-2449, (4 pages total).
International Search Report dated Sep. 27, 2016, by the International Searching Authority in counterpart International Application No. PCT/JP2016/071611 (PCT/ISA/210).
Written Opinion dated Sep. 27, 2016, by the International Searching Authority in counterpart International Application No. PCT/JP2016/071611 (PCT/ISA/237).

* cited by examiner

COMPOUND HAVING EP2 AGONIST ACTIVITY

TECHNICAL FIELD

The present invention relates to a compound represented by general formula

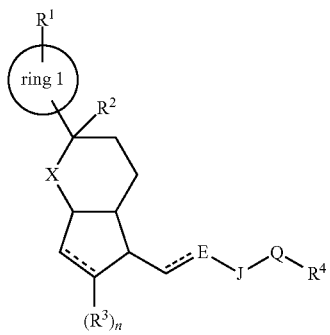

(wherein all symbols are as defined below), a salt or N-oxide of the compound, or a solvate or prodrug of the compound or the salt or N-oxide (hereinbelow, may be sometimes abbreviated as "the compound according to the present invention").

BACKGROUND ART

Prostaglandin $E_2$ (hereinbelow, abbreviated as "$PGE_2$") is known as a metabolite in the arachidonate cascade, and is also known to have a cell protection effect, an oxytocic effect, an algogenic effect, an effect of promoting the peristaltic movement of the digestive tract, an awakening effect, a gastric acid secretion inhibiting effect, a blood pressure lowering effect, a diuretic effect and the like.

$PGE_2$ receptors are classified into four subtypes having different roles from one another, i.e., EP1, EP2, EP3, EP4. Among these subtypes, an EP2 receptor is considered to be involved in the inhibition of the production of TNF-α and the enhancement of the production of IL-10, and therefore an EP2 agonist is considered to be useful for the prevention and/or treatment of immune diseases, allergic diseases, neuronal death, dysmenorrhea, premature birth, miscarriage, baldness, ocular diseases, erectile dysfunction, arthritis, lung injury, pulmonary fibrosis, pulmonary emphysema, bronchitis, chronic obstructive pulmonary disease, liver injury, acute hepatitis, cirrhosis, shock, nephritis, renal failure, cardiovascular diseases, systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases, cartilage injury and others.

Meanwhile, as compounds which have analogous structures to the structure of the compound according to the present invention, selective FP agonists are disclosed in, for example, International Publication No. 2011/013651 pamphlet and International Publication No. 2012/102355 pamphlet, and prostacyclin derivatives are disclosed in, for example, Japanese Patent Laying-Open No. S61-218588 and Japanese Patent Laying-Open No. S55-89261.

However, in these prior art documents, there is found no statement or suggestion about EP2 agonists.

CITATIONS LIST

Patent Literature 1: International Publication No. 2011/013651 pamphlet
Patent Literature 2: International Publication No. 2012/102355 pamphlet
Patent Literature 3: Japanese Patent Laying-Open No. S61-218588
Patent Literature 4: Japanese Patent Laying-Open No. S55-89261

SUMMARY OF INVENTION

Technical Problems

An object of the present invention is to provide an excellent EP2 agonist in a safe manner.

Solutions to Problems

The present inventors have made extensive and intensive studies, and as a result, found that a compound represented by general formula (I) can solve the problems. The present inventors have made further studies, and consequently have completed the present invention.

That is, the present invention relates to the followings.
1. A compound represented by general formula (I):

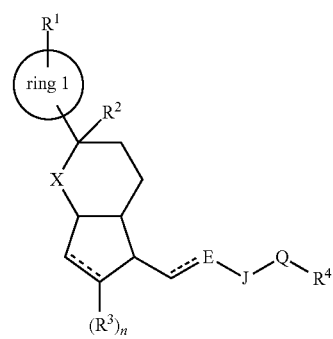

(wherein ring 1 represents a 5- or 6-membered monocyclic aromatic ring;
$R^1$ represents —$(CH_2)_p$—COOH, —$(CH_2)_q$—COOR$^{11}$, —$(CH_2)_r$, —OR$^{12}$, —CH$_2$NR$^{13}$R$^{14}$ or —CONR$^{13}$R$^{14}$;
p represents an integer of 0 to 4;
q represents an integer of 0 to 4;
r represents an integer of 1 to 4;
s represents an integer of 1 to 4;
$R^{11}$ represents a C1-4 alkyl group;
$R^{12}$ represents a C1-4 alkyl group or a C1-4 acyl group;
$R^{13}$ represents a hydrogen atom or a C1-4 alkyl group and
$R^{14}$ represents a hydrogen atom, a C1-4 alkyl group, a C1-4 acyl group, or a $R^{15}$O(C=O)—C1-4 alkylene group, or
$R^{13}$, $R^{14}$ and a nitrogen atom to which $R^{13}$ and $R^{14}$ are bound together represent a saturated 5- to 8-membered cyclic amine group;
$R^{15}$ represents a hydrogen atom or a C1-4 alkyl group;
X represents —O—, —S—, —SO—, —SO$_2$—, or —NR$^{16}$—;
$R^{16}$ represents a hydrogen atom, a C1-4 alkyl group, or a C1-4 acyl group;
$R^2$ represents a hydrogen atom, or a C1-4 alkyl group;
$R^3$ represents a hydrogen atom, a halogen atom, or —OR$^{31}$;

$R^{31}$ represents a hydrogen atom, a C1-4 alkyl group, or a C1-4 acyl group;
n represents an integer of 1 or 2;
$R^3$'s may be the same as or different from each other when n represents 2;
E represents —O—, —S—, —SO—, —SO$_2$—, —CH$_2$—, =CH—, or —NR$^{17}$—;
$R^{17}$ represents a hydrogen atom, a C1-4 alkyl group, or a C1-4 acyl group;
J represents —(CR$^7$R$^8$)$_m$—;
m represents an integer of 0 to 4;
$R^7$ and $R^8$ independently represent a hydrogen atom, a halogen atom, a hydroxy group or a C1-4 alkyl group which may be substituted by a halogen atom, wherein two or more $R^7$'s and $R^8$'s may be the same as or different from each other, or $R^7$ and $R^8$ on the same carbon atom and the carbon atom to which $R^7$ and $R^8$ are bound may together form a C3-6 saturated carbon ring;
Q represents a bond, —CH$_2$—, —O—, —O—CH$_2$—, —S—, —SO—, —SO$_2$—, or —NR$^{18}$—;
$R^{18}$ represents a hydrogen atom, a C1-4 alkyl group, or a C1-4 acyl group;
$R^4$ represents a C1-4 alkyl group, a C2-4 alkenyl group, a C2-4 alkynyl group, or a 3- to 15-membered ring, wherein the 3- to 15-membered ring may be substituted by 0 to 5$R^5$'s;
$R^5$ represents (1) a C1-8 alkyl group, (2) a C2-8 alkenyl group, (3) a C2-8 alkynyl group, (4) a C3-8 cycloalkyl group, (5) a C1-8 alkoxy group, (6) a C3-8 cycloalkyloxy group, (7) a C1-8 acyl group, (8) a C1-8 acyloxy group, (9) a C1-8 alkylthio group, (10) a C3-8 cycloalkylthio group, (11) a C1-8 alkylsulfinyl group, (12) a C3-8 cycloalkylsulfinyl group, (13) a C1-8 alkylsulfonyl group, (14) a C3-8 cycloalkylsulfonyl group, (15) a C1-8 alkoxycarbonyl group, (16) a 5- or 6-membered cyclic group, (17) a (5- or 6-membered cyclic group)-C1-4 alkyl group, (18) a (5- or 6-membered cyclic group)-C1-4 alkoxy group, (19) a (5- or 6-membered cyclic group)-C1-4 acyl group, (20) a halogen atom, (21) a hydroxy group, (22) a nitro group, (23) a cyano group, (24) —NR$^{51}$R$^{52}$, (25) —CONR$^{53}$R$^{54}$, or (26) —SO$_2$NR$^{55}$R$^{56}$;
$R^{51}$, $R^{52}$, $R^{53}$, $R^{54}$, $R^{55}$ and $R^{56}$ independently represent a hydrogen atom, a C1-8 alkyl group, a C1-8 acyl group, or a C1-8 alkylsulfonyl group; $R^5$'s may be the same as or different from each other when the 3- to 15-membered ring is substituted by multiple $R^5$'s, wherein each of the groups (1) to (19) for $R^5$ may be substituted by 1 to 3 $R^6$'s;
$R^6$ represents a C1-4 alkyl group, a C1-4 alkoxy group, a C1-4 acyl group, a C3-8 cycloalkyl group, OH, —NR$^{61}$R$^{62}$, or a halogen atom, wherein $R^6$'s may be the same as or different from each other when each of the groups (1) to (19) is substituted by multiple $R^6$'s;
$R^{61}$ and $R^{62}$ independently represent a hydrogen atom or a C1-4 alkyl group; and the following bond
=====
independently represents a single bond or a double bond), a salt or N-oxide of the compound, or a solvate or prodrug of the compound or the salt or N-oxide.

2. The compound according to item 1, a salt or N-oxide of the compound, or a solvate or prodrug of the compound or the salt or N-oxide, wherein Q represents —CH$_2$—, —O—, —O—CH$_2$—, —S—, —SO—, —SO$_2$— or —NR$^{18}$—.

3. The compound according to item 1, a salt or N-oxide of the compound, or a solvate or prodrug of the compound or the salt or N-oxide, wherein Q represents a bond and at least one of $R^3$'s represents a halogen atom.

4. The compound according to any one of items 1 to 3, a salt or N-oxide of the compound, or a solvate or prodrug of the compound or the salt or N-oxide, wherein E represents —CH$_2$— or =CH—.

5. The compound according to any one of items 1 to 4, a salt or N-oxide of the compound, or a solvate or prodrug of the compound or the salt or N-oxide, wherein ring 1 represents a 5-membered monocyclic aromatic heterocyclic ring.

6. The compound according to any one of items 1 to 5, a salt or N-oxide of the compound, or a solvate or prodrug of the compound or the salt or N-oxide, wherein X represents —O— or —S—.

7. A compound represented by general formula (I-1):

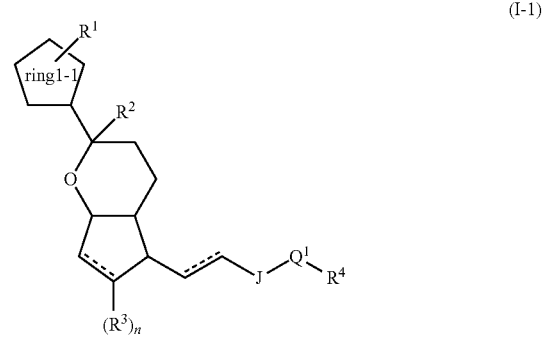

(wherein ring 1-1 represents a 5-membered monocyclic aromatic heterocyclic ring; $Q^1$ represents —CH$_2$—, —O—, —O—CH$_2$—, —S—, —SO—, —SO$_2$—, or —NR$^{18}$—; and other symbols are as defined in claim 1), a salt or N-oxide of the compound, or a solvate or prodrug of the compound or the salt or N-oxide.

8. The compound according to item 7, a salt or N-oxide of the compound, or a solvate or prodrug of the compound or the salt or N-oxide, wherein ring 1-1 represents an oxazole ring, a thiazole ring, a furan ring, or a thiophene ring.

9. The compound according to item 1 or 2, a salt or N-oxide of the compound, or a solvate or prodrug of the compound or the salt or N-oxide, wherein the compound is selected from:

(1)
2-{(2R,4aR,5R,6R,7aS)-5-[(1E)-3-(3-fluorophenoxy)-1-propen-1-yl]-6-hydroxyoctahydrocyclopenta[b]pyran-2-yl}-1,3-thiazole-4-carboxylic acid;

(2)
2-{(2R,4aR,5R,6R,7aS)-6-hydroxy-5-[(1E)-5-(4-methoxyphenoxy)-1-penten-1-yl]octahydrocyclopenta[b]pyran-2-yl}-1,3-thiazole-4-carboxylic acid;

(3)
2-{(2R,4aR,5R,6R,7aS)-6-hydroxy-5-[(1E)-4-phenoxy-1-buten-1-yl]octahydrocyclopenta[b]pyran-2-yl}-1,3-thiazole-4-carboxylic acid;

(4)
2-{(2R,4aR,5R,6R,7aS)-6-hydroxy-5-[(1E)-3-phenoxy-1-propen-1-yl]octahydrocyclopenta[b]pyran-2-yl}-1,3-thiazole-4-carboxylic acid;

(5)
2-{(2R,4aR,5R,6R,7aS)-6-hydroxy-5-[(1E)-5-phenoxy-1-penten-1-yl]octahydrocyclopenta[b]pyran-2-yl}-1,3-thiazole-4-carboxylic acid;

(6) 2-{(2R,4aR,5R,6R,7aS)-5-[(1E)-3-(2-fluorophenoxy)-1-propen-1-yl]-6-hydroxyoctahydrocyclopenta[b]pyran-2-yl}-1,3-thiazole-4-carboxylic acid;

(7) 2-{(2R,4aR,5R,6R,7aS)-5-[(1E)-3-(4-fluorophenoxy)-1-propen-1-yl]-6-hydroxyoctahydrocyclopenta[b]pyran-2-yl}-1,3-thiazole-4-carboxylic acid;

(8) 2-{(2R,4aR,5R,6R,7aS)-6-hydroxy-5-[(1E)-3-(2-methylphenoxy)-1-propen-1-yl]octahydrocyclopenta[b]pyran-2-yl}-1,3-thiazole-4-carboxylic acid;

(9) 2-{(2R,4aR,5R,6R,7aS)-6-hydroxy-5-[(1E)-3-(3-methylphenoxy)-1-propen-1-yl]octahydrocyclopenta[b]pyran-2-yl}-1,3-thiazole-4-carboxylic acid;

(10) 2-{(2R,4aR,5R,6R,7aS)-6-hydroxy-5-[(1E)-3-(4-methylphenoxy)-1-propen-1-yl]octahydrocyclopenta[b]pyran-2-yl}-1,3-thiazole-4-carboxylic acid;

(11) 2-{(2R,4aR,5R,6R,7aS)-5-[(1E)-3-(2-chlorophenoxy)-1-propen-1-yl]-6-hydroxyoctahydrocyclopenta[b]pyran-2-yl}-1,3-thiazole-4-carboxylic acid;

(12) 2-{(2R,4aR,5R,6R,7aS)-5-[(1E)-3-(3-chlorophenoxy)-1-propen-1-yl]-6-hydroxyoctahydrocyclopenta[b]pyran-2-yl}-1,3-thiazole-4-carboxylic acid;

(13) 2-{(2R,4aR,5R,6R,7aS)-5-[(1E)-3-(4-chlorophenoxy)-1-propen-1-yl]-6-hydroxyoctahydrocyclopenta[b]pyran-2-yl}-1,3-thiazole-4-carboxylic acid;

(14) 2-[(2R,4aR,5R,6R,7aS)-6-hydroxy-5-{(1E)-3-[2-(trifluoromethoxy)phenoxy]-1-propen-1-yl}octahydrocyclopenta[b]pyran-2-yl]-1,3-thiazole-4-carboxylic acid;

(15) 2-[(2R,4aR,5R,6R,7aS)-6-hydroxy-5-{(1E)-3-[3-(trifluoromethoxy)phenoxy]-1-propen-1-yl}octahydrocyclopenta[b]pyran-2-yl]-1,3-thiazole-4-carboxylic acid;

(16) 2-[(2R,4aR,5R,6R,7aS)-6-hydroxy-5-{(1E)-3-[4-(trifluoromethoxy)phenoxy]-1-propen-1-yl}octahydrocyclopenta[b]pyran-2-yl]-1,3-thiazole-4-carboxylic acid;

(17) 2-[(2R,4aR,5R,6R,7aS)-6-hydroxy-5-{(1E)-3-[2-(trifluoromethyl)phenoxy]-1-propen-1-yl}octahydrocyclopenta[b]pyran-2-yl]-1,3-thiazole-4-carboxylic acid;

(18) 2-[(2R,4aR,5R,6R,7aS)-6-hydroxy-5-{(1E)-3-[3-(trifluoromethyl)phenoxy]-1-propen-1-yl}octahydrocyclopenta[b]pyran-2-yl]-1,3-thiazole-4-carboxylic acid;

(19) 2-[(2R,4aR,5R,6R,7aS)-6-hydroxy-5-{(1E)-3-[4-(trifluoromethyl)phenoxy]-1-propen-1-yl}octahydrocyclopenta[b]pyran-2-yl]-1,3-thiazole-4-carboxylic acid;

(20) 2-{(2R,4aR,5R,6R,7aS)-6-hydroxy-5-[(1E)-3-(2-methoxyphenoxy)-1-propen-1-yl]octahydrocyclopenta[b]pyran-2-yl}-1,3-thiazole-4-carboxylic acid;

(21) 2-{(2R,4aR,5R,6R,7aS)-6-hydroxy-5-[(1E)-3-(3-methoxyphenoxy)-1-propen-1-yl]octahydrocyclopenta[b]pyran-2-yl}-1,3-thiazole-4-carboxylic acid;

(22) 2-{(2R,4aR,5R,6R,7aS)-6-hydroxy-5-[(1E)-3-(4-methoxyphenoxy)-1-propen-1-yl]octahydrocyclopenta[b]pyran-2-yl}-1,3-thiazole-4-carboxylic acid;

(23) 2-[(2R,4aR,5R,6R,7aS)-6-hydroxy-5-{(1E)-5-[4-(trifluoromethoxy)phenoxy]-1-penten-1-yl}octahydrocyclopenta[b]pyran-2-yl]-1,3-thiazole-4-carboxylic acid;

(24) 2-{(2R,4aR,5R,6R,7aS)-5-[(1E)-5-(4-chloro-3-fluorophenoxy)-1-penten-1-yl]-6-hydroxyoctahydrocyclopenta[b]pyran-2-yl}-1,3-thiazole-4-carboxylic acid;

(25) (2R,4aR,5R,6R,7aS)-2-[4-(hydroxymethyl)-1,3-thiazol-2-yl]-5-[(1E)-5-(4-methoxyphenoxy)-1-penten-1-yl]octahydrocyclopenta[b]pyran-6-ol;

(26) isopropyl 2-{(2R,4aR,5R,6R,7aS)-6-hydroxy-5-[(1E)-5-(4-methoxyphenoxy)-1-penten-1-yl]octahydrocyclopenta[b]pyran-2-yl}-1,3-thiazole-4-carboxylate;

(27) isopropyl 2-{(2R,4aR,5R,6R,7aS)-6-hydroxy-5-[(1E)-4-phenoxy-1-buten-1-yl]octahydrocyclopenta[b]pyran-2-yl}-1,3-thiazole-4-carboxylate;

(28) isopropyl 2-[(2R,4aR,5R,6R,7aS)-6-hydroxy-5-{(1E)-3-[2-(trifluoromethyl)phenoxy]-1-propen-1-yl}octahydrocyclopenta[b]pyran-2-yl]-1,3-thiazole-4-carboxylate;

(29) 2-{(2R,4aR,5R,6R,7aS)-5-[(1E)-3-(benzyloxy)-1-propen-1-yl]-6-hydroxyoctahydrocyclopenta[b]pyran-2-yl}-1,3-thiazole-4-carboxylic acid;

(30) 2-{(2R,4aR,5R,6R,7aS)-5-[3-(benzyloxy)propyl]-6-hydroxyoctahydrocyclopenta[b]pyran-2-yl}-1,3-thiazole-4-carboxylic acid;

(31) 2-[(2R,4aR,5R,6R,7aS)-6-hydroxy-5-(3-phenoxypropyl)octahydrocyclopenta[b]pyran-2-yl]-1,3-thiazole-4-carboxylic acid;

(32) 2-[(2R,4aR,5R,6R,7aS)-6-hydroxy-5-(5-phenoxypentyl)octahydrocyclopenta[b]pyran-2-yl]-1,3-thiazole-4-carboxylic acid;

(33) 2-[(2R,4aR,5R,6R,7aS)-6-hydroxy-5-(4-phenoxybutyl)octahydrocyclopenta[b]pyran-2-yl]-1,3-thiazole-4-carboxylic acid;

(34) 2-{(2R,4aR,5R,6R,7aS)-5-[(1E)-3,3-difluoro-1-octen-1-yl]-6-hydroxyoctahydrocyclopenta[b]pyran-2-yl}-1,3-thiazole-4-carboxylic acid;

(35) 2-{(2R,4aR,5R,6R,7aS)-5-[(1E)-4,4-difluoro-3-hydroxy-1-octen-1-yl]-6-hydroxyoctahydrocyclopenta[b]pyran-2-yl}-1,3-thiazole-4-carboxylic acid;

(36) 2-{(2R,4aR,5R,6R,7aS)-5-[(1E)-5-(4-cyanophenyl)-3-hydroxy-1-penten-1-yl]-6-hydroxyoctahydrocyclopenta[b]pyran-2-yl}-1,3-thiazole-4-carboxylic acid;

(37) 2-{(2R,4aR,5R,6R,7aS)-6-hydroxy-5-[(1E)-3-hydroxy-1-octen-1-yl]octahydrocyclopenta[b]pyran-2-yl}-1,3-thiazole-4-carboxylic acid;

(38)
2-{(2R,4aR,5R,6R,7aS)-5-[(1E)-5-cyclopentyl-3-hydroxy-1-penten-1-yl]-6-hydroxyoctahydrocyclopenta[b]pyran-2-yl}-1,3-thiazole-4-carboxylic acid;

(39)
2-{(2R,4aR,5R,6R,7aS)-6-hydroxy-5-[(1E)-3-hydroxy-5-(2-naphthyl)-1-penten-1-yl]octahydrocyclopenta[b]pyran-2-yl}-1,3-thiazole-4-carboxylic acid;

(40)
2-{(2R,4aR,5R,6R,7aS)-6-hydroxy-5-[(1E)-3-hydroxy-1-decen-1-yl]octahydrocyclopenta[b]pyran-2-yl}-1,3-thiazole-4-carboxylic acid;

(41)
2-{(2R,4aR,5R,6R,7aS)-6-hydroxy-5-[(1E)-3-hydroxy-4-phenyl-1-buten-1-yl]octahydrocyclopenta[b]pyran-2-yl}-1,3-thiazole-4-carboxylic acid;

(42)
2-{(2R,4aR,5R,6R,7aS)-6-hydroxy-5-[(1E)-4-hydroxy-1-octen-1-yl]octahydrocyclopenta[b]pyran-2-yl}-1,3-thiazole-4-carboxylic acid;

(43)
2-{(2R,4aR,5R,6R,7aS)-5-[(1E,4S)-4-(1-ethylcyclobutyl)-4-hydroxy-1-buten-1-yl]-6-hydroxyoctahydrocyclopenta[b]pyran-2-yl}-1,3-thiazole-4-carboxylic acid;

(44)
2-{(2R,4aR,5R,6R,7aS)-6-hydroxy-5-[(1E,3S)-3-hydroxy-1-octen-1-yl]octahydrocyclopenta[b]pyran-2-yl}-1,3-thiazole-4-carboxylic acid;

(45)
2-[(2R,4aR,5R,6R,7aS)-6-hydroxy-5-(2-phenoxyethyl)octahydrocyclopenta[b]pyran-2-yl]-1,3-thiazole-4-carboxylic acid;

(46)
2-{(2R,4aR,5R,6R,7aS)-6-hydroxy-5-[2-(3-methylphenoxy)ethyl]octahydrocyclopenta[b]pyran-2-yl}-1,3-thiazole-4-carboxylic acid;

(47)
2-{(2R,4aR,5R,6R,7aS)-6-hydroxy-5-[2-(2-methylphenoxy)ethyl]octahydrocyclopenta[b]pyran-2-yl}-1,3-thiazole-4-carboxylic acid;

(48)
2-{(2R,4aR,5R,6R,7aS)-6-hydroxy-5-[2-(4-methylphenoxy)ethyl]octahydrocyclopenta[b]pyran-2-yl}-1,3-thiazole-4-carboxylic acid;

(49)
2-{(2R,4aR,5R,6R,7aS)-5-[2-(2-fluorophenoxy)ethyl]-6-hydroxyoctahydrocyclopenta[b]pyran-2-yl}-1,3-thiazole-4-carboxylic acid;

(50)
2-{(2R,4aR,5R,6R,7aS)-5-[2-(3-fluorophenoxy)ethyl]-6-hydroxyoctahydrocyclopenta[b]pyran-2-yl}-1,3-thiazole-4-carboxylic acid;

(51)
2-{(2R,4aR,5R,6R,7aS)-5-[2-(4-fluorophenoxy)ethyl]-6-hydroxyoctahydrocyclopenta[b]pyran-2-yl}-1,3-thiazole-4-carboxylic acid;

(52)
2-{(2R,4aR,5R,6R,7aS)-5-[2-(2-chlorophenoxy)ethyl]-6-hydroxyoctahydrocyclopenta[b]pyran-2-yl}-1,3-thiazole-4-carboxylic acid;

(53)
2-{(2R,4aR,5R,6R,7aS)-5-[2-(3-chlorophenoxy)ethyl]-6-hydroxyoctahydrocyclopenta[b]pyran-2-yl}-1,3-thiazole-4-carboxylic acid;

(54)
2-{(2R,4aR,5R,6R,7aS)-5-[2-(4-chlorophenoxy)ethyl]-6-hydroxyoctahydrocyclopenta[b]pyran-2-yl}-1,3-thiazole-4-carboxylic acid;

(55)
2-[(2R,4aR,5R,6R,7aS)-6-hydroxy-5-{2-[2-(trifluoromethoxy)phenoxy]ethyl}octahydrocyclopenta[b]pyran-2-yl]-1,3-thiazole-4-carboxylic acid;

(56)
2-[(2R,4aR,5R,6R,7aS)-6-hydroxy-5-{2-[3-(trifluoromethoxy)phenoxy]ethyl}octahydrocyclopenta[b]pyran-2-yl]-1,3-thiazole-4-carboxylic acid;

(57)
2-[(2R,4aR,5R,6R,7aS)-6-hydroxy-5-{2-[4-(trifluoromethoxy)phenoxy]ethyl}octahydrocyclopenta[b]pyran-2-yl]-1,3-thiazole-4-carboxylic acid;

(58)
2-[(2R,4aR,5R,6R,7aS)-6-hydroxy-5-{2-[2-(trifluoromethyl)phenoxy]ethyl}octahydrocyclopenta[b]pyran-2-yl]-1,3-thiazole-4-carboxylic acid;

(59)
2-[(2R,4aR,5R,6R,7aS)-6-hydroxy-5-{2-[3-(trifluoromethyl)phenoxy]ethyl}octahydrocyclopenta[b]pyran-2-yl]-1,3-thiazole-4-carboxylic acid;

(60)
2-[(2R,4aR,5R,6R,7aS)-6-hydroxy-5-{2-[4-(trifluoromethyl)phenoxy]ethyl}octahydrocyclopenta[b]pyran-2-yl]-1,3-thiazole-4-carboxylic acid;

(61)
2-{(2R,4aR,5R,6R,7aS)-6-hydroxy-5-[2-(2-methoxyphenoxy)ethyl]octahydrocyclopenta[b]pyran-2-yl}-1,3-thiazole-4-carboxylic acid;

(62)
2-{(2R,4aR,5R,6R,7aS)-6-hydroxy-5-[2-(3-methoxyphenoxy)ethyl]octahydrocyclopenta[b]pyran-2-yl}-1,3-thiazole-4-carboxylic acid;

(63)
2-{(2R,4aR,5R,6R,7aS)-6-hydroxy-5-[2-(4-methoxyphenoxy)ethyl]octahydrocyclopenta[b]pyran-2-yl}-1,3-thiazole-4-carboxylic acid;

(64)
2-{(2R,4aR,5R,6R,7aS)-6-hydroxy-5-[2-(3-methyl-4-nitrophenoxy)ethyl]octahydrocyclopenta[b]pyran-2-yl}-1,3-thiazole-4-carboxylic acid;

(65)
2-{(2R,4aR,5R,6R,7aS)-5-[2-(3,4-dichlorophenoxy)ethyl]-6-hydroxyoctahydrocyclopenta[b]pyran-2-yl}-1,3-thiazole-4-carboxylic acid;

(66) isopropyl
2-{(2R,4aR,5R,6R,7aS)-6-hydroxy-5-[2-(3-methyl-4-nitrophenoxy)ethyl]octahydrocyclopenta[b]pyran-2-yl}-1,3-thiazole-4-carboxylate; and

(67)
(2R,4aR,5R,6R,7aS)-5-[2-(3,4-dichlorophenoxy)ethyl]-2-[4-(hydroxymethyl)-1,3-thiazol-2-yl]octahydrocyclopenta[b]pyran-6-ol.

10. The compound according to item 1 or 3, a salt or N-oxide of the compound, or a solvate or prodrug of the compound or the salt or N-oxide, wherein the compound is selected from:

(1)
2-{(2R,4aR,5S,7aS)-5-[(2,3-dihydro-1H-inden-5-yloxy)methyl]-6,6-difluorooctahydrocyclopenta[b]pyran-2-yl}-1,3-thiazole-4-carboxylic acid; and (2)
2-{(2R,4aR,5S,6S,7aS)-5-[(4-chloro-3-methylphenoxy)methyl]-6-fluorooctahydrocyclopenta[b]pyran-2-yl}-1,3-thiazole-4-carboxylic acid.

11. A pharmaceutical composition comprising a compound represented by general formula (I), a salt or N-oxide of the compound, or a solvate or prodrug of the compound or the salt or N-oxide.

12. A therapeutic and/or prophylactic agent for a disease associated with an EP2 receptor, comprising a compound represented by general formula (I), a salt or N-oxide of the compound, or a solvate or prodrug of the compound or the salt or N-oxide.

13. Use of a compound represented by general formula (I), a salt or N-oxide of the compound, or a solvate or prodrug of the compound or the salt or N-oxide for the production of a therapeutic and/or prophylactic agent for a disease associated with an EP2 receptor.

14. A compound represented by general formula (I), a salt or N-oxide of the compound, or a solvate or prodrug of the compound or the salt or N-oxide for use in the treatment and/or prevention of a disease associated with an EP2 receptor.

15. A method for treating and/or preventing a disease associated with an EP2 receptor, comprising administering an effective amount of a compound represented by general formula (I), a salt or N-oxide of the compound, or a solvate or prodrug of the compound or the salt or N-oxide to a mammal.

Advantageous Effects of Invention

The compound according to the present invention has an EP2 agonist activity, and is therefore useful as a therapeutic agent for EP2 receptor-related diseases, including immune diseases (e.g., autoimmune diseases such as amyotrophic lateral sclerosis, multiple sclerosis, Sjogren's syndrome, chronic rheumatoid arthritis and systemic lupus erythematosus; a rejection after organ transplantation), allergic diseases (e.g., bronchial asthma, allergic rhinitis, allergic conjunctivitis, atopic dermatitis, food allergy), neuronal death, dysmenorrhea, premature birth, miscarriage, baldness, ocular diseases (e.g., glaucoma, ocular hypertension, macular edema, macular degeneration, retina and optic nerve tensile force rise, myopia, hypermetropia, astigmatism, dry eye, retinal detachment, cataract, intraocular pressure rise), erectile dysfunction, arthritis, lung injury, pulmonary fibrosis, pulmonary emphysema, bronchitis, chronic obstructive pulmonary disease, liver injury, acute hepatitis, cirrhosis, shock, nephritis (e.g., acute nephritis, chronic nephritis), renal failure, cardiovascular diseases (e.g., hypertension, myocardial ischemia, chronic arterial occlusive disease, vibration disease), systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases (e.g., bone fracture, bone refracture, intractable bone fracture, bone nonunion, pseudarthrosis, osteomalacia, bone Paget's disease, ankylosing spondylitis, cancer bone metastasis, arthrosis deformans, and bone destruction in analogous diseases thereto), cartilage injury and others.

DESCRIPTION OF EMBODIMENTS

The present invention relates to: a compound represented by the above-mentioned general formula (I):

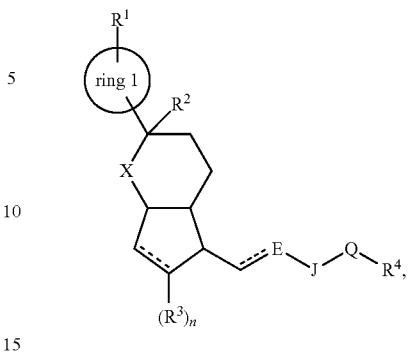

a salt or N-oxide of the compound, or a solvate or prodrug of the compound or the salt or N-oxide (wherein these substances are sometimes abbreviated as "a compound of the present invention" comprehensively, hereinafter); a pharmaceutical composition containing the compound of the present invention; and a prophylactic and/or therapeutic agent for a disease associated with an EP2 receptor, which comprises the compound of the present invention.

In the specification, specific examples of the 5- or 6-membered monocyclic aromatic ring include a benzene ring and a 5- or 6-membered monocyclic aromatic heterocyclic ring. Specific examples of the 5-membered monocyclic aromatic heterocyclic ring include a pyrrole ring, an imidazole ring, a triazole ring, a tetrazole ring, a pyrazole ring, a furan ring, a thiophene ring, an oxazole ring, an isoxazole ring, a thiazole ring, an isothiazole ring, a furazan ring, an oxadiazole ring and a thiadiazole ring. Specific examples of the 6-membered monocyclic aromatic heterocyclic ring include a pyridine ring, a pyrazine ring, a pyrimidine ring and a pyridazine ring.

In the specification, specific examples of the C1-4 alkyl group include a methyl group, an ethyl group, a propyl group, a butyl group and isomers thereof.

In the specification, specific examples of the C2-4 alkenyl group include an ethenyl group, a propenyl group, a butenyl group, a butadienyl group, and isomers thereof.

In the specification, specific examples of the C2-4 alkynyl group include an ethynyl group, a propenyl group, a butynyl group, a butadiynyl group, and isomers thereof.

In the specification, specific examples of the C1-4 alkoxy group include a methoxy group, an ethoxy group, a propoxy group, a butoxy group, and isomers thereof.

In the specification, specific examples of the C1-4 acyl group include a methanoyl group, an ethanoyl group, a propanoyl group, a butanoyl group and isomers thereof.

In the specification, specific examples of the C1-4 alkylene group include a methylene group, an ethylene group, a propylene group, a butylene group, and isomers thereof.

In the specification, specific examples of the saturated 5- to 8-membered cyclic amine include a pyrrolidine ring, an imidazolidine ring, a triazolidine ring, a tetrazolidine ring, a pyrazolidine ring, a piperidine ring, a piperazine ring, a perhydropyrimidine ring, a perhydropyridazine ring, a perhydroazepine ring, a perhydrodiazepine ring, a tetrahydrooxazole (oxazolidine) ring, a tetrahydroisoxazole (isoxazolidine) ring, a tetrahydrothiazole (thiazolidine) ring, a tetrahydroisothiazole (isothiazolidine) ring, a tetrahydrofurazan ring, a tetrahydrooxadiazole (oxadiazolidine) ring, a tetrahydrooxazine ring, a tetrahydrooxadiazine ring, a perhydrooxazepine ring, a perhydrooxadiazepine ring, a tetrahydrothiadiazole (thiadiazolidine) ring, a tetrahydrothiazine ring, a tetrahydrothiadiazine ring, a perhydrothiazepine ring, a perhydrothiadiazepine ring, a morpholine ring and a thiomorpholine ring.

In the specification, specific examples of the C3-6 saturated carbon ring include a cyclopropane ring, a cyclobutane ring, a cyclopentane ring and a cyclohexane ring.

In the specification, the C1-8 alkyl group includes a methyl group, an ethyl group, a propyl group, a butyl group, a pentyl group, a hexyl group, a heptyl group, an octyl group and isomers thereof.

In the specification, the C2-8 alkenyl group refers to, for example, a C2-8 alkenyl group having 1 to 2 double bonds, and specifically includes an ethenyl group, a propenyl group, a butenyl group, a butadienyl group, a pentenyl group, a pentadienyl group, a hexenyl group, a hexadienyl group, a heptenyl group, a heptadienyl group, an octenyl group, an octadienyl group and isomers thereof.

In the specification, the C2-8 alkynyl group refers to, for example, a C2-8 alkynyl group having 1 to 2 triple bonds, and specifically includes an ethynyl group, a propenyl group, a butynyl group, a butadiynyl group, a pentynyl group, a pentadiynyl group, a hexynyl group, a hexadiynyl group, a heptynyl group, a heptadiynyl group, an octynyl group, an octadiynyl group and isomers thereof.

In the specification, the C3-8 cycloalkyl group includes a cyclopropyl group, a cyclobutyl group, a cyclopentyl group, a cyclohexyl group, a cycloheptyl group and a cyclooctyl group.

In the specification, the C1-8 alkoxy group includes a methoxy group, an ethoxy group, a propoxy group, a butoxy group, a pentyloxy group, a hexyloxy group, a heptyloxy group, an octyloxy group and isomers thereof.

In the specification, the C3-8 cycloalkyloxy group includes a cyclopropyloxy group, a cyclobutyloxy group, a cyclopentyloxy group, a cyclohexyloxy group, a cycloheptyloxy group and a cyclooctyloxy group.

In the specification, the C1-8 acyl group includes a methanoyl group, an ethanoyl group, a propanoyl group, a butanoyl group, a pentanoyl group, a hexanoyl group, a heptanoyl group, an octanoyl group and isomers thereof.

In the specification, the C1-8 acyloxy group includes a methanoyloxy group, an ethanoyloxy group, a propanoyloxy group, a butanoyloxy group, a pentanoyloxy group, a hexanoyloxy group, a heptanoyloxy group, an octanoyloxy group and isomers thereof.

In the specification, the C1-8 alkylthio group includes a methylthio group, an ethylthio group, a propylthio group, a butylthio group, a pentylthio group, a hexylthio group, a heptylthio group, an octylthio group and isomers thereof.

In the specification, the C3-8 cycloalkylthio group includes a cyclopropylthio group, a cyclobutylthio group, a cyclopentylthio group, a cyclohexylthio group, a cycloheptylthio group and a cyclooctylthio group.

In the specification, the C1-8 alkylsulfinyl group includes a methylsulfinyl group, an ethylsulfinyl group, a propylsulfinyl group, a butylsulfinyl group, a pentylsulfinyl group, a hexylsulfinyl group, a heptylsulfinyl group, an octylsulfinyl group and isomers thereof.

In the specification, the C3-8 cycloalkylsulfinyl group includes a cyclopropylsulfinyl group, a cyclobutylsulfinyl group, a cyclopentylsulfinyl group, a cyclohexylsulfinyl group, a cycloheptylsulfinyl group and a cyclooctylsulfinyl group.

In the specification, the C1-8 alkylsulfonyl group includes a methylsulfonyl group, an ethylsulfonyl group, a propylsulfonyl group, a butylsulfonyl group, a pentylsulfonyl group, a hexylsulfonyl group, a heptylsulfonyl group, an octylsulfonyl group and isomers thereof.

In the specification, the C3-8 cycloalkylsulfonyl group includes a cyclopropylsulfonyl group, a cyclobutylsulfonyl group, a cyclopentylsulfonyl group, a cyclohexylsulfonyl group, a cycloheptylsulfonyl group and a cyclooctylsulfonyl group.

In the specification, the C1-8 alkoxycarbonyl group includes a methoxycarbonyl group, an ethoxycarbonyl group, a propoxycarbonyl group, a butoxycarbonyl group, a pentyloxycarbonyl group, a hexyloxycarbonyl group, a heptyloxycarbonyl group, an octyloxycarbonyl group and isomers thereof.

In the specification, the 5- or 6-membered cyclic group indicates a 5- or 6-membered carbon ring and a 5- or 6-membered heterocyclic ring.

Specific examples of the 5- or 6-membered carbon ring include a cyclopentane ring, a cyclohexane ring, a cyclopentene ring, a cyclohexene ring, a cyclopentadiene ring, a cyclohexadiene ring and a benzene ring.

Specific examples of the 5- or 6-membered heterocyclic ring include a pyrrole ring, an imidazole ring, a triazole ring, a tetrazole ring, a pyrazole ring, a pyridine ring, a pyrazine ring, a pyrimidine ring, a pyridazine ring, a furan ring, a pyran ring, a thiophene ring, a thiopyran ring, an oxazole ring, an isoxazole ring, a thiazole ring, an isothiazole ring, a furazan ring, an oxadiazole ring, an oxazine ring, an oxadiazine ring, a thiadiazole ring, a thiazine ring, a thiadiazine ring, a pyrroline ring, a pyrrolidine ring, an imidazoline ring, an imidazolidine ring, a triazoline ring, a triazolidine ring, a tetrazoline ring, a tetrazolidine ring, a pyrazoline ring, a pyrazolidine ring, a dihydropyridine ring, a tetrahydropyridine ring, a piperidine ring, a dihydropyrazine ring, a tetrahydropyrazine ring, a piperazine ring, a dihydropyrimidine ring, a tetrahydropyrimidine ring, a perhydropyrimidine ring, a dihydropyridazine ring, a tetrahydropyridazine ring, a perhydropyridazine ring, a dihydrofuran ring, a tetrahydrofuran ring, a dihydropyran ring, a tetrahydropyran ring, a dihydrothiophene ring, a tetrahydrothiophene ring, a dihydrothiopyran ring, a tetrahydrothiopyran ring, a dihydrooxazole ring, a tetrahydrooxazole (oxazolidine) ring, a dihydroisoxazole ring, a tetrahydroisoxazole (isoxazolidine) ring, a dihydrothiazole ring, a tetrahydrothiazole (thiazolidine) ring, a dihydroisothiazole ring, a tetrahydroisothiazole (isothiazolidine) ring, a dihydrofurazan ring, a tetrahydrofurazan ring, a dihydrooxadiazole ring, a tetrahydrooxadiazole (oxadiazolidine) ring, a dihydrooxazine ring, a tetrahydrooxazine ring, a dihydrooxadiazine ring, a tetrahydrooxadiazine ring, a dihydrothiadiazole ring, a tetrahydrothiadiazole (thiadiazolidine) ring, a dihydrothiazine ring, a tetrahydrothiazine ring, a dihydrothiadiazine ring, a tetrahydrothiadiazine ring, a morpholine ring, a thiomorpholine ring, an oxathiane ring, a dioxolane ring, a dioxane ring, a dithiolane ring and a dithiane ring.

In the specification, the 3- to 15-membered cyclic group includes a 3- to 15-membered carbon ring and a 3- to 15-membered heterocyclic ring.

Specific examples of the 3- to 15-membered carbon ring include a cyclopropane ring, a cyclobutane ring, a cyclopentane ring, a cyclohexane ring, a cycloheptane ring, a cyclooctane ring, a cyclononane ring, a cyclodecane ring, a cycloundecane ring, a cyclododecane ring, a cyclotridecane ring, a cyclotetradecane ring, a cyclopentadecane ring, a cyclopentene ring, a cyclohexene ring, a cycloheptene ring, a cyclooctene ring, a cyclopentadiene ring, a cyclohexadiene ring, a cycloheptadiene ring, a cyclooctadiene ring, a benzene ring, a pentalene ring, a perhydropentalene ring, an azulene ring, a perhydroazulene ring, an indene ring, a perhydroindene ring, an indan ring, a naphthalene ring, a dihydronaphthalene ring, a teterahydronaphthalene ring, a perhydronaphthalene ring, a heptalene ring, a perhydroheptalene ring, a biphenylene ring, an as-indacene ring, an s-indacene ring, an acenaphthylene ring, an acenaphthene ring, a fluorene ring, a phenalene ring, a phenanthrene ring, an anthracene ring, a spiro[4.4]nonane ring, a spiro[4.5]decane ring, a spiro[5.5]undecane ring, a bicyclo[2.2.1]heptane ring, a bicyclo[2.2.1]hept-2-ene ring, a bicyclo[3.1.1]heptane ring, a bicyclo[3.1.1]hept-2-ene ring, a bicyclo[2.2.2]octane ring, a bicyclo[2.2.2]oct-2-ene ring, a bicyclo[4.2.0]octa-1,3,5-triene ring, a 2,3-dihydro-1H-indene ring, a 1,2,3,4-tetrahydronaphthalene ring, a 6,7,8,9-tetrahydro-5H-benzo[7]annulene ring, a 5,6,7,8,9,10-hexahydrobenzo[8]annulene ring, a 2',3'-dihydrospirocyclopropane-1,1'-indene ring, a 3',4'-dihydro-2'H-spirocyclopropane-1,1'-naphthalene ring, an adamantane ring, a noradamantane ring and a Cubane ring.

Specific examples of the 3- to 15-membered heterocyclic ring include a pyrrole ring, an imidazole ring, a triazole ring, a tetrazole ring, a pyrazole ring, a pyridine ring, a pyrazine ring, a pyrimidine ring, a pyridazine ring, an azepine ring, a diazepine ring, a furan ring, a pyran ring, an oxepine ring, a thiophene ring, a thiopyran ring, a thiepine ring, an oxazole ring, an isoxazole ring, a thiazole ring, an isothiazole ring, a furazan ring, an oxadiazole ring, an oxazine ring, an oxadiazine ring, an oxazepine ring, an oxadiazepine ring, a thiadiazole ring, a thiazine ring, a thiadiazine ring, a thiazepine ring, a thiadiazepine ring, an indole ring, an isoindole ring, an indolizine ring, a benzofuran ring, an isobenzofuran ring, a benzothiophene ring, an isobenzothiophene ring, a dithianaphthalene ring, an indazole ring, a quinoline ring, an isoquinoline ring, a quinolizine ring, a purine ring, a phthalazine ring, a pteridine ring, a naphthyridine ring, a quinoxaline ring, a quinazoline ring, a cinnoline ring, a benzoxazole ring, a benzothiazole ring, a benzimidazole ring, a chromene ring, a benzoxepine ring, a benzoxazepine ring, a benzoxadiazepine ring, a benzothiepine ring, a benzothiazepine ring, a benzothiadiazepine ring, a benzazepine ring, a benzodiazepine ring, a benzofurazan ring, a benzothiadiazole ring, a benzotriazole ring, a carbazole ring, a β-carboline ring, an acridine ring, a phenazine ring, a dibenzofuran ring, a xanthene ring, a dibenzothiophene ring, a phenothiazine ring, a phenoxazine ring, a phenoxathiin ring, a thianthrene ring, a phenanthridine ring, a phenanthroline ring, a perimidine ring, an aziridine ring, an azetidine ring, a pyrroline ring, a pyrrolidine ring, an imidazoline ring, an imidazolidine ring, a triazoline ring, a triazolidine ring, a tetrazoline ring, a tetrazolidine ring, a pyrazoline ring, a pyrazolidine ring, a dihydropyridine ring, a tetrahydropyridine ring, a piperidine ring, a dihydropyrazine ring, a tetrahydropyrazine ring, a piperazine ring, a dihydropyrimidine ring, a tetrahydropyrimidine ring, a perhydropyrimidine ring, a dihydropyridazine ring, a tetrahydropyridazine ring, a perhydropyridazine ring, a dihydroazepine ring, a tetrahydroazepine ring, a perhydroazepine ring, a dihydrodiazepine ring, a tetrahydrodiazepine ring, a perhydrodiazepine ring, an oxirane ring, an oxetane ring, a dihydrofuran ring, a tetrahydrofuran ring, a dihydropyran ring, a tetrahydropyran ring, a dihydrooxepine ring, a tetrahydrooxepine ring, a perhydrooxepine ring, a thiirane ring, a thietane ring, a dihydrothiophene ring, a tetrahydrothiophene ring, a dihydrothiopyran ring, a tetrahydrothiopyran ring, a dihydrothiepine ring, a tetrahydrothiepine ring, a perhydrothiepine ring, a dihydrooxazole ring, a tetrahydrooxazole (oxazolidine) ring, a dihydroisoxazole ring, a tetrahydroisoxazole (isoxazolidine) ring, a dihydrothiazole ring, a tetrahydrothiazole (thiazolidine) ring, a dihydroisothiazole ring, a tetrahydroisothiazole (isothiazolidine) ring, a dihydrofurazan ring, a tetrahydrofurazan ring, a dihydrooxadiazole ring, a tetrahydrooxadiazole (oxadiazolidine) ring, a dihydrooxazine ring, a tetrahydrooxazine ring, a dihydrooxadiazine ring, a tetrahydrooxadiazine ring, a dihydrooxazepine ring, a tetrahydrooxazepine ring, a perhydrooxazepine ring, a dihydrooxadiazepine ring, a tetrahydrooxadiazepine ring, a perhydrooxadiazepine ring, a dihydrothiadiazole ring, a tetrahydrothiadiazole (thiadiazolidine) ring, a dihydrothiazine ring, a tetrahydrothiazine ring, a dihydrothiadiazine ring, a tetrahydrothiadiazine ring, a dihydrothiazepine ring, a tetrahydrothiazepine ring, a perhydrothiazepine ring, a dihydrothiadiazepine ring, a tetrahydrothiadiazepine ring, a perhydrothiadiazepine ring, a morpholine ring, a thiomorpholine ring, an oxathiane ring, an indoline ring, an isoindoline ring, a dihydrobenzofuran ring, a perhydrobenzofuran ring, a dihydroisobenzofuran ring, a perhydroisobenzofuran ring, a dihydrobenzothiophene ring, a perhydrobenzothiophene ring, a dihydroisobenzothiophene ring, a perhydroisobenzothiophene ring, a dihydroindazole ring, a perhydroindazole ring, a dihydroquinoline ring, a tetrahydroquinoline ring, a perhydroquinoline ring, a dihydroisoquinoline ring, a tetrahydroisoquinoline ring, a perhydroisoquinoline ring, a dihydrophthalazine ring, a tetrahydrophthalazine ring, a perhydrophthalazine ring, a dihydronaphthyridine ring, a tetrahydronaphthyridine ring, a perhydronaphthyridine ring, a dihydroquinoxaline ring, a tetrahydroquinoxaline ring, a perhydroquinoxaline ring, a dihydroquinazoline ring, a tetrahydroquinazoline ring, a perhydroquinazoline ring, a dihydrocinnoline ring, a tetrahydrocinnoline ring, a perhydrocinnoline ring, a benzoxathiane ring, a dihydrobenzoxazine ring, a dihydrobenzothiazine ring, a pyrazinomorpholine ring, a dihydrobenzoxazole ring, a perhydrobenzoxazole ring, a dihydrobenzothiazole ring, a perhydrobenzothiazole ring, a dihydrobenzimidazole ring, a perhydrobenzimidazole ring, a dihydrobenzazepine ring, a tetrahydrobenzazepine ring, a dihydrobenzodiazepine ring, a tetrahydrobenzodiazepine ring, a benzodioxepane ring, a dihydrobenzoxazepine ring, a tetrahydrobenzoxazepine ring, a dihydrocarbazole ring, a tetrahydrocarbazole ring, a perhydrocarbazole ring, a dihydroacridine ring, a tetrahydroacridine ring, a perhydroacridine ring, a dihydrodibenzofuran ring, a dihydrodibenzothiophene ring, a tetrahydrodibenzofuran ring, a tetrahydrodibenzothiophene ring, a perhydrodibenzofuran ring, a perhydrodibenzothiophene ring, a dioxolane ring, a dioxane ring, a dithiolane ring, a dithiane ring, a dioxaindan ring, a benzodioxane ring, a chroman ring, a benzodithiolane ring, a benzodithiane ring, an azaspiro[4.4]nonane ring, an oxaspiro[4.4]nonane ring, a dioxaspiro[4.4]nonane ring, an azaspiro[4.5]decane ring, a thiaspiro[4.5]decane ring, a dithiaspiro[4.5]decane ring, a dioxaspiro[4.5]decane ring, an oxazaspiro[4.5]decane ring, an azaspiro[5.5]undecane ring, an oxaspiro[5.5]undecane ring, a dioxaspiro[5.5]undecane ring, an azabicyclo[2.2.1]heptane ring, an oxabicyclo[2.2.1]heptane ring, an azabicyclo[3.1.1]heptane ring, an azabicyclo[3.2.1]octane ring, an oxabicyclo[3.2.1]octane ring, an azabicyclo[2.2.2]octane ring and a diazabicyclo[2.2.2]octane ring.

In the specification, the halogen atom includes a fluorine atom, a bromine atom, a chlorine atom and an iodine atom.

In the specification,

⁼⁼⁼⁼⁼ represents a single bond or a double bond,

,,,,ᴡᴡ represents that a group is bonded on the back side of the paper (i.e., in an α-configuration),

↗ represents that a group is bonded on the front side of the paper (i.e., in a β-configuration), and

/ represents that a group is a group in an α-configuration, a group in a β-configuration or a mixture thereof at a specific mixing ratio.

Preferred embodiment of the compound represented by general formula (I) include a compound represented by general formula (I-1):

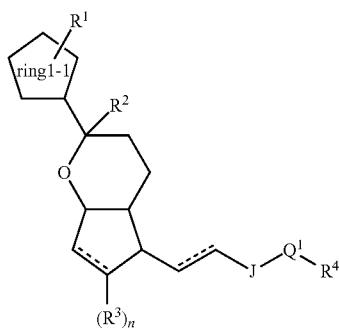

(I-1)

(wherein ring 1-1 represents a 5-membered monocyclic aromatic heterocyclic ring; $Q^1$ represents —$CH_2$—, —O—, —O—$CH_2$—, —S—, —SO—, —$SO_2$—, or —$NR^{18}$—; and other symbols are as defined above) and a compound represented by general formula (I-2):

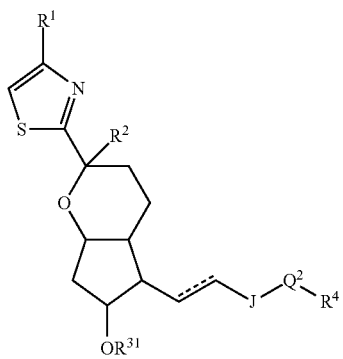

(I-2)

(wherein $Q^2$ represents —$CH_2$—, —O—, —O—$CH_2$—, —S— or —$NR^{18}$—; and other symbols are as defined above).

In general formula (I), ring 1 is preferably a 5-membered monocyclic aromatic heterocyclic ring, more preferably an oxazole ring, a thiazole ring, a furan ring or a thiophene ring, more preferably a thiazole ring.

In general formula (I-1), ring 1-1 is preferably an oxazole ring, a thiazole ring, a furan ring or a thiophene ring, more preferably a thiazole ring.

In all of general formula (I), general formula (I-1) and general formula (I-2), p is preferably 0.

In all of general formula (I), general formula (I-1) and general formula (I-2), q is preferably 0.

In all of general formula (I), general formula (I-1) and general formula (I-2), r is preferably 1.

In all of general formula (I), general formula (I-1) and general formula (I-2), s is preferably 1.

In all of general formula (I), general formula (I-1) and general formula (I-2), R' is preferably —$(CH_2)_p$—COOH, —$(CH_2)_q$—$COOR^{11}$, —$(CH_2)_r$—OH or —$(CH_2)_s$—$OR^{12}$, particularly preferably —COOH, —$COOR^{11}$, —$CH_2OH$ or —$CH_2OR^{12}$, and $R^{11}$ is preferably an isopropyl group.

In all of general formula (I), general formula (I-1) and general formula (I-2), $R^2$ is preferably a hydrogen atom or a methyl group.

In both of general formula (I) and general formula (I-1), n is preferably 2, and the combination of $R^3$'s when n is 2 is preferably a combination of a hydrogen atom and —$OR^{31}$, wherein $R^{31}$ is preferably a hydrogen atom.

In general formula (I-2), $R^{31}$ is preferably a hydrogen atom.

In general formula (I), E is preferably —$CH_2$— or =CH—.

In all of general formula (I), general formula (I-1) and general formula (I-2), $R^7$ in J is preferably a hydrogen atom, a hydroxy group or a halogen atom, particularly preferably a hydrogen atom or a hydroxy group.

In all of general formula (I), general formula (I-1) and general formula (I-2), $R^8$ in J is preferably a hydrogen atom, a hydroxy group or a halogen atom, particularly preferably a hydrogen atom or a hydroxy group.

In general formula (I), the combination of $R^7$ and $R^8$ that are bound to the same carbon atom in J is preferably (1) a combination of a hydrogen atom and a hydrogen atom, (2) a combination of a halogen atom and a halogen atom, or (3) a combination of a hydrogen atom and a hydroxy group.

In general formula (I), X is preferably —O— or —S—, particularly preferably —O—.

In general formula (I), Q is preferably —$CH_2$—, —O—, —O—$CH_2$—, —S—, —SO—, —$SO_2$— or —$NR^{18}$—, more preferably —$CH_2$—, —O—, —O—$CH_2$—, —S— or —$NR^{18}$—, particularly preferably —$CH_2$— or —O—.

In general formula (I-1), $Q^1$ is preferably —$CH_2$—, —O—, —S— or —$NR^{18}$—, particularly preferably —$CH_2$— or —O—.

In general formula (I-2), $Q^2$ is preferably —$CH_2$— or —O—.

In all of general formula (I), general formula (I-1) and general formula (I-2), $R^4$ is preferably a C1-4 alkyl group or a 3- to 15-membered ring.

The 3- to 15-membered ring is preferably a cyclopentane ring, a cyclohexane ring, a benzene ring or an 8- to 15-membered benzene condensed ring. Specific examples of the 8- to 15-membered benzene condensed ring include an indene ring, an indan ring, a naphthalene ring, a dihydronaphthalene ring, a teterahydronaphthalene ring, a biphenylene ring, an acenaphthylene ring, an acenaphthene ring, a fluorene ring, a phenalene ring, a phenanthrene ring, an anthracene ring, a bicyclo[4.2.0]octa-1,3,5-triene ring, a 2,3-dihydro-1H-indene ring, a 1,2,3,4-tetrahydronaphthalene ring, a 6,7,8,9-tetrahydro-5H-benzo[7]annulene ring, a 5,6,7,8,9,10-hexahydrobenzo[8]annulene ring, a 2',3'-dihydrospirocyclopropane-1,1'-indene ring, a 3',4'-dihydro-2'H-spirocyclopropane-1,1'-naphthalene ring, an indole ring, a benzofuran ring, a benzothiophene ring, a dithianaphthalene ring, an indazole ring, a quinoline ring, an isoquinoline ring, a phthalazine ring, a quinoxaline ring, a quinazoline ring, a cinnoline ring, a benzoxazole ring, a benzothiazole ring, a benzimidazole ring, a chromene ring, a benzoxepine ring, a benzoxazepine ring, a benzoxadiazepine ring, a benzothiepine ring, a benzothiazepine ring, a benzothiadiazepine ring, a benzazepine ring, a benzodiazepine ring, a benzotriazole ring, a carbazole ring, a β-carboline ring, an acridine ring, a phenazine ring, a dibenzofuran ring, a xanthene ring, a dibenzothiophene ring, a phenothiazine ring, a phenoxazine ring, a phenoxathiin ring, a thianthrene ring, a phenanthridine ring, a phenanthroline ring, a perimidine ring, an indoline ring, an isoindoline ring, a dihydrobenzofuran ring, a dihydroisobenzofuran ring, a dihydrobenzothiophene ring, a dihydroisobenzothiophene ring, a dihydroindazole ring, a dihydroquinoline ring, a tetrahydroquinoline ring, a dihydroisoquinoline ring, a tetrahydroisoquinoline ring, a dihydrophthalazine ring, a tetrahydrophthalazine ring, a dihydroquinoxaline ring, a tetrahydroquinoxaline ring, a dihydroquinazoline ring, a tetrahydroquinazoline ring, a dihydrocinnoline ring, a tetrahydrocinnoline ring, a benzoxathiane ring, a dihydrobenzoxazine ring, a dihydrobenzothiazine ring, a dihydrobenzoxazole ring, a dihydrobenzothiazole ring, a dihydrobenzimidazole ring, a dihydrobenzazepine ring, a tetrahydrobenzazepine ring, a dihydrobenzodiazepine ring, a tetrahydrobenzodiazepine ring, a benzodioxepane ring, a dihydrobenzoxazepine ring, a tetrahydrobenzoxazepine ring, a dihydrocarbazole ring, a tetrahydrocarbazole ring, a dihydroacridine ring, a tetrahydroacridine ring, a dihydrodibenzofuran ring, a dihydrodibenzothiophene ring, a tetrahydrodibenzofuran ring, a tetrahydrodibenzothiophene ring, a dioxaindan ring, a benzodioxane ring, a chroman ring, a benzodithiolane ring and a benzodithiane ring.

In all of general formula (I), general formula (I-1) and general formula (I-2), the 3- to 15-membered ring in $R^4$ is more preferably a benzene ring or any one of the following 8- to 15-membered benzene condensed rings: an indene ring, an indan ring, a naphthalene ring, a dihydronaphthalene ring, a teterahydronaphthalene ring, a bicyclo[4.2.0]octa-1,3,5-triene ring, a 2,3-dihydro-1H-indene ring, a 1,2,3,4-tetrahydronaphthalene ring, a 6,7,8,9-tetrahydro-5H-benzo[7]annulene ring, a 5,6,7,8,9,10-hexahydrobenzo[8]annulene ring, a 2',3'-dihydrospirocyclopropane-1,1'-indene ring, a 3',4'-dihydro-2'H-spirocyclopropane-1,1'-naphthalene ring, an indole ring, a benzofuran ring, a benzothiophene ring, an indazole ring, a quinoline ring, an isoquinoline ring, a phthalazine ring, a quinoxaline ring, a quinazoline ring, a cinnoline ring, a benzoxazole ring, a benzothiazole ring, a benzimidazole ring, a chromene ring, an indoline ring, an isoindoline ring, a dihydrobenzofuran ring, a dihydroisobenzofuran ring, a dihydrobenzothiophene ring, a dihydroisobenzothiophene ring, a dihydroindazole ring, a dihydroquinoline ring, a tetrahydroquinoline ring, a dihydroisoquinoline ring, a tetrahydroisoquinoline ring, a dihydrophthalazine ring, a tetrahydrophthalazine ring, a dihydroquinoxaline ring, a tetrahydroquinoxaline ring, a dihydroquinazoline ring, a tetrahydroquinazoline ring, a dihydrocinnoline ring, a tetrahydrocinnoline ring, a dihydrobenzoxazine ring, a dihydrobenzothiazine ring, a dihydrobenzoxazole ring, a dihydrobenzothiazole ring, a dihydrobenzimidazole ring and a chroman ring.

In the case where the 3- to 15-membered ring is an 8- to 15-membered benzene condensed ring, it is preferred that the 8- to 15-membered benzene condensed ring is bound to Q at the benzene ring moiety.

In all of general formula (I), general formula (I-1) and general formula (I-2), particularly preferred examples of the 3- to 15-membered ring in $R^4$ include the following rings:

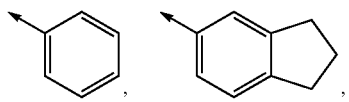

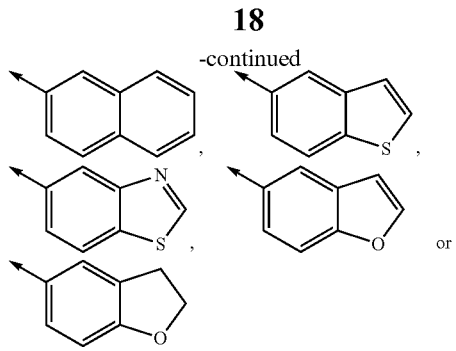

(wherein an arrow mark represents a bonding site for Q).

In all of general formula (I), general formula (I-1) and general formula (I-2), the 3- to 15-membered ring in $R^4$ is most preferably a benzene ring.

In all of general formula (I), general formula (I-1) and general formula (I-2), the 3- to 15-membered ring in $R^4$ may be substituted by 0 to 5 $R^5$'s, more preferably 0 to 3 $R^5$'s. In the case where the 3- to 15-membered ring is substituted by multiple $R^5$'s, a single atom that constitutes the 3- to 15-membered ring may be substituted by all of the $R^5$'s or different atoms that constitutes the 3- to 15-membered ring may be respectively substituted by the $R^5$'s, wherein the $R^5$'s may be the same as or different from each other.

In all of general formula (I), general formula (I-1) and general formula (I-2), $R^5$ that is a substituent for the 3- to 15-membered ring in $R^4$ is preferably any one of the abovementioned substituents (1) to (26), more preferably (1) a C1-8 alkyl group, (2) a C2-8 alkenyl group, (3) a C2-8 alkynyl group, (4) a C3-8 cycloalkyl group, (5) a C1-8 alkoxy group, (6) a C3-8 cycloalkyloxy group, (7) a C1-8 acyl group, (9) a C1-8 alkylthio group, (20) a halogen atom, (21) a hydroxy group, (22) a nitro group, (23) a cyano group, or (24) $-NR^{16}R^{17}$, particularly preferably (1) a C1-8 alkyl group, (5) a C1-8 alkoxy group, (20) a halogen atom, (22) a nitro group or (23) a cyano group.

In the compound represented by general formula (I), a combination in which some or all of ring 1, $R^1$, $R^2$, $R^3$, n, E, X, Q and $R^4$ are respectively selected from the preferred examples thereof is preferred.

In the compound represented by general formula (I-1), a combination in which some or all of ring 1-1, R', $R^2$, $R^3$, n, $Q^1$ and $R^4$ are respectively selected from the preferred examples thereof is preferred.

In the compound represented by general formula (I-2), a combination in which some or all of $R^1$, $R^2$, $R^{31}$, $Q^2$ and $R^4$ are respectively selected from the preferred examples thereof is preferred.

Among the compounds represented by general formula (I), general formula (I-1) and general formula (I-2), those compounds each having high EP2 selectivity are more preferred.

In addition, all of the compounds mentioned in the section "EXAMPLES" are also preferred.

[Isomer]

In the present invention, an isomer includes all isomers unless otherwise is indicated. For example, an alkyl group, an alkoxy group, an alkylene group and the like include those of linear forms and branched forms. In addition, all of an isomer at a double bond, a ring, or a condensed ring (E isomer, Z isomer, cis isomer, trans isomer), an isomer due to the presence of an asymmetric carbon etc. (R, S isomer, α-configuration, β-configuration, enantiomer, diastereomer), an optically active body having optical rotation (D, L, d, l isomer), a polar body derived from chromatographic separation (high polar compound, low polar compound), an equilibrated compound, a rotation isomer, a mixture of them at an arbitrary ratio, and a racemic mixture are included in the present invention. In addition, in the present invention, the isomer includes all isomers derived from tautomers.

Examples of the isomer of the compound represented by general formula (I) which occurs due to the presence of an asymmetric carbon include, but are not limited to, the compounds respectively represented by the following general formulae:

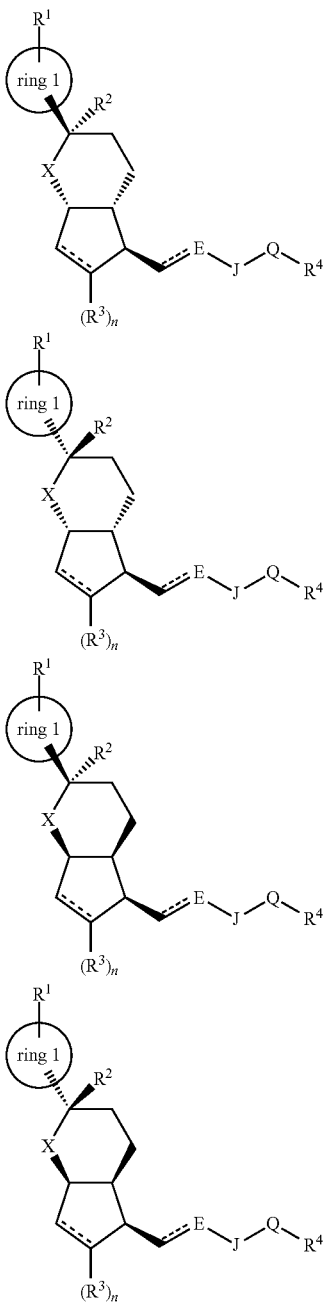

(wherein all of the symbols are as defined above), and the isomer is more preferably a compound represented by the following general formula.

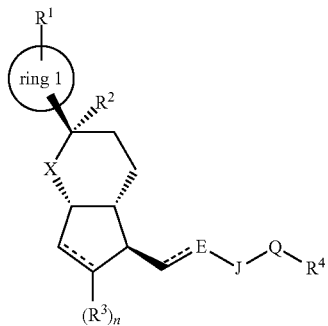

[Salt, N-Oxide, Solvate]

A salt of the compound represented by general formula (I) which is disclosed in the present invention include all of pharmaceutically acceptable salts of the compound. The pharmaceutically acceptable salt is preferably one which has low toxicity and is soluble in water. Examples of the proper salt include salts with an alkali metal (e.g., potassium, sodium, lithium), salts with an alkaline earth metal (e.g., calcium, magnesium), ammonium salts (e.g., a tetramethylammonium salt, a tetrabutylammonium salt), salts with an organic amine (e.g., alkylamines [e.g., methylamine, dimethylamine, trimethylamine, triethylamine], heterocyclic amines [e.g., pyridine, picoline, piperidine], alkanolamines [e.g., monoethanolamine, diethanolamine, triethanolamine], cyclopentylamine, cyclohexylamine, dicyclohexylamine, benzylamine, dibenzylamine, phenethylamine, N,N'-dibenzylethylenediamine, tris(hydroxymethyl)methylamine, N-methyl-D-glucamine, basic naturally-occurring amino acids [e.g., arginine, lysine, ornithine, histidine]), and acid addition salts (e.g., inorganic acid salts [e.g., hydrochloride, hydrobromide, hydroiodide, sulfate, phosphate, nitrate etc.]), organic acid salts [e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate etc.], salts with an acidic naturally-occurring amino acid [e.g., aspartate, glutamate]).

In addition, the salt also includes a quaternary ammonium salt. A quaternary ammonium salt is a compound produced by quaternizing a nitrogen atom in the compound represented by general formula (I) with a $R^0$ group. Here, the $R^0$ group includes a C1-8 alkyl group which may be substituted with a phenyl group, and the like.

An N-oxide of the compound represented by general formula (I) is a compound produced by oxidizing a nitrogen atom in the compound represented by general formula (I). The N-oxide may be in the form of a salt, such as the salt with an alkali metal, the salt with an alkaline earth metal, the ammonium salt, the salt with an organic amine and the acid addition salt, all are as mentioned above.

The compound represented by general formula (I), a salt or N-oxide of the compound may be in the form of a solvate with water, an alcohol-type solvent (e.g., ethanol) or the like. In the case where a solvate is formed, the compound, the salt or the N-oxide may be coordinated with an arbitrary number of solvent molecules. It is preferred that the solvate has low toxicity and is soluble in water.

The compound represented by general formula (I) can be converted to the salt, N-oxide or solvate by a known method.

[Prodrug]

A prodrug of the compound represented by general formula (I) refers to a compound which is converted into the compound represented by general formula (I) by a reaction with an enzyme or gastric acid in a living body. Examples of the prodrug of the compound represented by general formula (I) include as follows: when the compound represented by general formula (I) has a carboxy group, compounds in which the carboxy group is esterified or amidated (e.g., compounds in which a carboxyl group of the compound represented by general formula (I) is methyl-esterified, ethyl-esterified, isopropyl-esterified, phenyl-esterified, carboxymethyl-esterified, dimethylaminomethyl-esterified, pivaloyloxymethyl-esterified, phthalidyl-esterified, 1-{(ethoxycarbonyl)oxy}ethyl-esterified, (5-methyl-2-oxo-1,3-dioxolen-4-yl)methyl-esterified, 1-{[(cyclohexyloxy)carbonyl]oxy}ethyl-esterified or methyl-amidated); when the compound represented by general formula (I) has a hydroxy group, compounds in which the hydroxy group is acylated, alkylated, phosphorylated or borated (e.g., compounds in which a hydroxy group of the compound represented by general formula (I) is acetylated, palmitoylated, propanoylated, pivaloylated, succinylated, fumarated, alanylated or dimethylaminomethyl-carbonylated); and, when the compound represented by general formula (I) has an amino group, compounds in which the amino group is acylated, alkylated or phosphorylated (e.g., compounds in which an amino group of the compound represented by general formula (I) is eicosanoylated, alanylated, pentylamino-carbonylated, (5-methyl-2-oxo-1,3-dioxolen-4-yl)-methoxycarbonylated, tetrahydrofuranylated, pyrrolidylmethylated, pivaloyloxymethylated, acetoxymethylated or tert-butylated). The prodrug of the compound represented by general formula (I) may be a prodrug which is changed to the compound represented by general formula (I) under the physiological condition, as described in "Development of Medicaments" published by Hirokawa Shoten Co., Ltd., vol. 7, "Molecular Design", p. 163-198 (1990). The prodrug of the compound represented by general formula (I) can be produced by a method known per se. The prodrug of the compound represented by general formula (I) may be in the form of a salt, such as the salt with an alkali metal, the salt with an alkaline earth metal, the ammonium salt, the salt with an organic amine and the acid addition salt, all are as mentioned above, and may be also in the form of a solvate with water or an alcohol-based solvent (e.g., ethanol), likewise the compound represented by general formula (I).

[Labeled Compound]

The compound according to the present invention includes a so-called "labeled compound", i.e., a compound in which some or all of atoms that constitute the present compound are each substituted with its isotopic element. The labeled compound can be produced by a method known per se. Preferred examples of the isotopic element to be used for labeling include, but are not limited to, $^2$H, $^3$H, $^{13}$C, $^{14}$C, $^{15}$N, $^{16}$N, $^{17}$O, $^{18}$O, $^{18}$F, $^{35}$S, $^{36}$Cl, $^{77}$Br and $^{125}$I.

[Method for Producing Compound According to the Present Invention]

The compound according to the present invention can be produced by properly improving the method described in "Comprehensive Organic Transformations: A Guide to Functional Group Preparations, 2nd Edition (Richard C. Larock, John Wiley & Sons Inc, 1999)" or the method described in the section "EXAMPLES" and the like and employing a combination of the methods.

The compound represented by general formula (I) can be produced by the following methods.

A compound represented by general formula (I) wherein E is —O—, i.e., a compound represented by general formula (Ia):

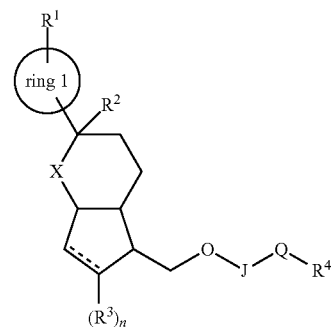

can be produced by subjecting a compound represented by general formula (II):

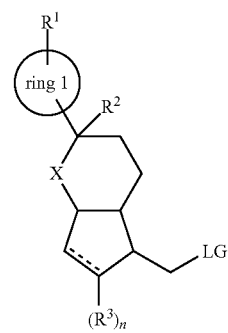

(wherein LG represents a leaving group (e.g., a halogen atom, a p-toluenesulfonyloxy group or a methanesulfonyloxy group); and other symbols are as defined above) and a compound represented by general formula (III):

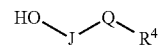

(wherein all of the symbols are as defined above) to a substitution reaction.

This substitution reaction is known and is carried out by, for example, reacting the compounds with each other in an organic solvent (e.g., dimethylformamide, dimethyl sulfoxide, chloroform, dichloromethane, diethyl ether, tetrahydrofuran, methyl t-butyl ether) in the presence of an alkali metal hydroxide (e.g., sodium hydroxide, potassium hydroxide, lithium hydroxide), an alkali earth metal hydroxide (e.g., barium hydroxide, calcium hydroxide) or a carbonate (e.g., sodium carbonate, potassium carbonate) or an aqueous solution thereof or a mixture thereof at 0 to 100° C.

A compound represented by general formula (I) wherein E is —O—, m in J is 0, Q is a bond and $R^4$ is a 3- to 15-membered ring, i.e., a compound represented by general formula (Ib):

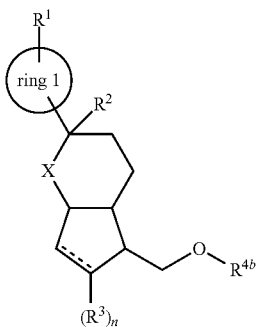

(wherein $R^{4b}$ represents a 3- to 15-membered ring; and other symbols are as defined above)
can be produced by subjecting a compound represented by general formula (IV):

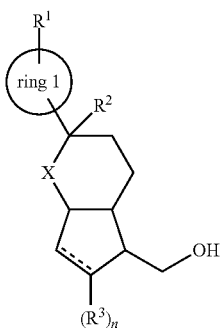

(wherein all of the symbols are as defined above)
and a compound represented by general formula (V):

(wherein $R^{4b}$ is as defined above)
to the Mitsunobu reaction.

The Mitsunobu reaction is known, and is carried out by, for example, reacting one alcohol with a phenol in an organic solvent (dichloromethane, diethyl ether, tetrahydrofuran, acetonitrile, benzene, toluene, etc.) at 0 to 60° C. in the presence of an azo compound (diethyl azodicarboxylate (DEAD), diisopropyl azodicarboxylate, 1,1'-(azodicarbonyl)dipiperidine, 1,1'-azobis(N,N-dimethylformamide), etc.) and a phosphine compound (e.g., triphenylphosphine, tributylphosphine, trimethylphosphine, polymer-supported triphenylphosphine, etc.).

A compound in which E is —S— can be produced by the same reaction as mentioned above using a compound represented by general formula (III) or general formula (V) in which the hydroxy group is —SH. A compound in which E is —SO— or —SO$_2$— can be produced by subjecting the compound in which E is —S— to an oxidation reaction of a sulfur atom.

The oxidation reaction for converting the compound in which E is —S— to the compound in which E is —SO— is known. For example, the oxidation reaction can be carried out by reacting the compound in which E is —S— at a temperature of −40 to 0° C. in an organic solvent (dichloromethane, chloroform, benzene, hexane, methanol, t-butyl alcohol, acetone, acetonitrile, tetrahydrofuran, acetic acid, N,N-dimethylformamide, etc.), water or a solvent mixture thereof in the presence of 1 to 1.2 equivalents of an oxidizing agent (hydrogen peroxide, sodium periodate, acyl nitrite, sodium perborate, sodium hypochlorite, peracids (3-chloroperbenzoic acid, peracetic acid, etc.), Oxone (trade name, abbreviated as "Oxone", hereinbelow; potassium peroxymonosulfate), potassium permanganate, chromic acid, dimethyldioxolane, etc,).

The oxidation reaction for converting the compound in which E is —S— to the compound in which E is —SO$_2$— is known. For example, the oxidation reaction can be carried out by reacting the compound in which E is —S— at a temperature of 0 to 60° C. in an adequate organic solvent (dichloromethane, chloroform, benzene, hexane, methanol, t-butyl alcohol, acetone, acetonitrile, tetrahydrofuran, acetic acid, N,N-dimethylformamide), water or a solvent mixture thereof in the presence of an excess amount of an oxidizing agent (hydrogen peroxide, sodium periodate, acyl nitrite, sodium perborate, sodium hypochlorite, peracids (3-chloroperbenzoic acid, peracetic acid), Oxone (trade name), potassium permanganate, chromic acid, dimethyldioxolane, etc.).

A compound represented by general formula (I) wherein E is —NH—, i.e., a compound represented by general formula (Ic):

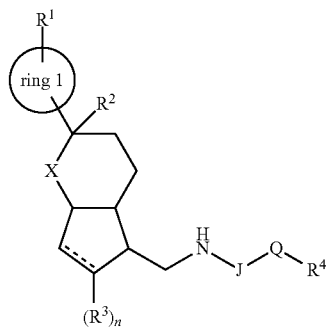

(wherein all of the symbols are as defined above)
can be produced by subjecting a compound represented by general formula (VI):

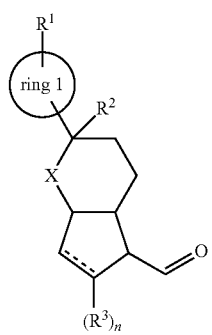

(wherein all of the symbols are as defined above)
and a compound represented by general formula (VII):

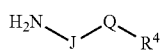

(wherein all of the symbols are as defined above) to a reductive amination reaction.

The reductive amination reaction is known, and is carried out by, for example, reacting the compounds at a temperature of 0 to 40° C. in an organic solvent (dichloroethane, dichloromethane, etc.) in the presence of a tertiary amine (e.g., triethylamine, diisopropylethylamine) using an acid (acetic acid, titanium tetrachloride, etc.) and then further carrying out the reaction at a temperature of 0 to 40° C. in the presence of a reducing agent (sodium tri(acetoxy)borohydride, sodium cyanoborohydride).

A compound represented by general formula (I) wherein E is =CH—, i.e., a compound represented by general formula (Id):

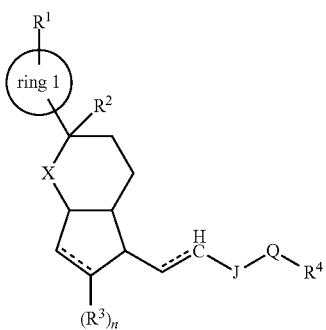

(Id)

(wherein all of the symbols are as defined above) can be produced by subjecting a compound represented by general formula (VI) and a compound represented by general formula (VIII):

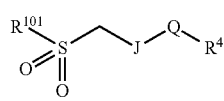

(VIII)

(wherein $R^{101}$ represents a phenyl group, a phenyltetrazolyl group, a benzothiazolyl group or the like; and other symbols are as defined above) to the below-mentioned reaction.

This reaction is known, and can be carried out, for example, at a temperature of −100 to −20° C. in an organic solvent (e.g., anhydrous tetrahydrofuran, dimethoxyethane, toluene, dimethylformamide) in the presence of a base (e.g., potassium hexamethyldisilazide (KHMDS), lithium diisopropylamide (LDA), butyllithium).

A compound wherein E is —CH$_2$— can be produced by subjecting a compound wherein E is =CH— to a known reduction reaction.

The reduction reaction of a double bond is known, and can be carried out, for example, at a temperature ranging from room temperature to about 80° C. under a hydrogen atmosphere in an organic solvent (e.g., methanol, ethanol, ethyl acetate, tetrahydrofuran, acetic acid, 1,2-dimethoxyethane, or a solvent mixture prepared by adequately mixing these organic solvents) or a solvent mixture of the organic solvent with water in the presence of a palladium catalyst (e.g., palladium-carbon, palladium hydroxide). The reduction can also be achieved with tosylhydrazine. For example, the reduction is carried out at a temperature of 0 to 100° C. in an organic solvent (e.g., 1,4-dioxane, ethanol, dichloromethane, ethylene glycol) or water in the presence of tosylhydrazine and a base (e.g., potassium carbonate, triethylamine, sodium acetate).

A compound represented by general formula (I) wherein E is —CH$_2$—, m in J is 0 and Q is —O—, i.e., a compound represented by general formula (Ie):

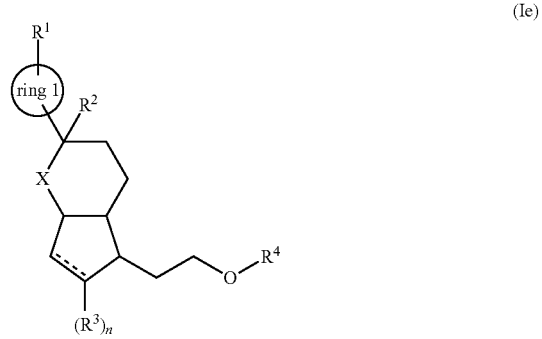

(Ie)

(wherein all of the symbols are as defined above) can be produced by subjecting a compound represented by general formula (IX):

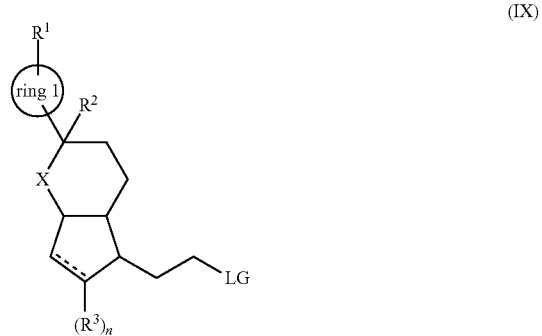

(IX)

(wherein all of the symbols are as defined above) and a compound represented by general formula (X):

HO—R$^4$  (X)

(wherein R$^4$ is as defined above) to the above-mentioned substitution reaction.

A compound represented by general formula (I) wherein E is —CH$_2$—, m in J is 0, Q is —O— and R$^4$ is a 3- to 15-membered ring, i.e., a compound represented by general formula (Ie):

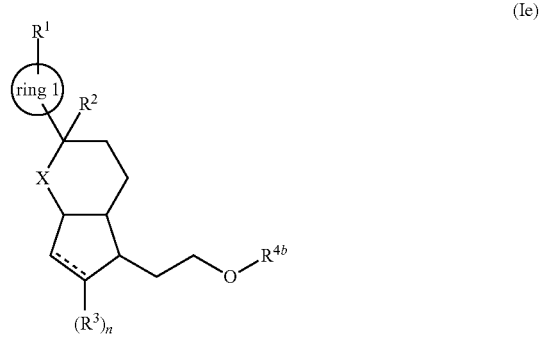

(Ie)

(wherein all of the symbols are as defined above)

can be produced by subjecting a compound represented by general formula (XI):

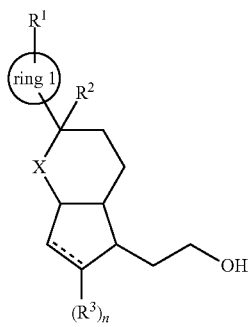

and a compound represented by general formula (V):

HO—R$^{4b}$ (V)

(wherein R$^{4b}$ is as defined above)
to the above-mentioned Mitsunobu reaction.

A compound wherein E is —CH$_2$—, m in J is 0 and Q is —S— can be produced by subjecting a compound represented by general formula (IV) or general formula (X) wherein the hydroxy group is —SH to the same reaction as mentioned above. A compound wherein E is —CH$_2$—, m in J is 0 and Q is —SO— or Q is —SO$_2$— can be produced by subjecting a compound wherein Q is —S— to the above-mentioned sulfur atom oxidation reaction.

A compound represented by general formula (I) wherein E is —CH$_2$—, m in J is 0 and Q is NH, i.e., a compound represented by general formula (If):

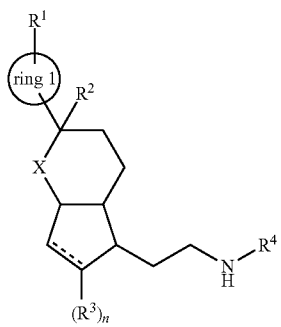

(wherein all of the symbols are as defined above)
can be produced by subjecting a compound represented by general formula (XII):

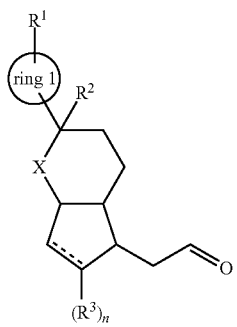

(wherein all of the symbols are as defined above)

and a compound represented by general formula (XIII):

H$_2$N—R$^4$ (XIII)

(wherein R$^4$ is as defined above)
to the above-mentioned reductive amination reaction.

In each of the above-mentioned reactions, the compounds that are used as starting raw materials are known or can be produced easily by known methods.

For example, among compounds represented by general formula (IV), a compound represented by general formula (IVa):

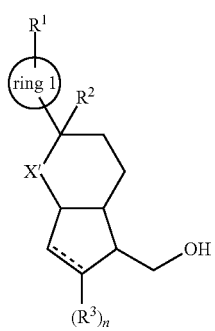

(wherein X' represents —O— or —NH—; and other symbols are as defined above)

can be produced in accordance with reaction scheme 1 shown below and optionally carrying out a protection/deprotection reaction.

<Reaction scheme 1>

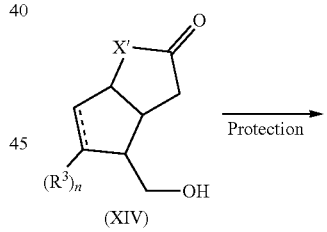

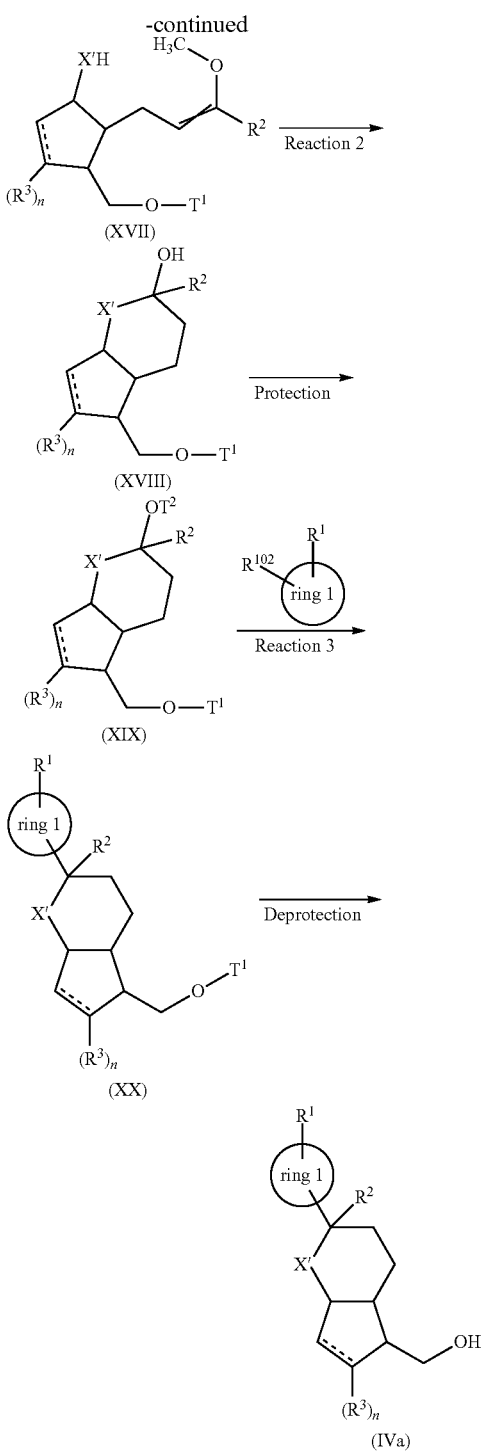

(wherein T$^1$ and T$^2$ represent different hydroxy group-protecting groups from each other; R$^{102}$ represents —ZnI, —ZnBr, —ZnCl, —MgI, —MgBr, —MgCl or —Li; and other symbols are as defined above).

In reaction scheme 1, the reduction reaction is known, and can be carried out, for example, at a temperature of −78 to 0° C. in an organic solvent (e.g., toluene, hexane, dichloromethane, tetrahydrofuran, 1,2-dimethoxyethane, diethyl ether, dioxane) using diisobutylaluminium hydride.

In reaction scheme 1, reaction 1 is known, and is carried out, for example, at a temperature of −78 to 50° C. in an organic solvent (e.g., dry toluene, dimethoxyethane, tetrahydrofuran) in the presence of a base (e.g., lithium hexamethyldisilazane (LHMDS), lithium diisopropylamide (LDA), butyllithium, potassium tert-butoxide, sodium hydride) using a Wittig reagent (e.g., (methoxymethyl)triphenylphosphonium chloride).

In reaction scheme 1, reaction 2 is known, and is carried out, for example, at a temperature of 0 to 100° C. in a solvent mixture of an organic solvent (e.g., dioxane, dry toluene, dimethoxyethane, tetrahydrofuran) and water using an acid (e.g., hydrochloric acid, acetic acid, paratoluenesulfonic acid).

In reaction scheme 1, reaction 3 is known, and is carried out, for example, at a temperature of −78 to 50° C. in an organic solvent (e.g., dioxane, dry toluene, dichloromethane, tetrahydrofuran) in the presence of a Lewis acid (e.g., aluminum chloride, tin chloride, a boron trifluoride-diethyl ether complex) using an organic metal reagent (e.g., 5-ethoxycarbonyl-2-furanyl zinc bromide).

In reaction scheme 1, the deprotection reaction is known, and can be carried out in the following manner.

Specific examples of the hydroxy group-protecting group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, and a 2, 2, 2-trichloroethoxycarbonyl (Troc) group.

The protecting group is not particularly limited, as long as the protecting group can be removed easily and selectively, in addition to the above protecting groups. For example, protecting groups described in P. G. M. Wuts, T. W. Greene, Greene's Protective Groups in Organic Synthesis, Wiley, Fourth Edition, New York, 2007 may be used.

The reaction of deprotection of the protecting group is well known, and includes the following reactions:
(1) hydrolysis under alkaline conditions;
(2) a deprotection reaction under acidic conditions;
(3) a deprotection reaction through hydrogenolysis;
(4) a deprotection reaction using a fluoride ion;
(5) a deprotection reaction using a metal; and
(6) a deprotection reaction using a metal complex.

These methods will be described concretely as follows.

The deprotection reaction through hydrolysis under alkaline conditions (1) is carried out, for example, at a temperature of 0 to 40° C. in an organic solvent (e.g. methanol, tetrahydrofuran, dioxane), using an alkali metal hydroxide (e.g. sodium hydroxide, potassium hydroxide, lithium hydroxide), an alkaline earth metal hydroxide (e.g. barium hydroxide, calcium hydroxide) or a carbonate (e.g. sodium carbonate, potassium carbonate) or an aqueous solution thereof or a mixture thereof.

The deprotection reaction under acidic conditions (2) is carried out, for example, at a temperature of 0 to 100° C. in an organic solvent (e.g. dichloromethane, chloroform, dioxane, ethyl acetate, anisole), using an organic acid (e.g. acetic acid, trifluoroacetic acid, methanesulfonic acid, p-tosylic acid) or an inorganic acid (e.g. hydrochloric acid, sulfuric acid) or a mixture thereof (e.g. hydrogen bromide/acetic acid).

The deprotection reaction through hydrogenolysis (3) is carried out, for example, at a temperature of 0 to 200° C. in a solvent (an ether-type solvent (e.g. tetrahydrofuran, dioxane, dimethoxyethane, diethyl ether), an alcohol-type solvent (e.g. methanol, ethanol), a benzene-type solvent (e.g. benzene, toluene), a ketone-type solvent (e.g. acetone, methyl ethyl ketone), a nitrile-type solvent (e.g. acetonitrile), an amide-type solvent (e.g. dimethylformamide), water, ethyl acetate, acetic acid or a solvent mixture of two or more of them) in the presence of a catalyst (e.g. palladium on carbon, palladium black, palladium hydroxide, platinum oxide or Raney-nickel) in a hydrogen atmosphere under an ordinary or elevated pressure or in the presence of ammonium formate.

The deprotection reaction using a fluoride ion (4) is carried out, for example, at a temperature of 0 to 40° C. in a water-miscible organic solvent (e.g., tetrahydrofuran, acetonitrile) using tetrabutylammonium fluoride.

The deprotection reaction using a metal (5) is carried out, for example, at a temperature of 0 to 40° C. in an acidic solvent (e.g., acetic acid, a buffered solution having a pH value of 4.2 to 7.2, a mixed solution of any one of these solutions with an organic solvent such as tetrahydrofuran) in the presence of powdery zinc optionally while applying ultrasonic waves.

The deprotection reaction using a metal complex (6) is carried out, for example, at a temperature of 0 to 40° C. in an organic solvent (e.g., dichloromethane, dimethylformamide, tetrahydrofuran, ethyl acetate, acetonitrile, dioxane, ethanol), water or a solvent mixture thereof in the presence of a trapping reagent (e.g., tributyltin hydride, triethylsilane, dimedone, morpholine, diethylamine, pyrrolidine), an organic acid (acetic acid, formic acid, 2-ethylhexanoic acid) and/or an organic acid salt (e.g., sodium 2-ethylhexanoate, potassium 2-ethylhexanoate), in the presence or absence of a phosphine-type reagent (triphenyl phosphine), using a metal complex (e.g., tetrakistriphenylphosphine palladium (0), bis(triphenylphosphine) palladium (II) dichloride, palladium (II) acetate, tris(triphenylphosphine) rhodium (I) chloride).

The deprotection reaction can also be carried out by, for example, the method described in P. G. M. Wuts, T. W. Greene, Green's Protective Groups in Organic Synthesis, Wiley, Fourth Edition, New York, 2007, in addition to the above-mentioned methods.

As will be apparent to those skilled in the art, the desired compound of the present invention can also be produced easily by properly selecting these deprotection reactions depending on the type of the desired compound.

Among the compounds represented by general formula (VI), a compound in which X is —O— or —NH— can be produced by subjecting the compound represented by general formula (IVa) to the below-mentioned oxidation reaction.

The oxidation reaction of a hydroxy group is known, and examples thereof include:
(1) a method employing Swern oxidation
(2) a method using a Dess-Martin reagent; and
(3) a method using a TEMPO reagent.

These methods will be described specifically as follows.

(1) The method employing Swern oxidation is carried out by, for example, reacting oxalyl chloride with dimethyl sulfoxide at −78° C. in an organic solvent (chloroform, dichloromethane, etc.), then reacting an alcohol compound in the resulting solution, and then reacting the resulting product with a tertiary amine (triethylamine, N,N-diisopropylethylamine, N-methylmorpholine, N-ethylpiperidine, diazabicyclo[5.4.0]undec-7-ene) at −78 to 20° C.

(2) The method using a Dess-Martin reagent is carried out, for example, at 0 to 40° C. in an organic solvent (chloroform, dichloromethane, 1,2-dichloroethane, tetrahydrofuran, acetonitrile, t-butyl alcohol, etc.) in the presence of a Dess-Martin reagent (1,1,1-triacetoxy-1,1-dihydro-1,2-benzoiodoxole-3-(1H)-one) in the presence or absence of a base (pyridine, etc.).

(3) The method using a TEMPO reagent is carried out, for example, at 20 to 60° C. in an organic solvent (chloroform, dichloromethane, tetrahydrofuran, toluene, acetonitrile, ethyl acetate, water, etc.) or a solvent mixture thereof, using a TEMPO reagent (2,2,6,6-tetramethyl-1-piperidinyloxy, a free radical) and a reoxidizing agent (aqueous hydrogen peroxide, sodium hypochlorite, 3-chloroperbenzoic acid, iodobenzene diacetate, potassium peroxymonosulfate (Oxone; trade name)) in the presence or absence of a quaternary ammonium salt (tetrabutylammonium chloride, tetrabutylammonium bromide, etc.), in the presence or absence of an inorganic salt (sodium bromide, potassium bromide, etc.), or in the presence or absence of an inorganic base (sodium hydrogen carbonate, sodium acetate, etc.).

Among the compounds represented by general formula (II), a compound in which X is —S— can be produced with adequately referring to the methods disclosed in International Publication No. 2012/102355 pamphlet and U.S. Pat. No. 4,367,237 and others. A compound in which X is —SO— or —SO$_2$— can be produced by subjecting the compound in which X is —S— to the above-mentioned sulfur atom oxidation reaction.

Among the compounds represented by general formula (IV), a compound in which ring 1 is an oxazole or thiazole ring, i.e., a compound represented by general formula (IVb):

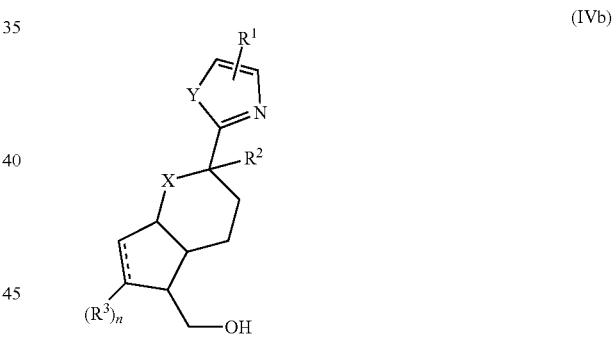

(IVb)

(wherein Y represents —O— or —S—; and other symbols are as defined above) can also be produced through reaction scheme 2 shown below.

<Reaction scheme 2>

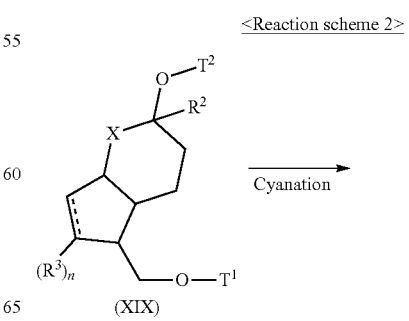

(XIX)

-continued

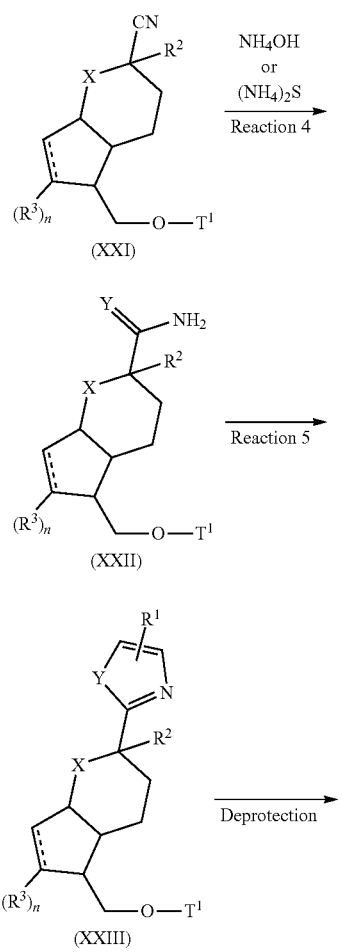

(wherein all of the symbols are as defined above)

In reaction scheme 2, the cyanation reaction is known, and can be carried out, for example, at a temperature of −78 to 25° C. in an organic solvent (e.g., dichloromethane, acetonitrile) in the presence of a Lewis acid (e.g., titanium chloride, iodotrimethylsilane, a boron trifluoride-diethyl ether complex) using a cyanation reagent (e.g., trimethylsilyl cyanide, sodium cyanide).

In reaction scheme 2, reaction 4 is known. With respect to a compound wherein Y is S, reaction 4 can be carried out, for example, at a temperature of 0 to 150° C. in an organic solvent (e.g., methanol, dioxane, N,N-dimethylformamide) in the presence of a base (e.g., pyridine, calcium hydride, sodium methoxide, triethylamine) or using a sulfurization reagent (e.g., hydrogen sulfide, ammonium sulfide, sodium sulfide). With respect to a compound wherein Y is O, reaction 4 can be carried out, for example, at a temperature of 0 to 100° C. in an organic solvent (e.g., methanol, dioxane, N,N-dimethylformamide) or a solvent mixture of the organic solvent with water, in the presence of a base (e.g., hydroxylamine, sodium hydroxide, potassium carbonate) or using an acid (sulfuric acid, hydrochloric acid).

In reaction scheme 2, reaction 5 is known, and can be carried out using an α-haloketone compound, for example, at a temperature of −78 to 50° C. in an organic solvent (e.g., dimethoxyethane, ethanol, N,N-dimethylformamide) in the presence of a base (e.g., sodium hydrogen carbonate, potassium carbonate, sodium hydrogen carbonate, pyridine) using ethyl bromopyruvate and a dehydration reagent (e.g., trifluoroacetic anhydride, trifluorosulfonic anhydride).

Among the compounds represented by general formula (XXI) in reaction scheme 2, a compound wherein $R^2$ is a C1-4 alkyl group can also be produced by subjecting a compound represented by general formula (XXI) wherein $R^2$ is a hydrogen atom to the below-mentioned reaction.

This reaction is known, and can be carried out, for example, at a temperature of −78 to 50° C. in an organic solvent (e.g., diethyl ether, tetrahydrofuran) in the presence of a base (e.g., lithium diisopropylamide, potassium hexamethyldisilazide) using an alkylating agent (e.g., methyl iodide, ethyl iodide).

Each of a compound represented by general formula (XI) and a compound represented by general formula (XII) can be produced in accordance with reaction scheme 3 using a compound represented by general formula (VI) optionally carrying out a protection/deprotection reaction.

<Reaction scheme 3>

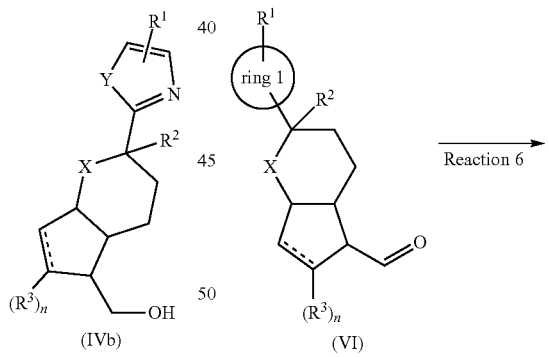

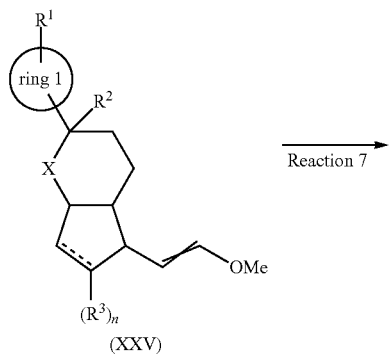

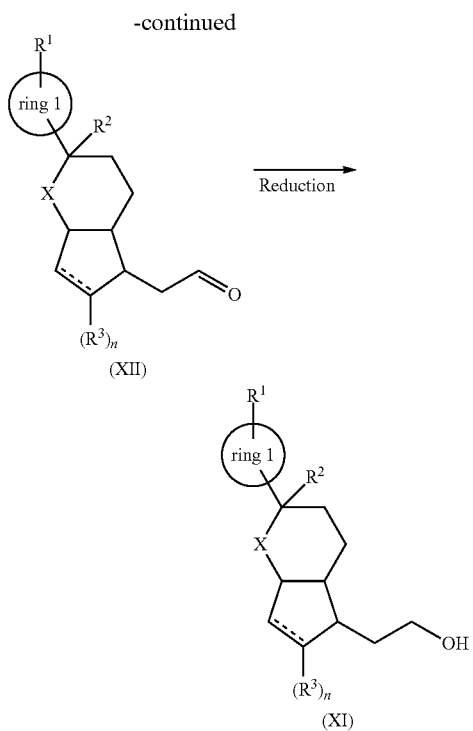

In reaction scheme 3, reaction 6 is known and can be carried out, for example, at a temperature of −78 to 50° C. in an organic solvent (e.g., dried toluene, dimethoxyethane, tetrahydrofuran) in the presence of a base (e.g., lithium hexamethyldisilazane (LHMDS), lithium diisopropylamide (LDA), butyl lithium, potassium tert-butoxide, sodium hydride) using a Wittig reagent (e.g., (methoxymethyl)triphenylphosphonium chloride).

In reaction scheme 3, reaction 7 is known and can be carried out, for example, by reacting an acid (e.g., p-toluenesulfonic acid, acetic acid) at a temperature of 0° C. to room temperature in a solvent mixture of an organic solvent (e.g., acetone, tetrahydrofuran, dioxane) with water.

In reaction scheme 3, the aldehyde group reduction reaction is known and can be carried out, for example, by reacting a reducing agent (e.g., sodium borohydride) at a temperature of 0° C. to room temperature in an organic solvent (tetrahydrofuran, methanol).

Each of a compound represented by general formula (II) and a compound represented by general formula (IX) can be produced by a known halogenation or sulfonylation method using a compound represented by general formula (IV) and a compound represented by general formula (XI).

The compound represented by general formula (III), general formula (V), general formula (VII), general formula (VIII), general formula (X), general formula (XIII) or general formula (XIV), the compounds which are used as other starting raw materials and reagents are known or can be produced easily by a combination of known methods such as the method described in Comprehensive Organic Transformations: A Guide to Functional Group Preparations, 2nd Edition (Richard C. Larock, John Wiley & Sons Inc, 1999) or the like.

In each of the reactions in the specification, each group may be protected when protection is required, and a compound adequately protected with a protecting group may be subjected to a known deprotection reaction.

In each of the reactions in the specification, a reaction involving heating can be carried out using a water bath, an oil bath or a sand bath or a microwave, as is obvious to persons skilled in the art.

In each of the reactions in the specification, a solid phase-supported reagent which is supported on a high-molecular-weight polymer (e.g., polystyrene, polyacrylamide, polypropylene, polyethylene glycol) may be used appropriately.

In each of the reactions in the specification, a reaction product can be purified by a normal purification means, for example, a method such as distillation under normal pressure or under reduced pressure, high performance liquid chromatography using silica gel or magnesium silicate, thin layer chromatography, an ion-exchange resin, a scavenger resin, or column chromatography or washing, recrystallization etc. The purification may be carried out after every reaction, or may be carried out after the completion of several reactions.

[Toxicity]

The compound according to the present invention has extremely low toxicity, and is safe enough to be used as a medicament. The toxicity can be evaluated by, for example, employing the following methods.

(1) Histopathological Test

A test compound (30 μL) which is prepared at each of various concentrations is dropwise applied to one eye of a male monkey (a cynomolgus monkey). After the repeated dropwise application for 4 weeks, the monkey is bled to death by cutting the caudal vena cava and the abdominal aorta under anesthesia with sodium thiopental (Ravonal (registered trade name), manufactured by Mitsubishi Tanabe Pharma Corporation), and then an eye ball is excised. The excised eye ball is fixed with a fixing solution (a phosphate buffer liquid containing 1% formaldehyde and 2.5% glutaraldehyde) to produce a specimen stained with haematoxylin and eosin. The specimen was subjected to a histopathological test.

(2) Ophthalmic Test

A solution (30 μL) containing a test compound which is prepared at each of various concentrations is dropwise applied to one eye of a male monkey (a cynomolgus monkey) at a single dose to a repeated dose for 4 weeks, and then the below-mentioned ophthalmic test is carried out. With respect to the procedures to be carried out under anesthesia, ketamine hydrochloride [a 0.1 to 0.4 mL/kg intramuscular injection of animal ketamine injection 5% "Fujita" (Fujita Pharmaceutical Co., Ltd.)] and xylazine hydrochloride [a 0.05 to 0.1 mL/kg intramuscular injection of Selactar (registered trade name) 2% (Bayer)] are used for anesthesia. With respect to the procedure to be carried out under mydriasis, a mydriatic agent (an eye drop: Mydrin (registered trade name) P, Santen Pharmaceutical Co., Ltd.) is used.

(2-1) Test with Laser Flare Cell Meter

After dropwise applications of a mydriatic agent to both eyes, an aqueous flare intensity (including the number of cells) is measured with a laser flare cell meter (FC-2000, Kowa Company, Ltd.) under anesthetized conditions. The cornea, crystalline lens and optic media are also observed with the laser flare cell meter in a slit lamp mode. During or after the test, physiological saline is sufficiently applied for the purpose of preventing the cornea from drying caused by ketamine.

(2-2) Measurement of Thickness of Cornea

An animal which is under anesthetized condition is fixed, an ophthalmic surface anesthetic agent (Benoxil (registered trade name) 0.4%, Santen Pharmaceutical Co., Ltd.) is dropwise applied, and then the thickness of the cornea is measured with an ultrasound diagnostic imaging and eye axial length/corneal thickness measurement device (US-4000 Echo scan, Nidek; simply referred to as "a corneal thickness measuring device", hereinbelow). During the measurement, physiological saline is dropwise applied at proper timing for the purpose of preventing the cornea from drying.

[Application to Drug]

The compound according to the present invention has an excellent EP2 agonist activity, and is therefore effective as a therapeutic agent for an EP2 receptor-related diseases, including immune diseases (autoimmune diseases such as amyotrophic lateral sclerosis, multiple sclerosis, Sjogren's syndrome, chronic rheumatoid arthritis and systemic lupus erythematosus; a rejection after organ transplantation, etc.), allergic diseases (e.g., bronchial asthma, allergic rhinitis, allergic conjunctivitis, atopic dermatitis, food allergy), neuronal death, dysmenorrhea, premature birth, miscarriage, baldness, ocular diseases (glaucoma, ocular hypertension, macular edema, macular degeneration, retina and optic nerve tensile force rise, myopia, hypermetropia, astigmatism, dry eye, retinal detachment, cataract, intraocular pressure rise, etc.), erectile dysfunction, arthritis, lung injury, pulmonary fibrosis, pulmonary emphysema, bronchitis, chronic obstructive pulmonary disease, liver injury, acute hepatitis, cirrhosis, shock, nephritis (acute nephritis, chronic nephritis, etc.), renal failure, cardiovascular diseases (hypertension, myocardial ischemia, chronic arterial occlusive disease, vibration disease, etc.), systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases (bone fracture, bone refracture, intractable bone fracture, bone nonunion, pseudarthrosis, osteomalacia, bone Paget's disease, ankylosing spondylitis, cancer bone metastasis, arthrosis deformans, and bone destruction in analogous diseases thereto, etc.), cartilage injury and others.

The compound according to the present invention may be administered as a combination drug which is combined with other surgical treatment and/or other drug for the purpose of (1) the complementation and/or enhancement of a therapeutic effect, (2) the improvement of pharmacokinetics/absorption of the compound according to the present invention and the reduction of the dose of the compound according to the present invention, and/or (3) the reduction of adverse side effects of the compound according to the present invention.

The combination drug of the compound according to the present invention with other drug may be administered in a form of a compounding agent in which both ingredients are incorporated into one preparation, or may take a form of administration of separate preparations. When administered by formulating into separate preparations, administration by simultaneous administration and time lag is included. In addition, in administration of time lag, the compound according to the present invention may be administered earlier, and other drug may be administered later, or other drug may be administered earlier, and the compound according to the present invention may be administered later. The method for administering a drug to be combined is not particularly limited, oral administration or parenteral administration may be employed.

The above-mentioned other drug may be a low-molecular-weight compound, or a high-molecular-weight protein, a polypeptide, a polynucleotide (DNA, RNA, a gene), an antisense, a decoy, an antibody, a vaccine or the like.

For example, when the compound according to the present invention is used as a therapeutic agent for cartilage injury, the compound may be used in combination with, for example, bone morphogenetic protein (BMP), steroidal drug, non-steroidal anti-inflammatory drug, hyaluronic acid preparation, prostaglandins, growth factors, vitamin D derivative, vitamin A derivative, metalloproteinase inhibitor, phosphodiesterase 4 (PDE4) inhibitor, elastase inhibitor, glycosaminoglycan preparation, NFκB decoy oligodeoxynucleotide, opioid analgesic drug, non-opioid analgesic drug, chondroitin sulfate or the like.

For example, when the compound according to the present invention is used as a therapeutic agent for glaucoma, the compound may be used in combination with, for example, a sympathetic nerve agonist (e.g., an $\alpha_2$ agonist such as apraclonidine hydrochloride, a $\beta_2$ agonist such as dipivefrine hydrochloride), a parasympathetic nerve agonist (e.g., pilocarpine hydrochloride, carbachol, demecarium, echothiophate or distigmine bromide), a sympathetic nerve suppressant (e.g., an $\alpha_1$ blocker such as bunazosin hydrochloride, a β blocker such as timolol maleate, befunolol hydrochloride, carteolol hydrochloride or betaxolol hydrochloride, an $\alpha_1\beta$ blocker such as levobunolol hydrochloride, nipradilol), a prostaglandin drug (e.g., isopropyl unoprostone, latanoprost, bimatoprost, travoprost, tafluprost, an EP2 agonist, an EP4 agonist, a DP agonist), a carbonic anhydrase inhibitor (e.g., acetazolamide, diclofenamide, methazolamide, dorzolamide hydrochloride, brinzolamide), a hyperosmotic drug (e.g., glycerin, a combination preparation of glycerin and fructose, isosorbide, D-mannitol), a ROCK (Rho kinase) inhibitor (e.g., Y-27632, ripasudil, AR-13324), an NMDA antagonist (e.g., ketamine hydrochloride, amantadine hydrochloride, memantine hydrochloride, dextromethorphan, methadone, ifenprodil tartrate) or the like.

In the combination, the weight ratio of the compound according to the present invention to the other drug is not particularly limited. With respect to the other drug, arbitrary two or more same types or different types of drugs may be used in combination.

The amount of the other drug for administration to be used in combination with the compound according to the present invention can be increased or decreased appropriately based on the clinically employed dose amount of the drug or an analogous drug thereof. The compounding ratio of the compound according to the present invention and the other drug can be controlled appropriately in consideration of the age and weight of a subject to be administered, the method of administration, the period of administration, the disease to be treated, symptom and the like. It is possible to combine 0.01 to 100 parts by weight of the other drug based on 1 part by weight of the compound according to the present invention. With respect to the other drug, multiple types of drugs may be used. In addition to the above-mentioned drugs, the other drug may be a drug having the same mechanism of action as those of the above-mentioned drugs. The other drug includes drugs which are so far discovered based on the below-mentioned mechanism, as well as drugs which will be discovered in the future.

The amount of the compound according to the present invention to be administered may vary depending on age, body weight, condition, therapeutic effect, the method of administration, the period of treatment and the like. Generally, the compound may be administered orally at a single dose of 1 mg to 300 mg once or several times per day per adult, or may be administered parenterally at a single dose of 0.1 mg to 150 mg once to several times per day per adult, or may be administered intravenously in a sustainable manner for 1 to 24 hours per day. Among parental administrations, particularly in the case of an eye drop, an eye drop having a concentration of preferably 0.000001 to 5% (w/v), more preferably 0.00001 to 0.05% (w/v) may be dropwise applied one to several drops per one time at a frequency of once to several times (e.g., once to eight times) per day. In the case of an eye ointment, an eye ointment having a concentration of preferably 0.000001 to 5% (w/w), more preferably 0.00001 to 0.05% (w/w) may be applied at a frequency of once to several times (e.g., once to four times) per day.

As mentioned above, the amount to be administered varies depending on various conditions. Therefore, an amount to be administered may be enough to be smaller than the above-mentioned amount to be administered, or an amount to be administered may be required to be larger than the above-mentioned amount to be administered.

When it is intended to use the compound of the present invention in the form of a single-component agent or a combination agent of the compound of the present invention with another medicinal agent for the purpose of the prevention and/or treatment of the above-mentioned diseases, the substance, which is an active ingredient, is formulated generally together with various kinds of additives or a pharmaceutically acceptable carrier such as a solvent and then the formulation is administered systemically or topically in an oral or parenteral dosage form. The term "pharmaceutically acceptable carrier" as used herein refers to a substance that can be generally used in the formulation of a medicine and is different from an active ingredient. The pharmaceutically acceptable carrier is preferably one which exhibits no pharmacological effect when a given amount of the preparation is administered, is unharmful, and does not interfere the therapeutic effect of an active ingredient. The pharmaceutically acceptable carrier can be used for the purpose of improving the usefulness of an active ingredient and the preparation, making the formulation of the preparation easy, stabilizing the quality of the preparation, improving the use of the preparation and others. More specifically, substances described in "Japanese Pharmaceutical Excipients Directory 2016" (published in 2016 by Yakuji Nippo Limited) (edited by International Pharmaceutical Excipients Council Japan) and the like may be selected appropriately depending on the intended use of the preparation.

Examples of the dosage form to be employed for administration include a preparation for oral administration (e.g., tablets, capsules, granules, a powder, a liquid or solution for oral administration, a syrup, a jerry for oral administration), a preparation for oro-mucosal application (e.g., tablets for oro-mucosal application, a spray for oro-mucosal application, a semi-solid preparation for oro-mucosal application, a preparation for gargles), a preparation for injection (e.g., an injection), a preparation for dialysis (e.g., a dialysis agent), a preparation for oral inhalation (e.g., an inhalation), a preparation for ophthalmic application (e.g., an ophthalmic preparation (eye drops), an ophthalmic ointment), a preparation for otic application (e.g., an ear preparation (ear drops)), a preparation for nasal application (e.g., a nasal preparation (nose drops)), a preparation for rectal application (e.g., a suppository, a semi-solid preparation for rectal application, an enema for rectal application), a preparation for vaginal application (e.g., tablets for vaginal use, a suppository for vaginal use), and a preparation for cutaneous application (e.g., a solid dosage form for cutaneous application, a liquid or solution for cutaneous application, a spray, an ointment, a cream, a gel, a patch).

EXAMPLES

Hereinbelow, the present invention will be described in detail with reference to examples. However, the present invention is not intended to be limited to these examples.

The solvents shown in parenthesis in the section of separation by chromatography and in TLC represent eluting solvents or developing solvents used, and the ratios are by volume.

NMR data are $^1$H-NMR data as measured at 300 MHz, unless otherwise specified.

The solvents in parentheses in the sections of NMR are solvents used for the measurements.

The compound names used herein are named using a computer program, ACD/Name Batch (registered trade name), which generally performs naming according to the rule of IUPAC, or in accordance with IUPAC nomenclature. For example, a compound represented by the following formula:

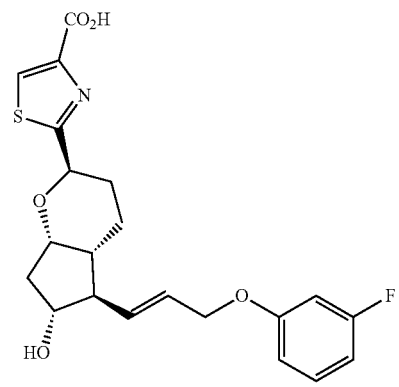 [SMILES: O=C(O)c1csc([C@H]2CC[C@@H]3[C@@H](/C=C/COc4cccc(F)c4)[C@H](O)C[C@@H]3O2)n1]

is named as
2-{(2R,4aR,5R,6R,7aS)-5-[(1E)-3-(3-fluorophenoxy)-1-propen-1-yl]-6-hydroxyoctahydrocyclopenta[b]pyran-2-yl}-1,3-thiazole-4-carboxylic acid.

LC-MS/ELSD was carried out under the following conditions.
[Column: Waters ACQUITY C18 (particle diameter: 1.7× $10^{-6}$ m; column length: 30×2.1 mm I.D.); flow rate: 1.0 mL/min; column temperature: 40° C.; mobile phase (A): a 0.1% aqueous formic acid solution; mobile phase (B): a 0.1% formic acid-acetonitrile solution; gradient (shown as "mobile phase (A):mobile phase (B) ratios"): [0 minute] 95:5; [0.1 minute] 95:5; [1.2 minutes] 5:95; [1.4 minutes] 5:95; [1.41 minutes] 95:5; [1.5 minutes] 95:5; detector: UV (PDA), ELSD, MS]

Production Examples

Reference Example 1

(3aR,4S,5R,6aS)-4-(((tert-Butyldiphenylsilyl)oxy)methyl)-5-((tetrahydro-2H-pyran-2-yl)oxy)hexahydro-2H-cyclopenta[b]furan-2-one (Reference Compound 1)

Under a nitrogen stream, N,N-dimethylformamide (2.1 L) and imidazole (183 g) were added to (3aR,4S,5R,6aS)-4-

(hydroxymethyl)-5-((tetrahydro-2H-pyran-2-yl)oxy)hexahydro-2H-cyclopenta[b]furan-2-one (CAS No. 69222-61-3) (458 g), and then tert-butyldiphenylchlorosilane (541 g) was added dropwise to the resultant solution under ice cooling. The resultant solution was stirred at room temperature for 1 hour, then ethanol (57 mL) was added to the reaction solution, and then the resultant solution was stirred for 30 minutes. Methyl tert-butyl ether and 0.5N hydrochloric acid were added to the reaction solution. An organic layer was washed with water and saturated saline, was then dried over anhydrous sodium sulfate and was then filtered. A filtrate was concentrated under a reduced pressure to produce the title compound having a physical property value shown below. The compound thus produced was used in the subsequent reaction without purification.

TLC: Rf 0.45 (hexane:ethyl acetate=2:1).

Reference Example 2

(3aR,4S,5R,6aS)-4-(((tert-Butyldiphenylsilyl)oxy) methyl)-5-((tetrahydro-2H-pyran-2-yl)oxy)hexahydro-2H-cyclopenta[b]furan-2-ol (Reference Compound 2)

Under a nitrogen stream, toluene (1.5 L) was added to Reference Compound 1 (463 g), the resultant solution was cooled with dry ice/methanol, and then 1.00 M diisobutylaluminum hydride/toluene (995 mL) was added dropwise to the resultant solution. The reaction solution was stirred at the same temperature for 1 hour, and then a solution of potassium sodium L-tartrate (434 g) in water (600 mL) was added dropwise thereto. The resultant solution was stirred overnight at room temperature, and then methyl tert-butyl ether (500 mL) and water (500 mL) were added to the reaction solution. An organic layer was washed with water and saturated saline, was then dried over anhydrous sodium sulfate and was then filtered. A filtrate was concentrated under a reduced pressure to produce the title compound having a physical property value shown below. The compound thus produced was used in the subsequent reaction without purification.

TLC: Rf 0.25 (hexane:ethyl acetate=2:1).

Reference Example 3

(1S,2R,3S,4R)-3-(((tert-Butyldiphenylsilyl)oxy) methyl)-2-(3-methoxyallyl)-4-((tetrahydro-2H-pyran-2-yl)oxy)cyclopentanol (Reference Compound 3)

Under a nitrogen stream, tetrahydrofuran (2.3 L) was added to 85% potassium tert-butoxide (298 g), and then (methoxymethyl)triphenylphosphonium chloride (775 g) was added thereto under ice cooling. The resultant solution was stirred for 30 minutes under ice cooling, and then a solution of Reference Compound 2 (488 g) in tetrahydrofuran (600 mL) was added dropwise thereto. The resultant solution was stirred for 30 minutes under ice cooling, and then water (100 mL) was added dropwise to the reaction solution. Water and saturated saline were added to the reaction solution, and the resultant solution was extracted with ethyl acetate. An organic layer was washed with saturated saline, was then dried over anhydrous sodium sulfate and was then filtered. A filtrate was concentrated under a reduced pressure, then diisopropyl ether (400 mL) and hexane (400 mL) were added to a residue (1100 g), then the resultant solution was filtered, and then a filtrate was concentrated under a reduced pressure. A residue was purified by silica gel column chromatography (hexane:ethyl acetate=1:0→10:1→5:1→2:1) to produce the title compound (418 g) having the following physical property value.

TLC: Rf 0.45 (hexane:ethyl acetate=2:1).

Reference Example 4

(4aR,5S,6R,7aS)-5-(((tert-Butyldiphenylsilyl)oxy) methyl)octahydrocyclopenta[b]pyran-2,6-diol (Reference Compound 4)

Under a nitrogen stream, tetrahydrofuran (600 mL), water (600 mL) and acetic acid (1.2 L) were added to Reference Compound 3 (418 g), and the resultant solution was stirred at an internal temperature of 55° C. for 3 hours. The reaction solution was cooled to room temperature, and then toluene (1.5 L) and saturated saline (400 mL) were added thereto. An organic layer was washed with water, a saturated aqueous sodium hydrogen carbonate solution and saturated saline, was then dried over anhydrous sodium sulfate and was then filtered, and a filtrate was concentrated under a reduced pressure. A residue was purified by silica gel column chromatography (hexane:ethyl acetate=1:0→4:1→2:1→1:3) to produce the title compound (229 g) having the following physical property value.

TLC: Rf 0.20 (hexane:ethyl acetate=1:1).

Reference Example 5

(4aR,5S,6R,7aS)-5-(((tert-Butyldiphenylsilyl)oxy) methyl)octahydrocyclopenta[b]pyran-2,6-diyl diacetate (Reference Compound 5)

Under a nitrogen stream, pyridine (900 mL) was added to Reference Compound 4 (229 g), and acetic anhydride (182 g) was added dropwise to the resultant solution over 10 minutes under ice cooling. The resultant solution was stirred overnight at room temperature, and then the reaction solution was poured into a solution composed of toluene (500 mL), water (1.2 L) and ice (600 g) to terminate the reaction. The reaction solution was extracted with toluene, then an organic layer was washed with water, 1 N hydrochloric acid, a saturated aqueous sodium hydrogen carbonate solution and saturated saline, was then dried over anhydrous sodium sulfate, and was then filtered. A filtrate was concentrated under a reduced pressure to produce the title compound having a physical property value shown below. The compound thus produced was used in the subsequent reaction without purification.

TLC: Rf 0.25 (hexane:ethyl acetate=4:1).

Reference Example 6

(2R,4aR,5S,6R,7aS)-5-(((tert-Butyldiphenylsilyl) oxy)methyl)-2-cyano octahydrocyclopenta[b]pyran-6-yl acetate (Reference Compound 6)

Under a nitrogen stream, anhydrous acetonitrile (1.4 L) and 96%-trimethylsilyl cyanide (91.9 g) were added to Reference Compound 5 (268 g), and then 1 M tin tetrachloride/dichloromethane (494 mL) was added dropwise thereto under ice cooling. The resultant solution was stirred for 40 minutes under ice cooling, and then the reaction solution was poured into a solution composed of sodium hydrogen carbonate (468 g), ice (600 g) and water (600 mL) to terminate the reaction. Water and ethyl acetate were added to the mixed solution, then the resultant solution was extracted, and then an aqueous layer was extracted with ethyl acetate/hexane (1:1). An organic layer was washed with water and saturated saline and was then dried over anhydrous sodium sulfate, and then the resultant solution was filtered. A filtrate was concentrated under a reduced pressure to produce the title compound having a physical property value shown below. The compound thus produced was used in the subsequent reaction without purification.

TLC: Rf 0.35 (hexane:ethyl acetate=4:1).

Reference Example 7

(2R,4aR,5S,6R,7aS)-5-(((tert-Butyldiphenylsilyl)oxy)methyl)-2-carbamothioyloctahydrocyclopenta[b]pyran-6-yl acetate (Reference Compound 7)

Pyridine (1.2 L) was added to Reference Compound 6 (238 g), then a 20% ammonium sulfide solution (490 g) was added dropwise to the resultant solution under ice cooling, and then the resultant solution was stirred at a temperature of 10° C. or lower for 24 hours. Ice (300 g) and water (2.0 L) were added to the reaction solution, and the resultant solution was extracted with toluene. An organic layer was washed with water and saturated saline, was then dried over anhydrous sodium sulfate, and was then filtered. A filtrate was concentrated under a reduced pressure, and the resultant product was distilled azeotropically three times with toluene (500 mL) to produce a concentrated residue. The residue was purified by silica gel column chromatography (hexane:ethyl acetate=9:1→5:1→4:1→3:1→2:1) to produce the title compound (95.4 g) having the following physical property value.

TLC: Rf 0.30 (hexane:ethyl acetate=2:1).

Reference Example 8: Ethyl 2-((2R,4aR,5S,6R,7aS)-6-acetoxy-5-(((tert-butyldiphenylsilyl)oxy)methyDoctahydrocyclopenta[b]pyran-2-yl)thiazole-4-carboxylate (Reference Compound 8)

Under a nitrogen stream, a solution (1.1 L) of Reference Compound 7 (145 g) in dimethoxyethane was cooled with dry ice/methanol, and then potassium hydrogen carbonate (202 g) was added thereto. 90% Ethyl bromopyruvate (164 g) was added dropwise to the reaction solution, and then the resultant solution was stirred for 4 hours. Pyridine (160 g) was added to the reaction solution, then trifluoroacetic anhydride (212 g) was added dropwise to the resultant solution, then the reaction solution was stirred for 30 minutes, and then water (600 mL) was added to the resultant solution. The reaction solution was heated to room temperature and was then extracted with ethyl acetate. An organic layer was washed with water and saturated saline and was then dried over anhydrous sodium sulfate, then the resultant solution was filtered, and a filtrate was concentrated under a reduced pressure. A residue was purified by silica gel column chromatography (hexane:ethyl acetate=1:0→10:1→6:1→4:1→3:1) to produce the title compound (156 g) having the following physical property value. TLC: Rf 0.45 (hexane:ethyl acetate=2:1).

Reference Example 9: Ethyl 2-((2R,4aR,5S,6R,7aS)-6-acetoxy-5-(hydroxymethyl)octahydrocyclopenta[b]pyran-2-yl) thiazole-4-carboxylate (Reference Compound 9)

Under a nitrogen stream, tetrahydrofuran (370 mL) and acetic acid (38.5 g) were added to Reference Compound 8 (156 g), and then 1M tetra-n-butylammonium fluoride/tetrahydrofuran (642 mL) was added dropwise to the resultant solution. The solution was stirred at an internal temperature of 44° C. for two hours and was then cooled to room temperature, and then a saturated aqueous sodium hydrogen carbonate solution (600 mL) was added to the reaction solution. Water was added to the mixed solution, and then the resultant solution was extracted with ethyl acetate. An organic layer was washed with water and saturated saline, and the resultant solution was dried over anhydrous sodium sulfate and was then filtered. A filtrate was concentrated under a reduced pressure, and then a residue was purified by silica gel column chromatography (hexane:ethyl acetate=1:1→1:2) to produce the title compound (80.1 g) having the following physical property value.

TLC: Rf 0.20 (hexane:ethyl acetate=2:3).

Reference Example 10: Ethyl

2-[(2R,4aR,5R,6R,7aS)-6-(acetyloxy)-5-formyloctahydrocyclopenta[b]pyran-2-yl]-1,3-thiazole-4-carboxylate (Reference Compound 10)

Under an argon stream, a Dess-Martin reagent (299 mg) was added to a solution (4.0 mL) of Reference Compound 9 (200 mg) in dichloromethane at 0° C., and then the resultant solution was stirred at room temperature for 1 hour. A saturated aqueous sodium sulfite solution was added to the reaction solution, and then the resultant solution was extracted with ethyl acetate. An organic layer was washed with a saturated aqueous sodium hydrogen carbonate solution, water and saline, and the resultant solution was dried over anhydrous sodium sulfate and was then concentrated under a reduced pressure to produce the title compound (280 mg) having the following physical property value.

TLC: Rf 0.56 (hexane:ethyl acetate=1:2).

Reference Example 11

5-[(2-{[tert-Butyl(dimethyl)silyl]oxy}ethyl)sulfanyl]-1-phenyl-1H-tetrazole (Reference Compound 11)

Under an argon stream, acetone (40 mL), 1-phenyl-1H-tetrazole-5-thiol (68.6 g) and potassium carbonate (5.07 g) were added to (2-bromomethoxy)-tert-butyldimethylsilane (8.37 g), and the resultant solution was stirred at room temperature for 16 hours. Water was added to the reaction solution, and the resultant solution was extracted with ethyl acetate. An organic layer was washed with saturated saline and was then dried over anhydrous sodium sulfate, and then the resultant solution was concentrated under a reduced pressure to produce the title compound (14.0 g) having the following physical property value. The compound thus produced was used in the subsequent reaction without purification.

TLC: Rf 0.48 (hexane:ethyl acetate=9:1).

Reference Example 12

5-[(2-{[tert-Butyl(dimethyl)silyl]oxy}ethyl)sulfonyl]-1-phenyl-1H-tetrazole (Reference Compound 12)

Into a reaction vessel were added toluene (45 mL), 30% aqueous hydrogen peroxide (9.92 g), sodium tungstate dihydrate (115 mg) and trioctylmethylammonium chloride (141 mg). The resultant solution was stirred at room temperature for 20 minutes. A solution (18 mL) of Reference Compound 11 (14.0 g) in toluene was added dropwise to the reaction solution, and the resultant solution was stirred at 50° C. for 2 hours. The reaction solution was extracted with ethyl acetate, and then an organic layer was washed with saturated saline. The organic layer was dried over anhydrous sodium sulfate and was then concentrated under a reduced pressure. A residue thus produced was purified by silica gel column chromatography (hexane:ethyl acetate=9:1→1:1) to produce the title compound (12.1 g) having the following physical property value.

TLC: Rf 0.17 (hexane:ethyl acetate=9:1).

Reference Example 13: Ethyl 2-{(2R,4aR,5R,6R,7aS)-6-(acetyloxy)-5-[(1E)-3-{[tert-butyl(dimethyl)silyl]oxy}prop-1-en-1-yl]octahydrocyclopenta[b]pyran-2-yl}-1,3-thiazole-4-carboxylate (Reference Compound 13)

Under an argon stream, 1,2-dimethoxyethane (76 mL) and Reference Compound 12 (5.62 g) were added to Reference Compound 10 (2.82 g), and the resultant solution was stirred at −60° C. 0.5 M Lithium hexamethyldisilazide/toluene (22.9 mL) was added dropwise to the reaction solution, and the resultant solution was stirred at −60° C. for 40 minutes. A saturated aqueous ammonium chloride solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=7:1→5:1) to produce the title compound (1.48 g) having the following physical property value.

TLC: Rf 0.60 (hexane:ethyl acetate=2:1).

Reference Example 14: Ethyl 2-{(2R,4aR,5R,6R,7aS)-6-(acetyloxy)-5-[(1E)-3-hydroxy prop-1-en-1-yl]octahydrocyclopenta[b]pyran-2-yl}-1,3-thiazole-4-carboxylate (Reference Compound 14)

The same procedure as in Reference Example 9 was carried out using Reference Compound 13 to produce the title compound having the following physical property value.

TLC: Rf 0.66 (ethyl acetate).

Reference Example 15: Ethyl 2-{(2R,4aR,5R,6R,7aS)-6-(acetyloxy)-5-[(1E)-3-(3-fluorophenoxy)prop-1-en-1-yl]octahydrocyclopenta[b]pyran-2-yl}-1,3-thiazole-4-carboxylate (Reference Compound 15)

Under an argon stream, tetrahydrofuran (250 μL), N,N,N',N'-tetramethylazodicarboxamide (26 mg) and 3-fluorophenol (38 mg) were added to Reference Compound 14 (30 mg), and the resultant solution was stirred at room temperature. Tributylphosphine (37 μL) was added dropwise to the reaction solution, and the resultant solution was stirred at room temperature for 2 hours. N,N,N',N'-Tetramethylazodicarboxamide (26 mg) and tributylphosphine (37 μL) were added to the reaction solution, and the resultant solution was stirred for 1 hour. The reaction solution was concentrated under a reduced pressure, and a residue was purified by silica gel column chromatography (hexane:ethyl acetate=9:1→1:1) to produce the title compound (31 mg) having the following physical property value.

TLC: Rf 0.79 (hexane:ethyl acetate=1:2).

Example 1

2-{(2R,4aR,5R,6R,7aS)-5-[(1E)-3-(3-Fluorophenoxy)-1-propen-1-yl]-6-hydroxyoctahydrocyclopenta[b]pyran-2-yl}-1,3-thiazole-4-carboxylic acid (Compound 1)

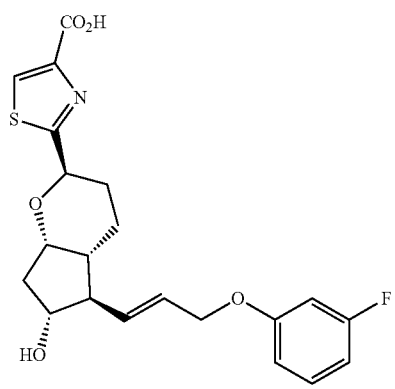 [SMILES: O=C(O)c1csc([C@H]2CC[C@@H]3[C@@H](/C=C/COc4cccc(F)c4)[C@H](O)C[C@@H]3O2)n1]

Methanol (1.0 mL) and a 2.0 M aqueous sodium hydroxide solution (0.20 mL) were added to Reference Compound 15 (31 mg), and the resultant solution was stirred at room temperature. AG50W-X8 resin (a product name) (200 mg) was added to the reaction solution, and the resultant solution was stirred at room temperature for 30 minutes. The reaction solution was filtered, and a filtrate was concentrated under a reduced pressure to produce a compound of the present invention (18.1 mg) having the following physical property values.

TLC: Rf 0.47 (dichloromethane:methanol:acetic acid=90:10:1);

$^1$H-NMR (CDCl$_3$): δ8.29, 7.19, 6.70-6.35, 5.83, 5.70, 5.19, 4.50, 4.13, 4.00, 2.69, 2.34-2.29, 1.94, 1.85, 1.68, 1.59.

Examples 2-1 to 2-23

The same procedures as in Reference Example 11→Reference Example 12→Reference Example 13→Reference Example 9→Reference Example 15→Example 1 were carried out, except that a corresponding bromo compound was used in place of (2-bromomethoxy)-tert-butyldimethylsilane and a corresponding phenol compound was used in place of 3-fluorophenol. In this manner, the following compounds were produced.

Example 2-1

2-{(2R,4aR,5R,6R,7aS)-6-Hydroxy-5-[(1E)-5-(4-methoxyphenoxy)-1-penten-1-yl]octahydrocyclopenta[b]pyran-2-yl}-1,3-thiazole-4-carboxylic acid (Compound 2-1)

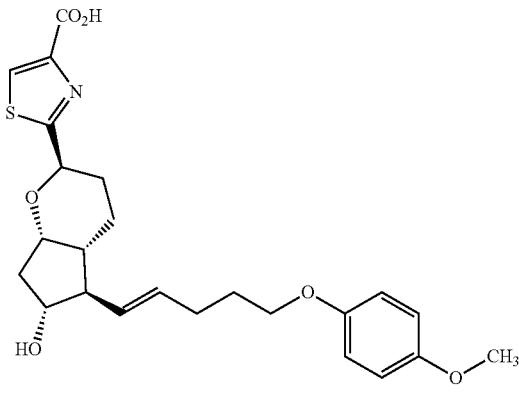 [SMILES: COc1ccc(OCCC/C=C/[C@@H]2[C@H]3CC[C@H](c4nc(C(=O)O)cs4)O[C@H]3C[C@H]2O)cc1]

TLC: Rf 0.47 (dichloromethane:methanol:acetic acid=90:10:1);
$^1$H-NMR (CDCl$_3$): δ8.12, 6.85, 6.80, 5.54, 5.27, 5.10, 4.09, 3.94-3.80, 3.91, 3.76, 2.46, 2.30-2.15, 2.05, 1.95-1.73, 1.53, 1.36, 1.26.

Example 2-2

2-{(2R,4aR,5R,6R,7aS)-6-Hydroxy-5-[(1E)-4-phenoxy-1-buten-1-yl]octahydrocyclopenta[b]pyran-2-yl}-1,3-thiazole-4-carboxylic acid (Compound 2-2)

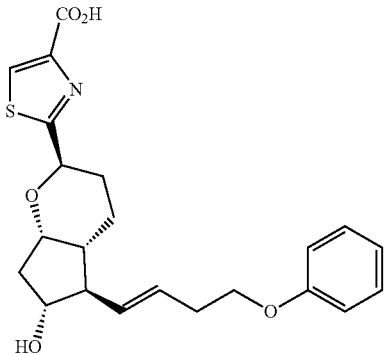 [SMILES: O=C(O)c1csc([C@H]2CC[C@@H]3[C@@H](/C=C/CCOc4ccccc4)[C@H](O)C[C@@H]3O2)n1]

TLC: Rf 0.42 (dichloromethane:methanol:acetic acid=60:10:1);
$^1$H-NMR (CDCl$_3$): δ8.30, 7.27, 6.93, 6.88, 5.66, 5.41, 5.17, 4.13, 4.00, 3.92, 2.65-2.50, 2.36-2.19, 1.92, 1.82, 1.63.

Example 2-3

2-{(2R,4aR,5R,6R,7aS)-6-Hydroxy-5-[(1E)-3-phenoxy-1-propen-1-yl]octahydrocyclopenta[b]pyran-2-yl}-1,3-thiazole-4-carboxylic acid (Compound 2-3)

TLC: Rf 0.10 (dichloromethane:methanol:water=90:10:1);
$^1$H-NMR (CDCl$_3$): δ8.31, 7.29, 6.93, 5.87, 5.70, 5.19, 4.54, 4.13, 4.00, 2.69, 2.31, 2.26, 1.95, 1.85, 1.69-1.58.

Example 2-4

2-{(2R,4aR,5R,6R,7aS)-6-Hydroxy-5-[(1E)-5-phenoxy-1-penten-1-yl]octahydrocyclopenta[b]pyran-2-yl}-1,3-thiazole-4-carboxylic acid (Compound 2-4)

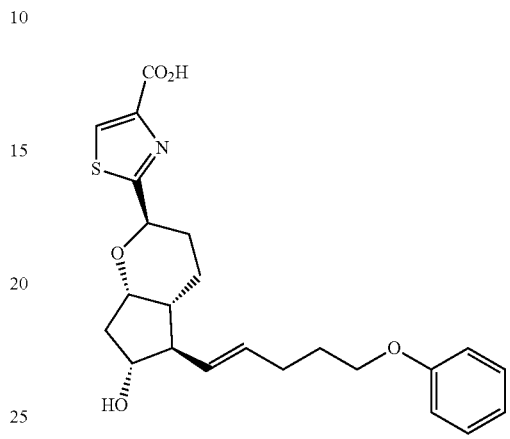

TLC: Rf 0.13 (dichloromethane:methanol:water=90:10:1);
$^1$H-NMR (CDCl$_3$): δ8.29, 7.27, 6.92, 6.88, 5.62, 5.30, 5.17, 4.13-4.08, 3.97, 3.92-3.86, 2.61-2.51, 2.32-2.19, 1.92-1.85, 1.83-1.76, 1.59-1.28.

Example 2-5

2-{(2R,4aR,5R,6R,7aS)-5-[(1E)-3-(2-Fluorophenoxy)-1-propen-1-yl]-6-hydroxyoctahydrocyclopenta[b]pyran-2-yl}-1,3-thiazole-4-carboxylic acid (Compound 2-5)

LC-MS/ELSD retention time: 0.81 minute;
MASS (ESI, Pos.): 420 (M+H)$^+$;
$^1$H-NMR (CDCl$_3$): δ8.29, 7.11-6.86, 5.86, 5.70, 5.18, 4.59, 4.12, 3.99, 2.70, 2.30, 2.24, 1.92, 1.84, 1.70-1.54.

Example 2-6

2-{(2R,4aR,5R,6R,7aS)-5-[(1E)-3-(4-Fluorophenoxy)-1-propen-1-yl]-6-hydroxyoctahydrocyclopenta[b]pyran-2-yl}-1,3-thiazole-4-carboxylic acid (Compound 2-6)

LC-MS/ELSD retention time: 0.82 minute;
MASS (ESI, Pos.): 420 (M+H)$^+$;
$^1$H-NMR (CDCl$_3$): δ8.31, 6.97, 6.84, 5.84, 5.69, 5.19, 4.48, 4.13, 3.98, 2.69, 2.39, 2.29, 1.95, 1.84, 1.71-1.57.

Example 2-7

2-{(2R,4aR,5R,6R,7aS)-6-Hydroxy-5-[(1E)-3-(2-methylphenoxy)-1-propen-1-yl]octahydrocyclopenta[b]pyran-2-yl}-1,3-thiazole-4-carboxylic acid (Compound 2-7)

LC-MS/ELSD retention time: 0.86 minute;
MASS (ESI, Pos.): 416 (M+H)$^+$;

¹H-NMR (CDCl₃): δ8.29, 7.12, 6.86, 6.80, 5.86, 5.68, 5.19, 4.53, 4.13, 3.99, 2.68, 2.35-2.19, 2.24, 1.94, 1.84, 1.71-1.59.

Example 2-8

2-{(2R,4aR,5R,6R,7aS)-6-Hydroxy-5-[(1E)-3-(3-methylphenoxy)-1-propen-1-yl]octahydrocyclopenta[b]pyran-2-yl}-1,3-thiazole-4-carboxylic acid (Compound 2-8)

LC-MS/ELSD retention time: 0.86 minute;
MASS (ESI, Pos.): 416 (M+H)⁺;
¹H-NMR (CDCl₃): δ8.30, 7.16, 6.77, 6.73, 6.71, 5.86, 5.69, 5.19, 4.51, 4.13, 3.96, 2.68, 2.33, 2.30-2.19, 1.94, 1.83, 1.71-1.59.

Example 2-9

2-{(2R,4aR,5R,6R,7aS)-6-Hydroxy-5-[(1E)-3-(4-methylphenoxy)-1-propen-1-yl]octahydrocyclopenta[b]pyran-2-yl}-1,3-thiazole-4-carboxylic acid (Compound 2-9)

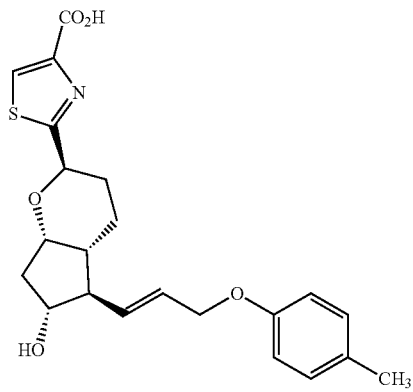 [SMILES: Cc1ccc(OC/C=C/[C@@H]2[C@H]3CC[C@H](c4nc(C(=O)O)cs4)O[C@H]3C[C@H]2O)cc1]

LC-MS/ELSD retention time: 0.86 minute;
MASS (ESI, Pos.): 416 (M+H)⁺;
¹H-NMR (CDCl₃): δ8.30, 7.07, 6.80, 5.85, 5.69, 5.19, 4.50, 4.13, 3.99, 2.69, 2.34-2.21, 2.29, 1.95, 1.84, 1.71-1.56.

Example 2-10

2-{(2R,4aR,5R,6R,7aS)-5-[(1E)-3-(2-Chlorophenoxy)-1-propen-1-yl]-6-hydroxyoctahydrocyclopenta[b]pyran-2-yl}-1,3-thiazole-4-carboxylic acid (Compound 2-10)

LC-MS/ELSD retention time: 0.86 minute;
MASS (ESI, Pos.): 436 (M+H)⁺;
¹H-NMR (CDCl₃): δ8.29, 7.36, 7.16, 6.93-6.87, 5.87, 5.73, 5.18, 4.60, 4.13, 3.98, 2.69, 2.34-2.19, 1.94, 1.83, 1.70-1.56.

Example 2-11

2-{(2R,4aR,5R,6R,7aS)-5-[(1E)-3-(3-Chlorophenoxy)-1-propen-1-yl]-6-hydroxyoctahydrocyclopenta[b]pyran-2-yl}-1,3-thiazole-4-carboxylic acid (Compound 2-11)

LC-MS/ELSD retention time: 0.88 minute;
MASS (ESI, Pos.): 436 (M+H)⁺;
¹H-NMR (CDCl₃): δ8.30, 7.19, 6.93, 6.80, 5.84, 5.70, 5.19, 4.51, 4.13, 4.00, 2.70, 2.35-2.21, 1.95, 1.85, 1.66, 1.60.

Example 2-12

2-{(2R,4aR,5R,6R,7aS)-5-[(1E)-3-(4-Chlorophenoxy)-1-propen-1-yl]-6-hydroxyoctahydrocyclopenta[b]pyran-2-yl}-1,3-thiazole-4-carboxylic acid (Compound 2-12)

LC-MS/ELSD retention time: 0.88 minute;
MASS (ESI, Pos.): 436 (M+H)⁺;
¹H-NMR (CDCl₃): δ8.30, 7.23, 6.82, 5.84, 5.69, 5.19, 4.49, 4.13, 3.98, 2.70, 2.34-2.19, 1.94, 1.84, 1.69-1.58.

Example 2-13

2-[(2R,4aR,5R,6R,7aS)-6-Hydroxy-5-{(1E)-3-[2-(trifluoromethoxy)phenoxy]-1-propen-1-yl}octahydrocyclopenta[b]pyran-2-yl]-1,3-thiazole-4-carboxylic acid (Compound 2-13)

LC-MS/ELSD retention time: 0.90 minute;
MASS (ESI, Pos.): 486 (M+H)⁺;
¹H-NMR (CDCl₃): δ8.30, 7.22, 6.99, 6.93, 5.84, 5.70, 5.18, 4.59, 4.12, 3.90, 2.70, 2.34-2.19, 1.94, 1.82, 1.69-1.54.

Example 2-14

2-[(2R,4aR,5R,6R,7aS)-6-Hydroxy-5-{(1E)-3-[3-(trifluoromethoxy)phenoxy]-1-propen-1-yl}octahydrocyclopenta[b]pyran-2-yl]-1,3-thiazole-4-carboxylic acid (Compound 2-14)

LC-MS/ELSD retention time: 0.93 minute;
MASS (ESI, Pos.): 486 (M+H)⁺;
¹H-NMR (CDCl₃): δ8.29, 7.27, 6.83, 6.77, 5.84, 5.70, 5.19, 4.52, 4.13, 3.99, 2.70, 2.34-2.21, 1.96, 1.85, 1.71-1.56.

Example 2-15

2-[(2R,4aR,5R,6R,7aS)-6-Hydroxy-5-{(1E)-3-[4-(trifluoromethoxy)phenoxy]-1-propen-1-yl}octahydrocyclopenta[b]pyran-2-yl]-1,3-thiazole-4-carboxylic acid (Compound 2-15)

LC-MS/ELSD retention time: 0.93 minute;
MASS (ESI, Pos.): 486 (M+H)⁺;
¹H-NMR (CDCl₃): δ8.31, 7.14, 6.89, 5.85, 5.70, 5.19, 4.51, 4.14, 4.00, 2.70, 2.35-2.20, 1.96, 1.85, 1.71-1.57.

Example 2-16

2-[(2R,4aR,5R,6R,7aS)-6-Hydroxy-5-{(1E)-3-[2-(trifluoromethyl)phenoxy]-1-propen-1-yl}octahydrocyclopenta[b]pyran-2-yl]-1,3-thiazole-4-carboxylic acid (Compound 2-16)

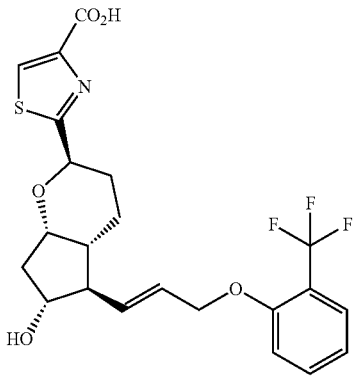 [SMILES: O=C(O)c1csc([C@H]2CC[C@@H]3[C@@H](/C=C/COc4ccccc4C(F)(F)F)[C@H](O)C[C@@H]3O2)n1]

LC-MS/ELSD retention time: 0.89 minute;
MASS (ESI, Pos.): 470 (M+H)$^+$;
$^1$H-NMR (CDCl$_3$): δ8.29, 7.54, 7.45, 7.01, 6.98, 5.83, 5.73, 5.18, 4.63, 4.13, 4.00, 2.68, 2.37-2.18, 1.95, 1.85, 1.70-1.54.

Example 2-17

2-[(2R,4aR,5R,6R,7aS)-6-Hydroxy-5-{(1E)-3-[3-(trifluoromethyl)phenoxy]-1-propen-1-yl}octahydrocyclopenta[b]pyran-2-yl]-1,3-thiazole-4-carboxylic acid (Compound 2-17)

LC-MS/ELSD retention time: 0.90 minute;
MASS (ESI, Pos.): 470 (M+H)$^+$;
$^1$H-NMR (CDCl$_3$): δ8.30, 7.38, 7.20, 7.12, 7.06, 5.83, 5.71, 5.19, 4.56, 4.13, 3.99, 2.70, 2.34-2.21, 1.94, 1.84, 1.71-1.57.

Example 2-18

2-[(2R,4aR,5R,6R,7aS)-6-Hydroxy-5-{(1E)-3-[4-(trifluoromethyl)phenoxy]-1-propen-1-yl}octahydrocyclopenta[b]pyran-2-yl]-1,3-thiazole-4-carboxylic acid (Compound 2-18)

LC-MS/ELSD retention time: 0.91 minute;
MASS (ESI, Pos.): 470 (M+H)$^+$;
$^1$H-NMR (CDCl$_3$): δ8.31, 7.54, 6.97, 5.86, 5.72, 5.20, 4.57, 4.14, 4.00, 2.70, 2.35-2.22, 1.97, 1.86, 1.79-1.58.

Example 2-19

2-{(2R,4aR,5R,6R,7aS)-6-Hydroxy-5-[(1E)-3-(2-methoxyphenoxy)-1-propen-1-yl]octahydrocyclopenta[b]pyran-2-yl}-1,3-thiazole-4-carboxylic acid (Compound 2-19)

LC-MS/ELSD retention time: 0.78 minute;
MASS (ESI, Pos.): 432 (M+H)$^+$;
$^1$H-NMR (CDCl$_3$): δ8.30, 6.97-6.85, 5.89, 5.67, 5.18, 4.60, 4.11, 3.99, 2.67, 2.33-2.17, 1.92, 1.82, 1.70-1.56.

Example 2-20

2-{(2R,4aR,5R,6R,7aS)-6-Hydroxy-5-[(1E)-3-(3-methoxyphenoxy)-1-propen-1-yl]octahydrocyclopenta[b]pyran-2-yl}-1,3-thiazole-4-carboxylic acid (Compound 2-20)

LC-MS/ELSD retention time: 0.81 minute;
MASS (ESI, Pos.): 432 (M+H)$^+$;
$^1$H-NMR (CDCl$_3$): δ8.30, 7.17, 6.53-6.47, 5.86, 5.70, 5.20, 4.50, 4.13, 4.00, 3.79, 2.69, 2.34-2.21, 1.94, 1.86, 1.72-1.58.

Example 2-21

2-{(2R,4aR,5R,6R,7aS)-6-Hydroxy-5-[(1E)-3-(4-methoxyphenoxy)-1-propen-1-yl]octahydrocyclopenta[b]pyran-2-yl}-1,3-thiazole-4-carboxylic acid (Compound 2-21)

LC-MS/ELSD retention time: 0.79 minute;
MASS (ESI, Pos.): 432 (M+H)$^+$;
$^1$H-NMR (CDCl$_3$): δ8.30, 6.90-6.79, 5.84, 5.67, 5.18, 4.46, 4.13, 3.97, 3.77, 2.68, 2.34-2.21, 1.93, 1.83, 1.70-1.55.

Example 2-22

2-[(2R,4aR,5R,6R,7aS)-6-Hydroxy-5-{(1E)-5-[4-(trifluoromethoxy)phenoxy]-1-penten-1-yl}octahydrocyclopenta[b]pyran-2-yl]-1,3-thiazole-4-carboxylic acid (Compound 2-22)

TLC: Rf 0.52 (dichloromethane:methanol:acetic acid=90:10:1);
$^1$H-NMR (CDCl$_3$): δ8.15, 7.13, 6.85, 5.55, 5.28, 5.12, 4.11, 3.94, 3.89, 2.49, 2.21, 2.07, 1.96, 1.89-1.73, 1.54, 1.35.

Example 2-23

2-{(2R,4aR,5R,6R,7aS)-5-[(1E)-5-(4-Chloro-3-fluorophenoxy)-1-penten-1-yl]-6-hydroxyoctahydrocyclopenta[b]pyran-2-yl}-1,3-thiazole-4-carboxylic acid (Compound 2-23)

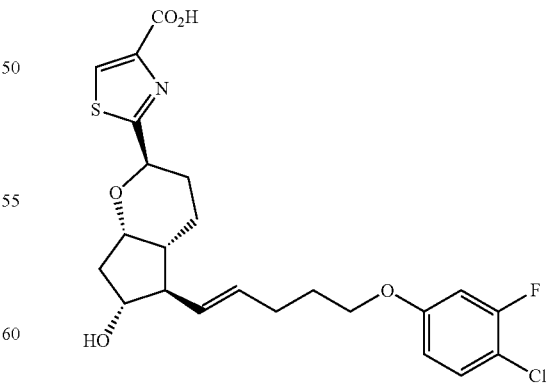

LC-MS/ELSD retention time: 0.99 minute;
MASS (ESI, Pos.): 482 (M+H)$^+$;
$^1$H-NMR (CDCl$_3$): δ8.25, 6.68, 6.63, 5.59, 5.30, 5.15, 4.11, 3.93, 3.89, 2.54, 2.32-2.18, 1.91-1.79, 1.61-1.45.

Example 3

(2R,4aR,5R,6R,7aS)-2-[4-(Hydroxymethyl)-1,3-thiazol-2-yl]-5-[(1E)-5-(4-methoxyphenoxy)-1-penten-1-yl]octahydrocyclopenta[b]pyran-6-ol (Compound 3)

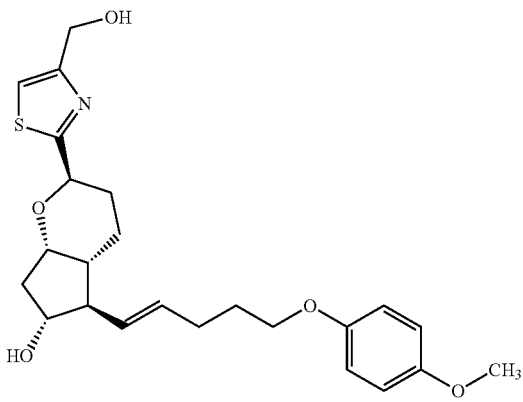 [SMILES: COc1ccc(OCCC/C=C/[C@@H]2[C@H]3CC[C@H](c4nc(CO)cs4)O[C@H]3C[C@H]2O)cc1]

Tetrahydrofuran (1.0 mL) and lithium borohydride (10 mg) were added to Compound 2-1 (62 mg), and the resultant solution was stirred at 50° C. for 17 hours. A 1 M aqueous hydrochloric acid solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=1:1→0:100) to produce a compound of the present invention (32 mg) having the following physical property values.

TLC: Rf 0.52 (ethyl acetate);

$^1$H-NMR (CDCl$_3$): δ7.20, 6.83, 5.61, 5.31, 5.17, 4.77, 4.17, 3.93, 3.90, 3.78, 2.58, 2.29-2.13, 1.98-1.77, 1.59-1.50.

Example 4: Isopropyl

2-{(2R,4aR,5R,6R,7aS)-6-hydroxy-5-[(1E)-5-(4-methoxyphenoxy)-1-penten-1-yl]octahydrocyclopenta[b]pyran-2-yl}-1,3-thiazole-4-carboxylate (Compound 4)

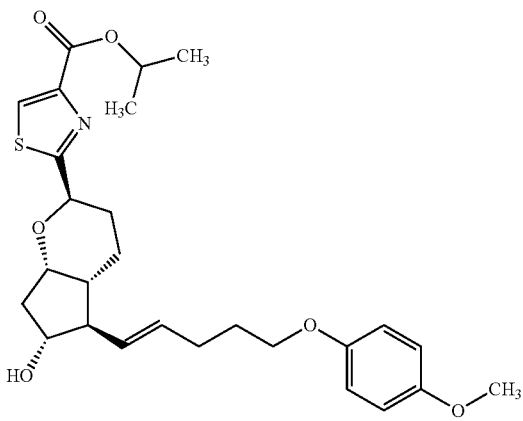 [SMILES: COc1ccc(OCCC/C=C/[C@@H]2[C@H]3CC[C@H](c4nc(C(=O)OC(C)C)cs4)O[C@H]3C[C@H]2O)cc1]

N,N-Dimethylformamide (1.0 mL), isopropyl iodide (30 µL) and potassium carbonate (70 mg) were added to Compound 2-1 (11.8 mg), and the resultant solution was stirred at 50° C. room temperature for 20 hours. A 1M aqueous hydrochloric acid solution was added to the reaction solution, and the resultant solution was extracted with ethyl acetate. An organic layer was washed with water and saturated saline, was then dried over anhydrous sodium sulfate, and was then concentrated under a reduced pressure. A residue was purified by silica gel column chromatography (hexane:ethyl acetate=9:1→1:2) to produce a compound of the present invention (5.8 mg) having the following physical property values.

TLC: Rf 0.71 (hexane:ethyl acetate=1:3);

$^1$H-NMR (CDCl$_3$): δ8.14, 6.84, 5.61, 5.30, 5.28, 5.18, 4.15, 3.94, 3.90, 3.78, 2.56, 2.26, 2.00-1.77, 1.39.

Examples 4-2 to 4-3

The same procedure as in Example 4 was carried out, except that each of Compound 2-2 and Compound 2-16 was used in place of Compound 1. In this manner, compounds of the present invention having the following physical property values were produced.

Example 4-2: Isopropyl

2-{(2R,4aR,5R,6R,7aS)-6-hydroxy-5-[(1E)-4-phenoxy-1-buten-1-yl]octahydrocyclopenta[b]pyran-2-yl}-1,3-thiazole-4-carboxylate (Compound 4-2)

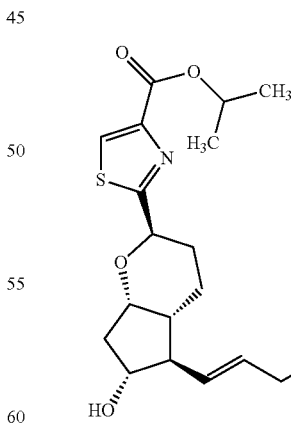

TLC: Rf 0.82 (dichloromethane:methanol=9:1);

$^1$H-NMR (CDCl$_3$): δ7.99, 7.47, 7.17-7.13, 7.08-7.04, 4.79, 4.66, 4.39, 3.91, 3.74, 3.37, 3.07-2.88, 2.54-2.42, 1.90-1.79, 1.39.

Example 4-3: Isopropyl

2-[(2R,4aR,5R,6R,7aS)-6-hydroxy-5-{(1E)-3-[2-(trifluoromethyl)phenoxy]-1-propen-1-yl}octahydrocyclopenta[b]pyran-2-yl]-1,3-thiazole-4-carboxylate (Compound 4-3)

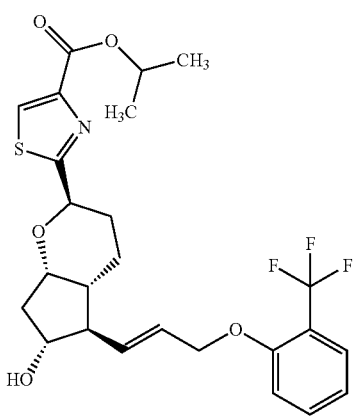 [SMILES: CC(C)OC(=O)c1csc([C@H]2CC[C@@H]3[C@@H](/C=C/COc4ccccc4C(F)(F)F)[C@H](O)C[C@@H]3O2)n1]

LC-MS/ELSD retention time: 1.09 minutes;
MASS (ESI, Pos.): 512 (M+H)+;
$^1$H-NMR (CDCl$_3$): δ8.15, 7.57, 7.47, 7.01, 5.84, 5.74, 5.28, 5.20, 4.64, 4.17, 3.98, 2.68, 2.29, 1.97, 1.81, 1.69-1.52, 1.39.

Example 5

2-{(2R,4aR,5R,6R,7aS)-5-[(1E)-3-(Benzyloxy)-1-propen-1-yl]-6-hydroxyoctahydrocyclopenta[b]pyran-2-yl}-1,3-thiazole-4-carboxylic acid (Compound 5)

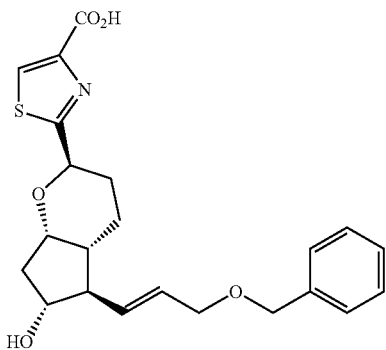 [SMILES: O=C(O)c1csc([C@H]2CC[C@@H]3[C@@H](/C=C/COCc4ccccc4)[C@H](O)C[C@@H]3O2)n1]

The same procedures as in Reference Example 11→Reference Example 12→Reference Example 13→Example 1 were carried out, except that benzyl-2-bromoethyl ether was used in place of (2-bromomethoxy)-tert-butyldimethylsilane. In this manner, a compound of the present invention having the following physical property values was produced.

TLC: Rf 0.09 (dichloromethane:methanol:water=90:10:1);
$^1$H-NMR (CDCl$_3$): δ8.30, 7.37-7.25, 5.87, 5.74, 5.56, 5.48, 5.18, 4.52, 4.51, 4.13-3.84, 4.02, 3.01-2.91, 2.65, 2.40-2.16, 1.92, 1.83, 1.70-1.53 (cis, trans-mixture, cis/trans=3/7).

Example 6

2-{(2R,4aR,5R,6R,7aS)-5-[3-(Benzyloxy)propyl]-6-hydroxyoctahydrocyclopenta[b]pyran-2-yl}-1,3-thiazole-4-carboxylic acid (Compound 6)

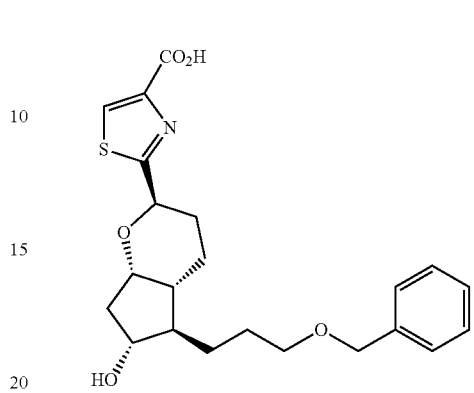

The same procedures as in Reference Example 11→Reference Example 12→Reference Example 13 were carried out, except that benzyl-2-bromoethyl ether was used in place of (2-bromomethoxy)-tert-butyldimethylsilane, thereby producing a compound. Ethanol (0.5 mL), water (1.0 mL), tosylhydrazine (134 mg) and sodium acetate (118 mg) were added to the compound (35 mg), and the resultant solution was stirred at 80° C. for 2 days. Water was added to the reaction solution, and the resultant solution was extracted with ethyl acetate. An organic layer washed with a saturated aqueous sodium hydrogen carbonate solution and saturated saline, was then dried over anhydrous sodium sulfate, and was then concentrated under a reduced pressure. A residue was purified by silica gel column chromatography (hexane:ethyl acetate=9:1→3:1→7:3) to produce a compound. The same procedure as in Example 1 was carried out using the compound to produce a compound of the present invention.

TLC: Rf 0.13 (dichloromethane:methanol:water=90:10:1);
$^1$H-NMR (CDCl$_3$): δ8.29, 7.34-7.27, 5.16, 4.51, 4.15, 3.92, 3.52, 2.29-2.15, 2.10-1.90, 1.79-1.71, 1.69-1.62, 1.57-1.47.

Example 7

2-[(2R,4aR,5R,6R,7aS)-6-Hydroxy-5-(3-phenoxypropyl)octahydrocyclopenta[b]pyran-2-yl]-1,3-thiazole-4-carboxylic acid (Compound 7)

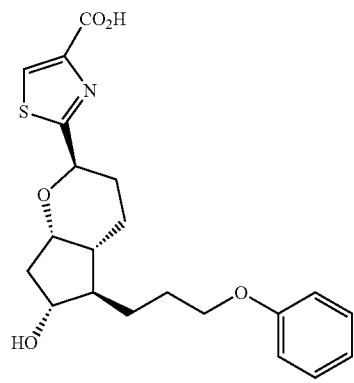 [SMILES: O=C(O)c1csc([C@H]2CC[C@@H]3[C@@H](CCCOc4ccccc4)[C@H](O)C[C@@H]3O2)n1]

The same procedures as in Reference Example 11→Reference Example 12→Reference Example 13→Reference Example 9→Reference Example 15 were carried out, except that (2-bromomethoxy)-tert-butyldimethylsilane was used and phenol was used in place of 3-fluorophenol, thereby producing a compound. Ethanol (1.0 mL), water (2.0 mL), tosylhydrazine (298 mg) and sodium acetate (262 mg) were added to the compound (75 mg), and the resultant solution was stirred at 80° C. for 3 days. Water was added to the reaction solution, and the resultant solution was extracted with ethyl acetate. An organic layer was washed with a saturated aqueous sodium hydrogen carbonate solution and saturated saline, was then dried over anhydrous sodium sulfate, and was then concentrated under a reduced pressure. A residue was purified by silica gel column chromatography (hexane:ethyl acetate=92:8→3:1→65:35) to produce a compound. The same procedure as in Example 1 was carried out using the compound to produce a compound of the present invention (53.7 mg).

TLC: Rf 0.46 (chloroform:methanol:acetic acid=90:10: 1);

$^1$H-NMR (CDCl$_3$): δ8.30, 7.30-7.24, 6.96-6.88, 5.17, 4.18-4.15, 4.00 4.00-3.93, 2.31-2.20, 2.05-1.90, 1.76-1.44.

Examples 7-2 to 7-3

The same procedure as in Example 7 was carried out, except that a corresponding bromo compound was used in place of (2-bromomethoxy)-tert-butyldimethylsilane. In this manner, compounds of the present invention having the following physical property values were produced.

Example 7-2

2-[(2R,4aR,5R,6R,7aS)-6-Hydroxy-5-(5-phenoxypentyl)octahydrocyclopenta[b]pyran-2-yl]-1,3-thiazole-4-carboxylic acid (Compound 7-2)

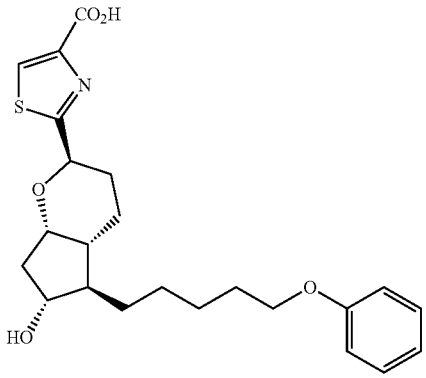 [SMILES: O=C(O)c1csc([C@H]2CC[C@@H]3[C@@H](CCCCCOc4ccccc4)[C@H](O)C[C@@H]3O2)n1]

TLC: Rf 0.14 (dichloromethane:methanol:water=90:10: 1);

$^1$H-NMR (CDCl$_3$): δ8.30, 7.26, 6.92, 6.88, 5.17, 4.15, 3.96, 3.91, 2.28-2.21, 2.06-1.91, 1.81, 1.67, 1.55-1.31.

Example 7-3

2-[(2R,4aR,5R,6R,7aS)-6-Hydroxy-5-(4-phenoxybutyl)octahydrocyclopenta[b]pyran-2-yl]-1,3-thiazole-4-carboxylic acid (Compound 7-3)

TLC: Rf 0.42 (dichloromethane:methanol:acetic acid=60: 10:1);

$^1$H-NMR (CDCl$_3$): δ8.29, 7.28, 6.92, 6.89, 5.17, 4.19-4.11, 3.97, 4.00-3.92, 2.29-2.20, 2.07-1.93, 1.83, 1.70-1.54, 1.44.

Reference Example 16: Ethyl 2-{(2R,4aR,5R,6R,7aS)-6-(acetyloxy)-5-[(1E)-3-oxooct-1-en-1-yl]octahydrocyclopenta [b]pyran-2-yl}-1,3-thiazole-4-carboxylate (Reference Compound 16)

Under an argon stream, potassium phosphate (206 mg) was added to a solution of Reference Compound 10 (179 mg) and dimethyl (2-oxoheptyl)phosphonate (216 mg) in tetrahydrofuran (2.0 mL), and the resultant solution was stirred at room temperature for 12 hours. Water was added to the reaction solution, and the resultant solution was extracted with ethyl acetate. An organic layer was washed with water and saturated saline, was then dried over anhydrous sodium sulfate, and was then concentrated under a reduced pressure. A residue was purified by silica gel column chromatography (hexane:ethyl acetate=4:1→1:1) to produce the title compound (125 mg) having the following physical property value.

TLC: Rf 0.41 (hexane:ethyl acetate=1:1);

Reference Example 17: Ethyl 2-{(2R,4aR,5R,6R,7aS)-6-(acetyloxy)-5-[(1E)-3,3-difluorooct-1-en-1-yl]octahydrocyclopenta[b]pyran-2-yl}-1,3-thiazole-4-carboxylate (Reference Compound 17)

Bis(2-methoxyethyl)aminosulfur trifluoride (0.5 mL) was added to Reference Compound 16 (50 mg), and the resultant solution was stirred at room temperature for 10 days. A saturated aqueous sodium hydrogen carbonate solution was added to the reaction solution, and the resultant solution was extracted with ethyl acetate. An organic layer was washed with water and saturated saline, was then dried over anhydrous sodium sulfate, and was then concentrated under a reduced pressure. A residue was purified by silica gel column chromatography (hexane:ethyl acetate=4:1→1:1) to produce the title compound (125 mg) having the following physical property value.

TLC: Rf 0.50 (hexane:ethyl acetate=2:1);

Example 8

2-{(2R,4aR,5R,6R,7aS)-5-[(1E)-3,3-Difluoro-1-octen-1-yl]-6-hydroxyoctahydrocyclopenta[b]pyran-2-yl}-1,3-thiazole-4-carboxylic acid (Compound 8)

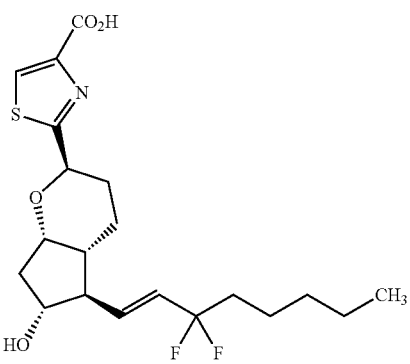 [SMILES: CCCCCC(F)(F)/C=C/[C@@H]1[C@H]2CC[C@H](c3nc(C(=O)O)cs3)O[C@H]2C[C@H]1O]

The same procedure as in Example 1 was carried out using Reference Compound 17 to produce a compound of the present invention having the following physical property values.

TLC: Rf 0.53 (chloroform:methanol:acetic acid=5:1:0.1);
$^1$H-NMR (CDCl$_3$): δ8.32, 5.92, 5.74-5.62, 5.20, 4.14, 4.05-3.99, 2.69, 2.33-2.24, 2.05-1.86, 1.75-1.55, 1.45, 1.35-1.16, 0.90.

Reference Example 18: Ethyl

2-{(2R,4aR,5R,6R,7aS)-6-(acetyloxy)-5-[(1E)-4,4-difluoro-3-hydroxyoct-1-en-1-yl]octahydrocyclopenta[b]pyran-2-yl}-1,3-thiazole-4-carboxylate (Reference Compound 18)

The same procedure as in Reference Example 16 was carried out, except that dimethyl (3,3,-difluoro-2-oxoheptyl)phosphonate was used in place of dimethyl (2-oxoheptyl)phosphonate, thereby producing a compound. Under an argon stream, cerium chloride heptahydrate (22 mg) was added to a solution of the compound (29 mg) in methanol (1.0 mL), and the resultant solution was stirred at 0° C. Sodium borohydride (2.2 mg) was added to the reaction solution, and the resultant solution was stirred at room temperature for 1 hour. A 1.0 M aqueous hydrochloric acid solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=95:5→1:1) to produce the title compound (9.6 mg) having the following physical property value.

TLC: Rf 0.52 (hexane:ethyl acetate=1:1);

Example 9

2-{(2R,4aR,5R,6R,7aS)-5-[(1E)-4,4-Difluoro-3-hydroxy-1-octen-1-yl]-6-hydroxyoctahydrocyclopenta[b]pyran-2-yl}-1,3-thiazole-4-carboxylic acid (Compound 9)

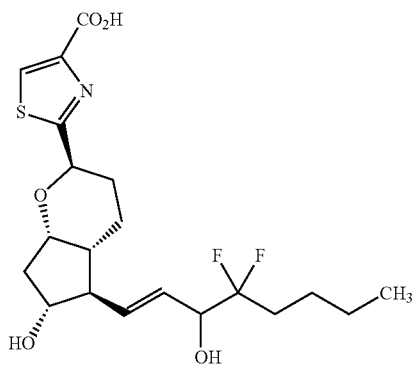 [SMILES: CCCCC(F)(F)C(O)/C=C/[C@@H]1[C@H]2CC[C@H](c3nc(C(=O)O)cs3)O[C@H]2C[C@H]1O]

The same procedure as in Example 1 was carried out using Reference Compound 18 to produce a compound of the present invention having the following physical property values.

TLC: Rf 0.14 (ethyl acetate:methanol=4:1);
$^1$H-NMR (CDCl$_3$): δ8.31, 5.78, 5.69, 5.19, 4.30-4.19, 4.13, 4.00, 2.69, 2.35-2.16, 2.00-1.77, 1.70-1.48, 1.46-1.37, 0.92.

Reference Example 19: Ethyl

2-{(2R,4aR,5S,6R,7aS)-6-(acetyloxy)-5-[(E)-2-iodoethenyl]octahydrocyclopenta[b]pyran-2-yl}-1,3-thiazole-4-carboxylate (Reference Compound 19)

Under a nitrogen stream, a solution of iodoform (15.0 g) and Reference Compound 10 (5.58 g) in tetrahydrofuran (50 mL) was added dropwise to a solution of chromium chloride (13.1 g) in tetrahydrofuran (90 mL) at 0° C., and the resultant solution was stirred at 0° C. for 3 hours. A saturated aqueous sodium hydrogen carbonate solution was added to the reaction solution, and the resultant solution was filtered through Celite. Saturated saline was added to a filtrate to separate an organic layer. An aqueous layer was extracted with ethyl acetate, the resultant extract was combined with the organic layer, and the resultant solution was dried over anhydrous sodium sulfate and was then concentrated under a reduced pressure. A residue was purified by silica gel column chromatography (hexane:ethyl acetate=10:1→4:1) to produce the title compound (3.85 g) having the following physical property value.

TLC: Rf 0.61 (hexane:ethyl acetate=1:1).

Reference Example 20: Ethyl 2-((2R,4aR,5R,6R,7aS)-6-(acetyloxy)-5-[(1E)-5-(4-cyanophenyl)-3-hydroxy pent-1-en-1-yl]octahydrocyclopenta[b]pyran-2-yl-1,3-thiazole-4-carboxylate (Reference Compound 20)

Under an argon stream, 4-(3-oxo-propyl)-benzonitrile (32.4 mg), chromium chloride (50 mg) and nickel chloride (0.3 mg) were added to a solution of Reference Compound 19 (50 mg) in dimethyl sulfoxide (1.5 mL), and the resultant solution was stirred at room temperature for 16 hours. Water was added to the reaction solution, and the resultant solution was extracted with ethyl acetate. An organic layer was washed with water and saturated saline, was then dried over anhydrous sodium sulfate, and was then concentrated under a reduced pressure. A residue obtained was purified by silica gel column chromatography (hexane:ethyl acetate=4:1→1:2) to produce the title compound (32.3 mg) having the following physical property value.

TLC: Rf 0.22 (hexane:ethyl acetate=1:1).

Example 10

2-{(2R,4aR,5R,6R,7aS)-5-[(1E)-5-(4-Cyanophenyl)-3-hydroxy-1-penten-1-yl]-6-hydroxyoctahydrocyclopenta[b]pyran-2-yl}-1,3-thiazole-4-carboxylic acid (Compound 10)

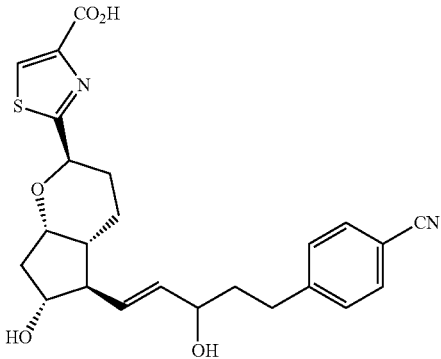 [SMILES: N#Cc1ccc(CCC(O)/C=C/[C@@H]2[C@H]3CC[C@H](c4nc(C(=O)O)cs4)O[C@H]3C[C@H]2O)cc1]

The same procedure as in Example 1 was carried out using Reference Compound 20 to produce a compound of the present invention having the following physical property values.

TLC: Rf 0.57 (dichloromethane:methanol=4:1);

$^1$H-NMR (CD$_3$OD): δ8.34, 7.63, 7.37, 5.64. 5.57, 5.13, 4.13, 4.04, 3.89, 3.79, 2.60, 2.41, 2.27, 2.17, 1.95-1.80, 1.70-1.55.

Examples 10-2 to 10-6

The same procedures as in Reference Example 20→Example 1 were carried out, except that Reference Compound 19 was used and a corresponding aldehyde compound was used in place of 4-(3-oxo-propyl)-benzonitrile. In this manner, compounds of the present invention having the following physical property values were produced.

Example 10-2

2-{(2R,4aR,5R,6R,7aS)-6-Hydroxy-5-[(1E)-3-hydroxy-1-octen-1-yl]octahydrocyclopenta[b]pyran-2-yl}-1,3-thiazole-4-carboxylic acid (Compound 10-2)

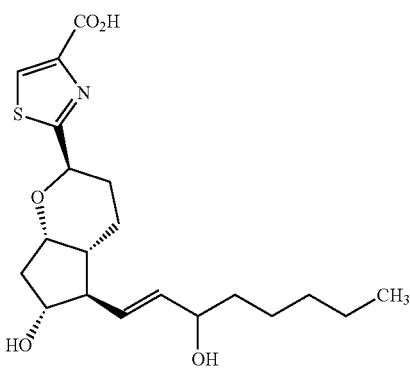 [SMILES: CCCCCC(O)/C=C/[C@@H]1[C@H]2CC[C@H](c3nc(C(=O)O)cs3)O[C@H]2C[C@H]1O]

TLC: Rf 0.43 (chloroform:methanol:acetic acid=5:1:0.1);

$^1$H-NMR (CDCl$_3$): δ8.30, 5.65, 5.50, 5.19, 4.15-4.09, 2.62, 2.35-2.17, 1.97-1.81, 1.67-1.51, 1.41-1.27, 0.89.

Example 10-3

2-{(2R,4aR,5R,6R,7aS)-5-[(1E)-5-Cyclopentyl-3-hydroxy-1-penten-1-yl]-6-hydroxyoctahydrocyclopenta[b]pyran-2-yl}-1,3-thiazole-4-carboxylic acid (Compound 10-3)

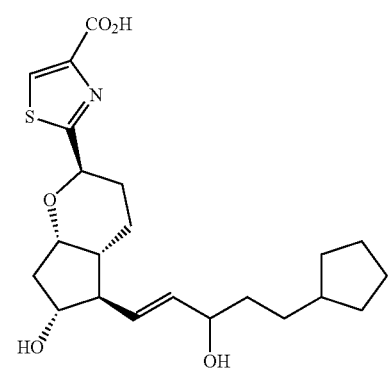 [SMILES: O=C(O)c1csc([C@H]2CC[C@@H]3[C@@H](/C=C/C(O)CCC4CCCC4)[C@H](O)C[C@@H]3O2)n1]

TLC: Rf 0.44 (dichloromethane:methanol:acetic acid=90:10:1);

$^1$H-NMR (CD$_3$OD): δ8.34, 5.61-5.43, 5.13, 4.12, 3.99, 3.83, 2.51, 2.38, 2.25, 2.22, 1.90, 1.78, 1.66-1.47, 1.47-1.29, 1.19-1.05.

Example 10-4

2-{(2R,4aR,5R,6R,7aS)-6-Hydroxy-5-[(1E)-3-hydroxy-5-(2-naphthyl)-1-penten-1-yl]octahydrocyclopenta[b]pyran-2-yl}-1,3-thiazole-4-carboxylic acid (Compound 10-4)

TLC: Rf 0.70 (dichloromethane:methanol=4:1);

$^1$H-NMR (CD$_3$OD): δ8.34, 7.79-7.74, 7.64, 7.45-7.33, 5.72, 5.51, 5.12, 4.13-4.07, 3.89, 2.87, 2.53, 2.39, 2.24, 2.10, 1.94, 1.70-1.55.

Example 10-5

2-{(2R,4aR,5R,6R,7aS)-6-Hydroxy-5-[(1E)-3-hydroxy-1-decen-1-yl]octahydrocyclopenta[b]pyran-2-yl}-1,3-thiazole-4-carboxylic acid (Compound 10-5)

TLC: Rf 0.48 (dichloromethane:methanol=4:1);

$^1$H-NMR (CD$_3$OD): δ8.33, 5.59, 5.50, 5.14, 4.13, 4.01, 3.88, 2.51, 2.38, 2.24, 2.10, 1.92, 1.72-1.48, 1.39-1.29, 0.90.

Example 10-6

2-{(2R,4aR,5R,6R,7aS)-6-Hydroxy-5-[(1E)-3-hydroxy-4-phenyl-1-buten-1-yl]octahydrocyclopenta[b]pyran-2-yl}-1,3-thiazole-4-carboxylic acid (Compound 10-6)

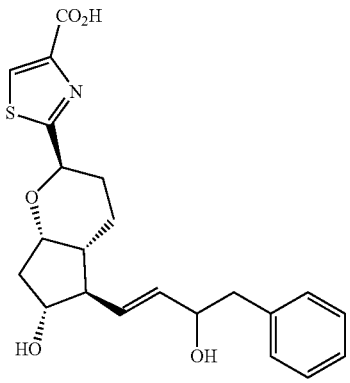 [SMILES: O=C(O)c1csc([C@H]2CC[C@@H]3[C@@H](/C=C/C(O)Cc4ccccc4)[C@H](O)C[C@@H]3O2)n1]

TLC: Rf 0.48 (dichloromethane:methanol:acetic acid=5:1:0.1);

$^1$H-NMR (DMSO-$d_6$): δ8.44, 7.27-7.12, 5.56-5.45, 5.36, 5.27, 5.11, 4.78, 4.71, 4.12, 3.98, 3.65, 3.16, 2.78-2.61, 2.35-2.19, 2.04, 1.96, 1.68, 1.53-1.23.

Examples 11-1 to 11-2

The same procedures as in Reference Example 11→Reference Example 12→Reference Example 13→Reference Example 9→Example 1 were carried out, except that a corresponding bromo compound was used in place of (2-bromomethoxy)-tert-butyldimethylsilane. In this manner, compounds of the present invention having the following physical property values were produced.

Example 11-1

2-{(2R,4aR,5R,6R,7aS)-6-Hydroxy-5-[(1E)-4-hydroxy-1-octen-1-yl]octahydrocyclopenta[b]pyran-2-yl}-1,3-thiazole-4-carboxylic acid (Compound 11-1)

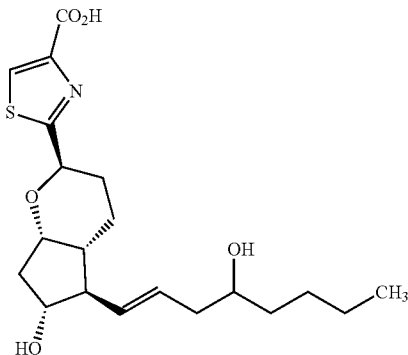 [SMILES: CCCCC(O)C/C=C/[C@@H]1[C@H]2CC[C@H](c3nc(C(=O)O)cs3)O[C@H]2C[C@H]1O]

TLC: Rf 0.40 (dichloromethane:methanol:water=50:10:1);

$^1$H-NMR (CDCl$_3$): δ8.30, 5.61, 5.38, 5.18, 4.12, 3.94, 3.64, 2.62, 2.33-2.14, 1.92, 1.81, 1.65-1.54, 1.46, 1.34, 1.26, 0.91.

Example 11-2

2-{(2R,4aR,5R,6R,7aS)-5-[(1E,4S)-4-(1-Ethylcyclobutyl)-4-hydroxy-1-buten-1-yl]-6-hydroxyoctahydrocyclopenta[b]pyran-2-yl}-1,3-thiazole-4-carboxylic acid (Compound 11-2)

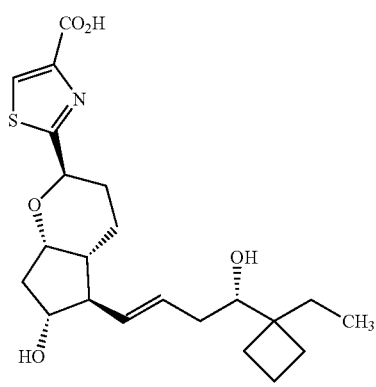 [SMILES: CCC1([C@@H](O)C/C=C/[C@@H]2[C@H]3CC[C@H](c4nc(C(=O)O)cs4)O[C@H]3C[C@H]2O)CCC1]

TLC: Rf 0.16 (dichloromethane:methanol=9:1);

$^1$H-NMR (CD$_3$OD): δ8.34, 5.63, 5.34, 5.13, 4.12, 3.84, 3.52, 2.51, 2.37, 2.21, 2.05-1.95, 1.93-1.74, 1.74-1.57, 0.93.

Reference Example 21: Ethyl

2-{(2R,4aR,5R,6R,7aS)-6-(acetyloxy)-5-[(1E,3S)-3-hydroxyoct-1-en-1-yl]octahydrocyclopenta[b]pyran-2-yl}-1,3-thiazole-4-carboxylate (Reference Compound 21)

Under an argon stream, a 1.0 M (R)-CBS tetrahydrofuran solution (40 μL) and 1.0 M borane-dimethyl sulfide complex/dichloromethane (100 μL) were added to a solution of Reference Compound 16 (70 mg) in tetrahydrofuran (1 mL), and the resultant solution was stirred at room temperature for 1 hour. Ethanol was added to the reaction solution, and the resultant solution was concentrated under a reduced pressure. A residue was purified by silica gel column chromatography (hexane:ethyl acetate=4:1→1:1) to produce the title compound (63 mg) having the following physical property value.

TLC: Rf 0.28 (hexane:ethyl acetate=3:2).

Example 12

2-{(2R,4aR,5R,6R,7aS)-6-Hydroxy-5-[(1E,3S)-3-hydroxy-1-octen-1-yl]octahydrocyclopenta[b]pyran-2-yl}-1,3-thiazole-4-carboxylic acid (Compound 12)

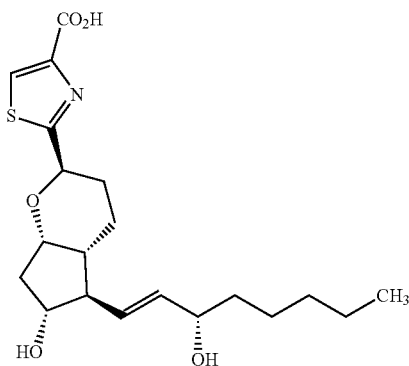 [SMILES: CCCCC[C@H](O)/C=C/[C@@H]1[C@H]2CC[C@H](c3nc(C(=O)O)cs3)O[C@H]2C[C@H]1O]

The same procedure as in Example 1 was carried out using Reference Compound 21 to produce a compound of the present invention having the following physical property values.

TLC: Rf 0.40 (chloroform:methanol:acetic acid=5:1:0.1);

$^1$H-NMR (DMSO-$d_6$): δ8.44, 5.45, 5.36, 5.12, 4.73, 4.54, 4.01, 3.87, 3.70, 2.37, 2.36-2.22, 2.08, 1.96, 1.54-1.25.

Reference Example 22: Propan-2-yl

2-[(2R,4aR,5S,6R,7aS)-5-({[tert-butyl(diphenypsilyl]oxy}methyl)-6-hydroxyoctahydrocyclopenta[b]pyran-2-yl]-1,3-thiazole-4-carboxylate (Reference Compound 22)

The same procedures as in Example 1→Example 4 were carried out using Reference Compound 8 to produce the title compound having the following physical property value.

TLC: Rf 0.20 (hexane:ethyl acetate=3:1).

Reference Example 23: Propan-2-yl

2-{(2R,4aR,5S,6R,7aS)-5-({[tert-butyl(diphenyl)silyl]oxy}methyl)-6-[(oxan-2-yl)oxy]octahydrocyclopenta[b]pyran-2-yl}-1,3-thiazole-4-carboxylate (Reference Compound 23)

Under a nitrogen stream, pyridinium para-toluenesulfonate (2.3 g) and 3,4-dihydro-2H-pyran (15.9 g) were added to a solution of Reference Compound 22 (54.8 g) in dichloromethane (20 mL), and the resultant solution was stirred at room temperature for 16 hours. A saturated aqueous sodium hydrogen carbonate solution was added to the reaction solution, and the resultant solution was extracted with ethyl acetate. An organic layer was washed with water and saturated saline, was then dried over anhydrous sodium sulfate, and was then concentrated under a reduced pressure. A residue was purified by silica gel column chromatography (hexane:ethyl acetate=1:1→1:2) to produce the title compound (38.8 g) having the following physical property value.

TLC: Rf 0.50 (hexane:ethyl acetate=3:1).

Reference Example 24: Propan-2-yl

2-{(2R,4aR,5S,6R,7aS)-5-(hydroxymethyl)-6-[(oxan-2-yl)oxy]octahydrocyclopenta[b]pyran-2-yl}-1,3-thiazole-4-carboxylate (Reference Compound 24)

The same procedure as in Reference Example 9 was carried out using Reference Compound 23 to produce the title compound having the following physical property value.

TLC: Rf 0.40 (hexane:ethyl acetate=1:2).

Reference Example 25: Propan-2-yl

2-{(2R,4aR,5R,6R,7aS)-5-[(E)-2-methoxyethenyl]-6-[(oxan-2-yl)oxy]octahydrocyclopenta[b]pyran-2-yl}-1,3-thiazole-4-carboxylate (Reference Compound 25)

The same procedure as in Reference Example 10 was carried out using Reference Compound 24 to produce a compound. Tetrahydrofuran (1.0 mL) was added to the compound (120 mg) to dissolve the compound therein (a solution A). 85% Potassium tert-butoxide (63.5 mg) was added to a solution of (methoxymethyl)triphenylphosphonium chloride (194 mg) in tetrahydrofuran (1.4 mL) at 0° C., and the resultant solution was stirred for 10 minutes. The solution A was added dropwise to the reaction solution, and the resultant solution was stirred at 0° C. for 20 minutes. A saturated aqueous ammonium chloride solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=9:1→7:3) to produce the title compound (24.8 mg) having the following physical property value.

TLC: Rf 0.42 (hexane:ethyl acetate=7:3).

Reference Example 26: Propan-2-yl

2-[(2R,4aR,5R,6R,7aS)-6-hydroxy-5-(2-oxoethyl)octahydrocyclopenta[b]pyran-2-yl]-1, 3-thiazole-4-carboxylate (Reference Compound 26)

Under an argon stream, para-toluenesulfonic acid monohydrate (478 mg) was added to a solution of Reference Compound 25 (3.8 g) in acetone (138 mL)/water (12 mL) at 0° C., and the resultant solution was stirred at room temperature for 3 hours. A saturated aqueous sodium hydrogen carbonate solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=2:

3→1:4→0:10→ethyl acetate:methanol=9:1) to produce the title compound (2.27 g) having the following physical property value.

TLC: Rf 0.22 (ethyl acetate).

Reference Example 27: Propan-2-yl 2-[(2R,4aR,5R,6R,7aS)-6-(acetyloxy)-5-(2-oxoethyl) octahydrocyclopenta[b]pyran-2-yl]-1,3-thiazole-4-carboxylate (Reference Compound 27)

Under an argon stream, triethylamine (2.15 mL), acetic anhydride (0.728 mL) and N,N-dimethyl-4-aminopyridine (39 mg) were added to a solution of Reference Compound 26 (2.27 g) in dichloromethane (40 mL) at 0° C., and the resultant solution was stirred at room temperature for 2 hours. A saturated aqueous ammonium chloride solution was added to the reaction solution, and the resultant solution was extracted with ethyl acetate. An organic layer was washed with a saturated aqueous sodium hydrogen carbonate solution and saturated saline, was then dried over anhydrous sodium sulfate, and was then concentrated under a reduced pressure. A residue was purified by silica gel column chromatography (hexane:ethyl acetate=7:3→1:1) to produce the title compound (2.28 g) having the following physical property value.

TLC: Rf 0.48 (hexane:ethyl acetate=4:6).

Reference Example 28: Propan-2-yl 2-[(2R,4aR,5R,6R,7aS)-6-(acetyloxy)-5-(2-hydroxyethyl)octahydrocyclopenta[b]pyran-2-yl]-1,3-thiazole-4-carboxylate (Reference Compound 28)

Sodium borohydride (328 mg) was added to a solution of Reference Compound 27 (2.28 g) in methanol (50 mL) at 0° C., and the resultant solution was stirred for 1 hour. A saturated aqueous ammonium chloride solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=1:1→1:3) to produce the title compound (2.04 g) having the following physical property value.

TLC: Rf 0.38 (hexane:ethyl acetate=3:7).

Examples 13-1 to 13-21

The same procedures as in Reference Example 15→Example 1 were carried out, except that Reference Compound 28 was used and 3-fluorophenol or a phenol compound corresponding thereto was used. In this manner, compounds of the present invention having the following physical property values were produced.

Example 13-1

2-[(2R,4aR,5R,6R,7aS)-6-Hydroxy-5-(2-phenoxyethyl)octahydrocyclopenta[b]pyran-2-yl]-1,3-thiazole-4-carboxylic acid (Compound 13-1)

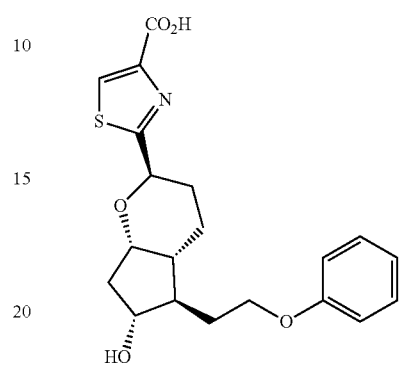

TLC: Rf 0.26 (dichloromethane:methanol:acetic acid=90:10:1);

$^1$H-NMR (DMSO-d$_6$): δ8.42, 7.26, 6.91, 6.90, 5.06, 4.81, 4.10-3.99, 3.68, 2.21-2.08, 1.87-1.75, 1.70-1.55.

Example 13-2

2-{(2R,4aR,5R,6R,7aS)-6-Hydroxy-5-[2-(3-methylphenoxy)ethyl]octahydrocyclopenta[b]pyran-2-yl}-1,3-thiazole-4-carboxylic acid (Compound 13-2)

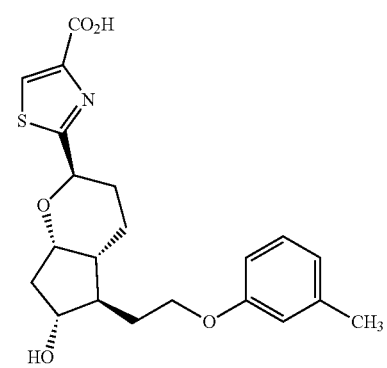 [SMILES: Cc1cccc(OCC[C@@H]2[C@H]3CC[C@H](c4nc(C(=O)O)cs4)O[C@H]3C[C@H]2O)c1]

LC-MS/ELSD retention time: 0.86 minute;

MASS (ESI, Pos.): 404 (M+H)$^+$;

$^1$H-NMR (DMSO-d$_6$): δ8.40, 7.13, 6.72-6.67, 5.05, 4.79, 4.09-3.98, 3.71-3.63, 2.26, 2.19-2.05, 1.84-1.72, 1.65, 1.56.

Example 13-3

2-{(2R,4aR,5R,6R,7aS)-6-Hydroxy-5-[2-(2-methylphenoxy)ethyl]octahydrocyclopenta[b]pyran-2-yl}-1,3-thiazole-4-carboxylic acid (Compound 13-3)

LC-MS/ELSD retention time: 0.87 minute;

MASS (ESI, Pos.): 404 (M+H)$^+$;

¹H-NMR (DMSO-d₆): δ8.35, 7.12, 7.11, 6.89, 6.80, 5.06, 4.80, 4.06, 3.69, 2.15, 2.12, 1.84, 1.66, 1.57.

Example 13-4

2-{(2R,4aR,5R,6R,7aS)-6-Hydroxy-5-[2-(4-methyl-phenoxy)ethyl]octahydrocyclopenta[b]pyran-2-yl}-1,3-thiazole-4-carboxylic acid (Compound 13-4)

LC-MS/ELSD retention time: 0.86 minute;
MASS (ESI, Pos.): 404 (M+H)⁺;
¹H-NMR (DMSO-d₆): δ8.40, 7.05, 6.79, 5.05, 4.78, 4.00, 3.66, 2.21, 2.16, 1.81, 1.67, 1.55.

Example 13-5

2-{(2R,4aR,5R,6R,7aS)-5-[2-(2-Fluorophenoxy)ethyl]-6-hydroxyoctahydrocyclopenta[b]pyran-2-yl}-1,3-thiazole-4-carboxylic acid (Compound 13-5)

LC-MS/ELSD retention time: 0.82 minute;
MASS (ESI, Pos.): 408 (M+H)⁺;
¹H-NMR (DMSO-d₆): δ8.36, 7.21-7.10, 6.91, 5.05, 4.82, 4.13, 4.05, 3.67, 2.17, 1.83, 1.65, 1.56.

Example 13-6

2-{(2R,4aR,5R,6R,7aS)-5-[2-(3-Fluorophenoxy)ethyl]-6-hydroxyoctahydrocyclopenta[b]pyran-2-yl}-1,3-thiazole-4-carboxylic acid (Compound 13-6)

LC-MS/ELSD retention time: 0.83 minute;
MASS (ESI, Pos.): 408 (M+H)⁺;
¹H-NMR (DMSO-d₆): δ8.42, 7.29, 6.75, 5.06, 4.82, 4.07, 3.67, 2.12, 1.81, 1.65, 1.55.

Example 13-7

2-{(2R,4aR,5R,6R,7aS)-5-[2-(4-Fluorophenoxy)ethyl]-6-hydroxyoctahydrocyclopenta[b]pyran-2-yl}-1,3-thiazole-4-carboxylic acid (Compound 13-7)

LC-MS/ELSD retention time: 0.82 minute;
MASS (ESI, Pos.): 408 (M+H)⁺;
¹H-NMR (DMSO-d₆): δ8.41, 7.10, 6.93, 5.06, 4.82, 4.05, 3.67, 2.16, 2.11, 1.79, 1.65, 1.55.

Example 13-8

2-{(2R,4aR,5R,6R,7aS)-5-[2-(2-Chlorophenoxy)ethyl]-6-hydroxyoctahydrocyclopenta[b]pyran-2-yl}-1,3-thiazole-4-carboxylic acid (Compound 13-8)

LC-MS/ELSD retention time: 0.86 minute;
MASS (ESI, Pos.): 424 (M+H)⁺;
¹H-NMR (DMSO-d₆): δ8.41, 7.40, 7.28, 7.11, 6.96, 5.05, 4.80, 4.15, 4.06, 3.69, 2.17, 1.85, 1.65, 1.60.

Example 13-9

2-{(2R,4aR,5R,6R,7aS)-5-[2-(3-Chlorophenoxy)ethyl]-6-hydroxyoctahydrocyclopenta[b]pyran-2-yl}-1,3-thiazole-4-carboxylic acid (Compound 13-9)

LC-MS/ELSD retention time: 0.88 minute;
MASS (ESI, Pos.): 424 (M+H)⁺;
¹H-NMR (DMSO-d₆): δ8.41, 7.28, 6.94, 6.89, 5.05, 4.80, 4.08, 3.67, 2.14, 1.80, 1.65, 1.55.

Example 13-10

2-{(2R,4aR,5R,6R,7aS)-5-[2-(4-Chlorophenoxy)ethyl]-6-hydroxyoctahydrocyclopenta[b]pyran-2-yl}-1,3-thiazole-4-carboxylic acid (Compound 13-10)

LC-MS/ELSD retention time: 0.88 minute;
MASS (ESI, Pos.): 424 (M+H)⁺;
¹H-NMR (DMSO-d₆): δ8.40, 7.30, 6.93, 5.05, 4.80, 4.05, 3.67, 2.14, 1.80, 1.64, 1.55.

Example 13-11

2-[(2R,4aR,5R,6R,7aS)-6-Hydroxy-5-{2-[2-(trifluoromethoxy)phenoxy]ethyl}octahydrocyclopenta[b]pyran-2-yl]-1,3-thiazole-4-carboxylic acid (Compound 13-11)

LC-MS/ELSD retention time: 0.91 minute;
MASS (ESI, Pos.): 474 (M+H)⁺;
¹H-NMR (DMSO-d₆): δ8.35, 7.33, 7.20, 6.98, 5.04, 4.81, 4.15, 4.06, 3.67, 2.16, 1.83, 1.65, 1.57.

Example 13-12

2-[(2R,4aR,5R,6R,7aS)-6-Hydroxy-5-{2-[3-(trifluoromethoxy)phenoxy]ethyl}octahydrocyclopenta[b]pyran-2-yl]-1,3-thiazole-4-carboxylic acid (Compound 13-12)

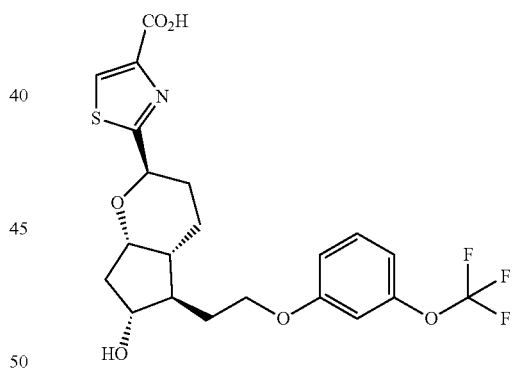

LC-MS/ELSD retention time: 0.93 minute;
MASS (ESI, Pos.): 474 (M+H)⁺;
¹H-NMR (DMSO-d₆): δ8.40, 7.39, 6.96, 6.89, 5.06, 4.81, 4.10, 3.68, 2.15, 1.81, 1.63, 1.55.

Example 13-13

2-[(2R,4aR,5R,6R,7aS)-6-Hydroxy-5-{2-[4-(trifluoromethoxy)phenoxy]ethyl}octahydrocyclopenta[b]pyran-2-yl]-1,3-thiazole-4-carboxylic acid (Compound 13-13)

LC-MS/ELSD retention time: 0.93 minute;
MASS (ESI, Pos.): 474 (M+H)⁺;
¹H-NMR (DMSO-d₆): δ8.40, 7.26, 7.00, 5.06, 4.80, 4.07, 3.68, 2.25-2.04, 1.81, 1.65, 1.55.

Example 13-14

2-[(2R,4aR,5R,6R,7aS)-6-Hydroxy-5-{2-[2-(trifluoromethyl)phenoxy]ethyl}octahydrocyclopenta[b]pyran-2-yl]-1,3-thiazole-4-carboxylic acid (Compound 13-14)

LC-MS/ELSD retention time: 0.90 minute;
MASS (ESI, Pos.): 458 (M+H)$^+$;
$^1$H-NMR (DMSO-d$_6$): δ8.42, 7.60, 7.59, 7.21, 7.06, 5.06, 4.80, 4.21, 4.07, 3.69, 2.19-2.05, 1.83, 1.65, 1.58.

Example 13-15

2-[(2R,4aR,5R,6R,7aS)-6-Hydroxy-5-{2-[3-(trifluoromethyl)phenoxy]ethyl}octahydrocyclopenta[b]pyran-2-yl]-1,3-thiazole-4-carboxylic acid (Compound 13-15)

LC-MS/ELSD retention time: 0.92 minute;
MASS (ESI, Pos.): 458 (M+H)$^+$;
$^1$H-NMR (DMSO-d$_6$): δ8.40, 7.50, 7.23, 5.06, 4.81, 4.15, 4.06, 3.69, 2.17, 1.83, 1.65, 1.56.

Example 13-16

2-[(2R,4aR,5R,6R,7aS)-6-Hydroxy-5-{2-[4-(trifluoromethyl)phenoxy]ethyl}octahydrocyclopenta[b]pyran-2-yl]-1,3-thiazole-4-carboxylic acid (Compound 13-16)

LC-MS/ELSD retention time: 0.92 minute;
MASS (ESI, Pos.): 458 (M+H)$^+$;
$^1$H-NMR (DMSO-d$_6$): δ8.39, 7.63, 7.09, 5.06, 4.81, 4.16, 4.06, 3.70, 2.15, 1.83, 1.65, 1.56.

Example 13-17

2-{(2R,4aR,5R,6R,7aS)-6-Hydroxy-5-[2-(2-methoxyphenoxy)ethyl]octahydrocyclopenta[b]pyran-2-yl}-1,3-thiazole-4-carboxylic acid (Compound 13-17)

LC-MS/ELSD retention time: 0.78 minute;
MASS (ESI, Pos.): 420 (M+H)$^+$;
$^1$H-NMR (DMSO-d$_6$): δ8.38, 6.94, 6.86, 5.05, 4.79, 4.05, 3.74, 3.67, 2.14, 1.81, 1.67, 1.56.

Example 13-18

2-{(2R,4aR,5R,6R,7aS)-6-Hydroxy-5-[2-(3-methoxyphenoxy)ethyl]octahydrocyclopenta[b]pyran-2-yl}-1,3-thiazole-4-carboxylic acid (Compound 13-18)

LC-MS/ELSD retention time: 0.81 minute;
MASS (ESI, Pos.): 420 (M+H)+;
$^1$H-NMR (DMSO-d$_6$): δ8.41, 7.15, 6.50, 6.47, 5.05, 4.80, 4.05, 3.71, 3.67, 2.14, 1.80, 1.65, 1.56.

Example 13-19

2-{(2R,4aR,5R,6R,7aS)-6-Hydroxy-5-[2-(4-methoxyphenoxy)ethyl]octahydrocyclopenta[b]pyran-2-yl}-1,3-thiazole-4-carboxylic acid (Compound 13-19)

LC-MS/ELSD retention time: 0.79 minute;
MASS (ESI, Pos.): 404 (M+H)$^+$;
$^1$H-NMR (DMSO-d$_6$): δ8.41, 6.84, 5.06, 4.79, 4.09-3.92, 3.68, 2.22-2.05, 1.78, 1.65, 1.55.

Example 13-20

2-{(2R,4aR,5R,6R,7aS)-6-Hydroxy-5-[2-(3-methyl-4-nitrophenoxy)ethyl]octahydrocyclopenta[b]pyran-2-yl}-1,3-thiazole-4-carboxylic acid (Compound 13-20)

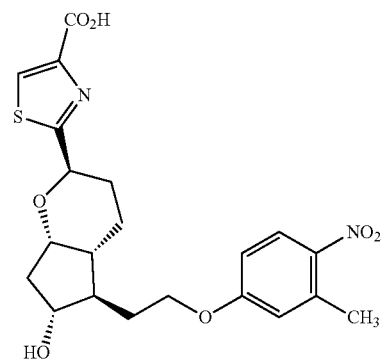 [SMILES: Cc1cc(OCC[C@@H]2[C@H]3CC[C@H](c4nc(C(=O)O)cs4)O[C@H]3C[C@H]2O)ccc1[N+](=O)[O-]]

LC-MS/ELSD retention time: 0.85 minute;
MASS (ESI, Pos.): 449 (M+H)$^+$;
$^1$H-NMR (DMSO-d$_6$): δ8.26, 8.04, 7.01, 6.96, 5.04, 4.83, 4.20, 4.05, 3.68, 2.55, 2.22-2.08, 1.90-1.75, 1.69-1.60, 1.55.

Example 13-21

2-{(2R,4aR,5R,6R,7aS)-5-[2-(3,4-Dichlorophenoxy)ethyl]-6-hydroxyoctahydrocyclopenta[b]pyran-2-yl}-1,3-thiazole-4-carboxylic acid (Compound 13-21)

LC-MS/ELSD retention time: 0.95 minute;
MASS (ESI, Pos.): 458 (M+H)$^+$;
$^1$H-NMR (DMSO-d$_6$): δ8.39, 7.50, 7.21, 6.94, 5.05, 4.81, 4.11-4.00, 3.66, 2.21-2.08, 1.90-1.75, 1.69-1.45.

Example 14: Isopropyl

2-{(2R,4aR,5R,6R,7aS)-6-hydroxy-5-[2-(3-methyl-4-nitrophenoxy)ethyl]octahydrocyclopenta[b]pyran-2-yl}-1,3-thiazole-4-carboxylate (Compound 14)

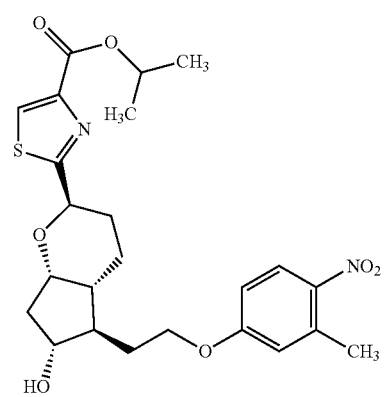 [SMILES: Cc1cc(OCC[C@@H]2[C@H]3CC[C@H](c4nc(C(=O)OC(C)C)cs4)O[C@H]3C[C@H]2O)ccc1[N+](=O)[O-]]

The same procedure as in Example 4 was carried out using Compound 13-20 to produce a compound of the present invention having the following physical property values.

LC-MS/ELSD retention time: 1.05 minutes;

MASS (ESI, Pos.): 491 (M+H)$^+$;

$^1$H-NMR (CDCl$_3$): δ8.13, 8.07, 6.80, 6.78, 5.26, 5.18, 4.21-4.10, 3.98, 2.63, 2.53, 2.28, 2.20-2.11, 1.96-1.80, 1.67-1.55, 1.38.

Example 15

(2R,4aR,5R,6R,7aS)-5-[2-(3,4-Dichlorophenoxy)ethyl]-2-[4-(hydroxymethyl)-1,3-thiazol-2-yl]octahydrocyclopenta[b]pyran-6-ol (Compound 15)

The same procedures as in Reference Example 15→Example 3 were carried out, except that Reference Compound 28 was used and 3,4-dichlorophenol was used in place of 3-fluorophenol, thereby producing a compound of the present invention having the following physical property values.

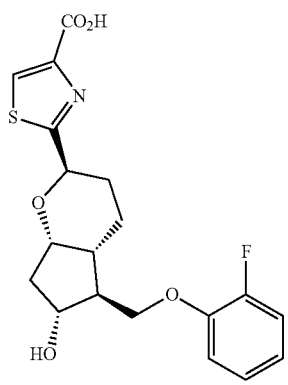 [SMILES: O=C(O)c1csc([C@H]2CC[C@@H]3[C@@H](COc4ccccc4F)[C@H](O)C[C@@H]3O2)n1]

TLC: Rf 0.39 (ethyl acetate);

$^1$H-NMR (CDCl$_3$): δ7.33, 7.21, 7.02, 6.77, 5.18, 4.77, 4.20, 4.09, 3.98, 2.67, 2.27-2.01, 1.96-1.79, 1.68-1.54.

Examples 16-1 to 16-38

The same procedures as in Reference Example 15→Example 1 were carried out, except that Reference Compound 9 was used and a corresponding phenol compound was used in place of 3-fluorophenol. In this manner, compounds of the present invention having the following physical property values were produced.

Example 16-1

2-{(2R,4aR,5S,6R,7aS)-5-[(2-Fluorophenoxy)methyl]-6-hydroxyoctahydrocyclopenta[b]pyran-2-yl}-1,3-thiazole-4-carboxylic acid (Compound 16-1)

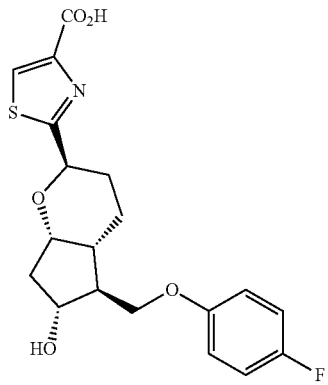 [SMILES: O=C(O)c1csc([C@H]2CC[C@@H]3[C@@H](COc4ccc(F)cc4)[C@H](O)C[C@@H]3O2)n1]

LC-MS/ELSD retention time: 0.79 minute;

MASS (ESI, Pos.): 394 (M+H)$^+$;

$^1$H-NMR (DMSO-d$_6$): δ8.34, 7.17, 6.94, 5.07, 4.89, 4.16, 4.04, 3.90, 2.27-2.04, 1.96-1.65.

Example 16-2

2-{(2R,4aR,5S,6R,7aS)-5-[(4-Fluorophenoxy)methyl]-6-hydroxyoctahydrocyclopenta[b]pyran-2-yl}-1,3-thiazole-4-carboxylic acid (Compound 16-2)

TLC: Rf 0.41 (dichloromethane:methanol:acetic acid=9:1:0.1);

$^1$H-NMR (CDCl$_3$): δ8.31, 6.96, 6.83, 5.21, 4.22, 4.04, 3.91, 2.43, 2.29, 2.18, 2.04, 1.90, 1.76.

Example 16-3

2-{(2R,4aR,5S,6R,7aS)-6-Hydroxy-5-[(3-methyl-phenoxy)methyl]octahydrocyclopenta[b]pyran-2-yl}-1,3-thiazole-4-carboxylic acid (Compound 16-3)

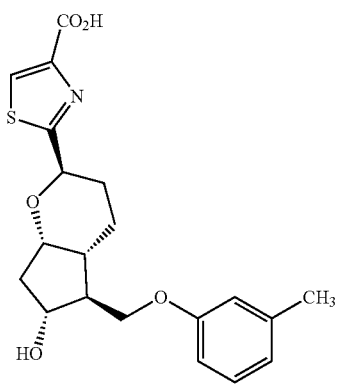 [SMILES: Cc1cccc(OC[C@@H]2[C@H]3CC[C@H](c4nc(C(=O)O)cs4)O[C@H]3C[C@H]2O)c1]

TLC: Rf 0.42 (dichloromethane:methanol:acetic acid=90:10:1);

$^1$H-NMR (DMSO-$d_6$): δ8.42, 7.13, 6.74-6.70, 5.08, 4.88, 4.15-4.03, 3.95-3.82, 2.26, 2.23-2.08, 1.90-1.65.

Example 16-4

2-{(2R,4aR,5S,6R,7aS)-6-Hydroxy-5-[(4-methyl-phenoxy)methyl]octahydrocyclopenta[b]pyran-2-yl}-1,3-thiazole-4-carboxylic acid (Compound 16-4)

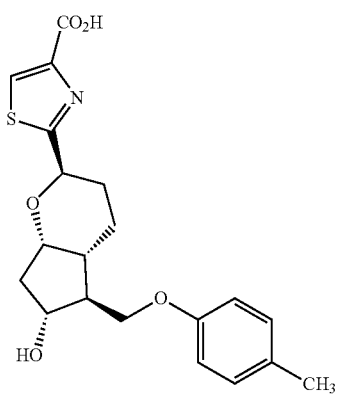 [SMILES: Cc1ccc(OC[C@@H]2[C@H]3CC[C@H](c4nc(C(=O)O)cs4)O[C@H]3C[C@H]2O)cc1]

TLC: Rf 0.40 (dichloromethane:methanol:acetic acid=90:10:1);

$^1$H-NMR (DMSO-$d_6$): δ8.42, 7.06, 6.81, 5.08, 4.87, 4.11, 4.03, 3.88, 2.21, 2.15, 2.07, 1.91-1.64.

Example 16-5

2-{(2R,4aR,5S,6R,7aS)-5-[(2-Chlorophenoxy)methyl]-6-hydroxyoctahydrocyclopenta[b]pyran-2-yl}-1,3-thiazole-4-carboxylic acid (Compound 16-5)

TLC: Rf 0.34 (dichloromethane:methanol:acetic acid=90:10:1);

$^1$H-NMR (DMSO-$d_6$): δ7.99, 7.40, 7.29, 7.14, 6.92, 5.04, 4.18, 4.02, 3.90, 2.23-2.08, 1.95-1.65.

Example 16-6

2-{(2R,4aR,5S,6R,7aS)-5-[(3-Chlorophenoxy)methyl]-6-hydroxyoctahydrocyclopenta[b]pyran-2-yl}-1,3-thiazole-4-carboxylic acid (Compound 16-6)

LC-MS/ELSD retention time: 0.86 minute;
MASS (ESI, Pos.): 410 (M+H)$^+$;

$^1$H-NMR (DMSO-$d_6$): δ8.42, 7.28, 7.01, 6.97, 6.91, 5.08, 4.89, 4.10, 4.01, 3.86, 2.25-2.04, 1.93-1.60.

Example 16-7

2-[(2R,4aR,5S,6R,7aS)-6-Hydroxy-5-{[4-(trifluoromethoxy)phenoxy]methyl}octahydrocyclopenta[b]pyran-2-yl]-1,3-thiazole-4-carboxylic acid (Compound 16-7)

TLC: Rf 0.35 (dichloromethane:methanol:acetic acid=90:10:1); $^1$H-NMR (DMSO-$d_6$): δ8.40, 7.27, 7.03, 5.08, 4.90, 4.10, 3.99, 3.87, 2.19, 2.10, 1.90-1.64.

Example 16-8

2-[(2R,4aR,5S,6R,7aS)-6-Hydroxy-5-{[2-(trifluoromethyl)phenoxy]methyl}octahydrocyclopenta[b]pyran-2-yl]-1,3-thiazole-4-carboxylic acid (Compound 16-8)

TLC: Rf 0.34 (dichloromethane:methanol:acetic acid=90:10:1);

$^1$H-NMR (DMSO-$d_6$): δ8.22, 7.61, 7.59, 7.26, 7.07, 5.08, 4.21, 4.11, 3.88, 2.15, 1.86, 1.70.

Example 16-9

2-[(2R,4aR,5S,6R,7aS)-6-Hydroxy-5-{[3-(trifluoromethyl)phenoxy]methyl}octahydrocyclopenta[b]pyran-2-yl]-1,3-thiazole-4-carboxylic acid (Compound 16-9)

TLC: Rf 0.41 (dichloromethane:methanol:acetic acid=9:1:0.1);

$^1$H-NMR (CDCl$_3$): δ8.31, 7.38, 7.22, 7.07, 5.22, 4.23, 4.10, 3.99, 2.49, 2.32, 2.19, 2.05, 1.91, 1.79.

Example 16-10

2-[(2R,4aR,5S,6R,7aS)-6-Hydroxy-5-{[4-(trifluoromethyl)phenoxy]methyl}octahydrocyclopenta[b]pyran-2-yl]-1,3-thiazole-4-carboxylic acid (Compound 16-10)

TLC: Rf 0.34 (dichloromethane:methanol:acetic acid=90:10:1);

$^1$H-NMR (DMSO-$d_6$): δ8.39, 7.63, 7.12, 5.09, 4.92, 4.14, 4.09, 3.87, 2.21, 2.12, 1.92-1.61.

Example 16-11

2-{(2R,4aR,5S,6R,7aS)-6-Hydroxy-5-[(2-nitrophenoxy)methyl]octahydrocyclopenta[b]pyran-2-yl}-1,3-thiazole-4-carboxylic acid (Compound 16-11)

$^1$H-NMR (DMSO-$d_6$): δ7.99, 7.85, 7.63, 7.35, 7.09, 5.07, 4.91, 4.32-4.04, 3.84, 2.09, 1.81, 1.58.

Example 16-12

2-{(2R,4aR,5S,6R,7aS)-6-Hydroxy-5-[(3-nitrophenoxy)methyl]octahydrocyclopenta[b]pyran-2-yl}-1,3-thiazole-4-carboxylic acid (Compound 16-12)

TLC: Rf 0.44 (dichloromethane:methanol:acetic acid=9:1:0.1);
$^1$H-NMR (CDCl$_3$): δ8.32, 7.83, 7.72, 7.43, 7.23, 5.23, 4.23, 4.15, 4.08, 2.50, 2.30, 2.18, 2.10-1.93, 1.89, 1.79.

Example 16-13

2-[(2R,4aR,5S,6R,7aS)-5-{[2-Chloro-3-(trifluoromethyl)phenoxy]methyl}-6-hydroxyoctahydrocyclopenta[b]pyran-2-yl]-1,3-thiazole-4-carboxylic acid (Compound 16-13)

TLC: Rf 0.40 (dichloromethane:methanol:acetic acid=90:10:1);
$^1$H-NMR (DMSO-$d_6$): δ8.16, 7.50, 7.40, 5.08, 4.94, 4.28, 4.14, 3.91, 2.22-2.04, 1.87, 1.74.

Example 16-14

2-[(2R,4aR,5S,6R,7aS)-5-{[2-Chloro-5-(trifluoromethyl)phenoxy]methyl}-6-hydroxyoctahydrocyclopenta[b]pyran-2-yl]-1,3-thiazole-4-carboxylic acid (Compound 16-14)

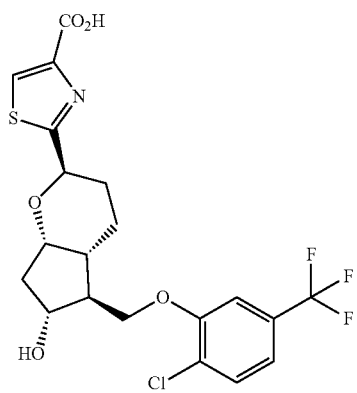 [SMILES: O=C(O)c1csc([C@H]2CC[C@@H]3[C@@H](COc4cc(C(F)(F)F)ccc4Cl)[C@H](O)C[C@@H]3O2)n1]

TLC: Rf 0.34 (dichloromethane:methanol:acetic acid=90:10:1);
$^1$H-NMR (DMSO-$d_6$): δ8.17, 7.65, 7.45, 7.30, 5.08, 4.83, 4.13, 3.91, 2.29-2.08, 1.95-1.67.

Example 16-15

2-{(2R,4aR,5S,6R,7aS)-5-[(2,5-Dichlorophenoxy)methyl]-6-hydroxyoctahydrocyclopenta[b]pyran-2-yl}-1,3-thiazole-4-carboxylic acid (Compound 16-15)

TLC: Rf 0.40 (dichloromethane:methanol:acetic acid=90:10:1);
$^1$H-NMR (DMSO-$d_6$): δ8.41, 7.44, 7.25, 7.00, 5.10, 4.23, 4.14-4.05, 3.88, 2.27-2.05, 1.85, 1.72.

Example 16-16

2-{(2R,4aR,5S,6R,7aS)-5-[(2,3-Difluorophenoxy)methyl]-6-hydroxyoctahydrocyclopenta[b]pyran-2-yl}-1,3-thiazole-4-carboxylic acid (Compound 16-16)

TLC: Rf 0.34 (dichloromethane:methanol:acetic acid=90:10:1);
$^1$H-NMR (DMSO-$d_6$): δ8.23, 7.14, 7.04, 6.95, 5.07, 4.23, 4.10, 3.87, 2.24, 2.14, 1.92-1.64.

Example 16-17

2-{(2R,4aR,5S,6R,7aS)-5-[(4-Fluoro-2-methylphenoxy)methyl]-6-hydroxyoctahydrocyclopenta[b]pyran-2-yl}-1,3-thiazole-4-carboxylic acid (Compound 16-17)

TLC: Rf 0.34 (dichloromethane:methanol:acetic acid=90:10:1);
$^1$H-NMR (DMSO-$d_6$): δ8.00, 6.99, 6.94, 5.05, 4.91, 4.12, 4.05, 3.90, 2.26-2.09, 2.13, 1.86, 1.71.

Example 16-18

2-{(2R,4aR,5S,6R,7aS)-5-[(2-Chloro-4-methylphenoxy)methyl]-6-hydroxyoctahydrocyclopenta[b]pyran-2-yl}-1,3-thiazole-4-carboxylic acid (Compound 16-18)

TLC: Rf 0.43 (dichloromethane:methanol:acetic acid=90:10:1);
$^1$H-NMR (DMSO-$d_6$): δ8.33, 7.22, 7.07, 7.02, 5.08, 4.90, 4.14, 3.99, 3.88, 2.22, 2.15, 1.86, 1.74.

Example 16-19

2-{(2R,4aR,5S,6R,7aS)-5-[(3-Chloro-5-methoxyphenoxy)methyl]-6-hydroxyoctahydrocyclopenta[b]pyran-2-yl}-1,3-thiazole-4-carboxylic acid (Compound 16-19)

TLC: Rf 0.39 (dichloromethane:methanol:acetic acid=90:10:1);
$^1$H-NMR (DMSO-$d_6$): δ8.38, 6.60, 6.57, 6.46, 5.08, 4.90, 4.09, 3.98, 3.85, 3.74, 2.18, 2.07, 1.90-1.68.

Example 16-20

2-{(2R,4aR,5S,6R,7aS)-6-Hydroxy-5-[(3-methoxy-5-methylphenoxy)methyl]octahydrocyclopenta[b]pyran-2-yl}-1,3-thiazole-4-carboxylic acid (Compound 16-20)

TLC: Rf 0.49 (dichloromethane:methanol:acetic acid=90:10:1);

¹H-NMR (DMSO-d₆): δ8.37, 6.34, 6.32, 6.28, 5.08, 4.88, 4.11, 4.05, 3.89, 3.69, 2.22, 2.21-2.03, 1.90-1.68.

Example 16-21

2-[(2R,4aR,5S,6R,7aS)-5-{[4-Chloro-3-(trifluoromethyl)phenoxy]methyl}-6-hydroxyoctahydrocyclopenta[b]pyran-2-yl]-1,3-thiazole-4-carboxylic acid (Compound 16-21)

TLC: Rf 0.44 (dichloromethane:methanol:acetic acid=90:10:1);
¹H-NMR (DMSO-d₆): δ8.36, 7.61, 7.34, 7.27, 5.08, 4.90, 4.18-4.04, 3.87, 2.20, 2.11, 1.90-1.64.

Example 16-22

2-{(2R,4aR,5S,6R,7aS)-5-[(3-Chloro-4-fluorophenoxy)methyl]-6-hydroxyoctahydrocyclopenta[b]pyran-2-yl}-1,3-thiazole-4-carboxylic acid (Compound 16-22)

TLC: Rf 0.38 (dichloromethane:methanol:acetic acid=90:10:1);
¹H-NMR (DMSO-d₆): δ8.37, 7.32, 7.18, 6.95, 5.08, 4.90, 4.08, 3.97, 3.85, 2.19, 2.07, 1.91-1.62.

Example 16-23

2-{(2R,4aR,5S,6R,7aS)-5-[(4-Chloro-3-ethylphenoxy)methyl]-6-hydroxyoctahydrocyclopenta[b]pyran-2-yl}-1,3-thiazole-4-carboxylic acid (Compound 16-23)

TLC: Rf 0.47 (dichloromethane:methanol:acetic acid=90:10:1);
¹H-NMR (DMSO-d₆): δ8.39, 7.25, 6.91, 6.79, 5.08, 4.11, 4.07, 3.95, 3.85, 2.64, 2.28-2.04, 1.95-1.59, 1.15.

Example 16-24

2-[(2R,4aR,5S,6R,7aS)-5-{[3-Fluoro-4-(trifluoromethyl)phenoxy]methyl}-6-hydroxyoctahydrocyclopenta[b]pyran-2-yl]-1,3-thiazole-4-carboxylic acid (Compound 16-24)

LC-MS/ELSD retention time: 0.90 minute;
MASS (ESI, Pos.): 462 (M+H)+;
¹H-NMR (CDCl₃): δ8.32, 7.49, 6.71, 5.22, 4.22, 4.19, 4.09, 3.99, 2.49, 2.30, 2.19-1.98, 1.86, 1.73.

Example 16-25

2-{(2R,4aR,5S,6R,7aS)-5-[(4-Chloro-3-fluorophenoxy)methyl]-6-hydroxyoctahydrocyclopenta[b]pyran-2-yl}-1,3-thiazole-4-carboxylic acid (Compound 16-25)

TLC: Rf 0.38 (dichloromethane:methanol:acetic acid=90:10:1);
¹H-NMR (DMSO-d₆): δ8.20, 7.45, 7.06, 6.85, 5.06, 4.11, 4.02, 3.87, 2.18, 2.08, 1.90-1.59.

Example 16-26

2-[(2R,4aR,5S,6R,7aS)-6-Hydroxy-5-{[3-methyl-4-(trifluoromethyl)phenoxy]methyl}octahydrocyclopenta[b]pyran-2-yl]-1,3-thiazole-4-carboxylic acid (Compound 16-26)

TLC: Rf 0.50 (dichloromethane:methanol:acetic acid=90:10:1);
¹H-NMR (CDCl₃): δ8.31, 7.51, 6.77, 6.72, 5.22, 4.24-4.18, 4.09, 3.98, 2.48, 2.44, 2.29, 2.20-1.98, 1.88, 1.72.

Example 16-27

2-{(2R,4aR,5S,6R,7aS)-5-[(3,4-Dimethoxyphenoxy)methyl]-6-hydroxyoctahydrocyclopenta[b]pyran-2-yl}-1,3-thiazole-4-carboxylic acid (Compound 16-27)

TLC: Rf 0.41 (dichloromethane:methanol:acetic acid=90:10:1);
¹H-NMR (DMSO-d₆): δ8.37, 6.83, 6.54, 6.42, 5.08, 4.87, 4.12, 4.00, 3.89, 3.72, 3.67, 2.18, 2.08, 1.90-1.69.

Example 16-28

2-{(2R,4aR,5S,6R,7aS)-5-[(3,4-Dichlorophenoxy)methyl]-6-hydroxyoctahydrocyclopenta[b]pyran-2-yl}-1,3-thiazole-4-carboxylic acid (Compound 16-28)

TLC: Rf 0.40 (dichloromethane:methanol:acetic acid=90:10:1);
¹H-NMR (DMSO-d₆): δ8.30, 7.51, 7.24, 6.96, 5.07, 4.90, 4.11, 4.00, 3.85, 2.18, 2.08, 1.93-1.59.

Example 16-29

2-{(2R,4aR,5S,6R,7aS)-6-Hydroxy-5-[(2,4,5-trichlorophenoxy)methyl]octahydrocyclopenta[b]pyran-2-yl}-1,3-thiazole-4-carboxylic acid (Compound 16-29)

TLC: Rf 0.47 (dichloromethane:methanol:acetic acid=90:10:1);
¹H-NMR (DMSO-d₆): δ8.36, 7.79, 7.46, 5.09, 4.91, 4.25, 4.11, 3.87, 2.25-2.05, 1.94-1.65.

Example 16-30

2-{(2R,4aR,5S,6R,7aS)-6-Hydroxy-5-[(2,3,4-trichlorophenoxy)methyl]octahydrocyclopenta[b]pyran-2-yl}-1,3-thiazole-4-carboxylic acid (Compound 16-30)

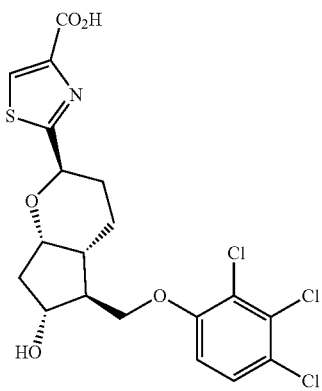 [SMILES: O=C(O)c1csc([C@H]2CC[C@@H]3[C@@H](COc4ccc(Cl)c(Cl)c4Cl)[C@H](O)C[C@@H]3O2)n1]

TLC: Rf 0.45 (dichloromethane:methanol:acetic acid=90:10:1);

$^1$H-NMR (DMSO-$d_6$): δ8.27, 7.60, 7.20, 5.08, 4.25, 4.10, 3.89, 2.29-2.04, 1.86, 1.71.

Example 16-31

2-{(2R,4aR,5S,6R,7aS)-5-[(4-Chloro-3,5-dimethylphenoxy)methyl]-6-hydroxyoctahydrocyclopenta[b]pyran-2-yl}-1,3-thiazole-4-carboxylic acid (Compound 16-31)

TLC: Rf 0.37 (dichloromethane:methanol:acetic acid=90:10:1);

$^1$H-NMR (DMSO-$d_6$): δ8.14, 6.79, 5.05, 4.85, 4.12, 4.04, 3.91, 3.84, 2.29, 2.22-2.05, 1.91-1.60.

Example 16-32

2-{(2R,4aR,5S,6R,7aS)-6-Hydroxy-5-[(3,4,5-trimethylphenoxy)methyl]octahydrocyclopenta[b]pyran-2-yl}-1,3-thiazole-4-carboxylic acid (Compound 16-32)

TLC: Rf 0.49 (dichloromethane:methanol:acetic acid=90:10:1);

$^1$H-NMR (DMSO-$d_6$): δ8.12, 6.58, 5.04, 4.82, 4.12, 4.00, 3.85, 2.24-2.02, 2.18, 2.01, 1.98-1.63.

Example 16-33

2-{(2R,4aR,5S,6R,7aS)-6-Hydroxy-5-[(2-naphthyloxy)methyl]octahydrocyclopenta[b]pyran-2-yl}-1,3-thiazole-4-carboxylic acid (Compound 16-33)

TLC: Rf 0.41 (dichloromethane:methanol:acetic acid=90:10:1);

$^1$H-NMR (DMSO-$d_6$): δ8.39, 7.79, 7.44, 7.34, 7.15, 5.10, 4.94, 4.23-4.06, 3.91, 2.27-2.06, 1.87, 1.78.

Example 16-34

2-{(2R,4aR,5S,6R,7aS)-5-[(1-Benzothiophen-5-yloxy)methyl]-6-hydroxyoctahydrocyclopenta[b]pyran-2-yl}-1,3-thiazole-4-carboxylic acid (Compound 16-34)

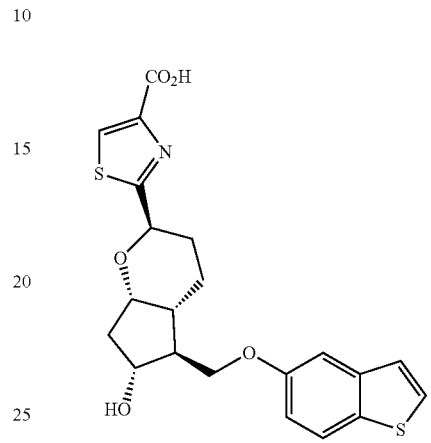

LC-MS/ELSD retention time: 0.86 minute;
MASS (ESI, Pos.): 432 (M+H)$^+$;
$^1$H-NMR (CDCl$_3$): δ8.31, 7.72, 7.43, 7.26, 7.23, 6.94, 5.22, 4.24, 4.14, 4.02, 2.50, 2.28, 2.19, 2.11-1.97, 1.92, 1.76.

Example 16-35

2-{(2R,4aR,5S,6R,7aS)-5-[(1-Benzofuran-5-yloxy)methyl]-6-hydroxyoctahydrocyclopenta[b]pyran-2-yl}-1,3-thiazole-4-carboxylic acid (Compound 16-35)

TLC: Rf 0.42 (chloroform:methanol:acetic acid=9:1:0.1);
$^1$H-NMR (CDCl$_3$): δ8.31, 7.59, 7.38, 7.05, 6.87, 6.69, 5.22, 4.22, 4.12, 3.99, 2.42, 2.36-1.99, 1.90, 1.78.

Example 16-36

2-{(2R,4aR,5S,6R,7aS)-5-[(1,3-Benzothiazole-5-yloxy)methyl]-6-hydroxyoctahydrocyclopenta[b]pyran-2-yl}-1,3-thiazole-4-carboxylic acid (Compound 16-36)

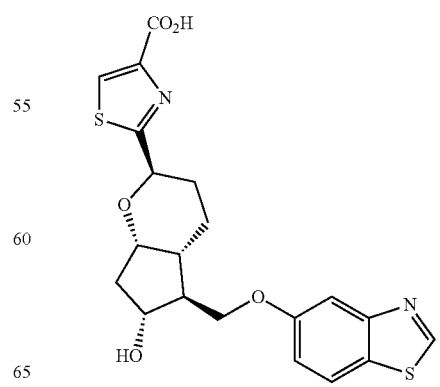

TLC: Rf 0.41 (chloroform:methanol:acetic acid=9:1:0.1);

$^1$H-NMR (DMSO-$d_6$): δ13.0, 9.33, 8.42, 8.00, 7.62, 7.11, 5.09, 4.93, 4.16, 4.07, 3.94, 2.26-2.16, 1.94-1.69.

Example 16-37

2-{(2R,4aR,5S,6R,7aS)-5-[(2,3-Dihydro-1-benzofuran-5-yloxy)methyl]-6-hydroxyoctahydrocyclopenta[b]pyran-2-yl}-1,3-thiazole-4-carboxylic acid (Compound 16-37)

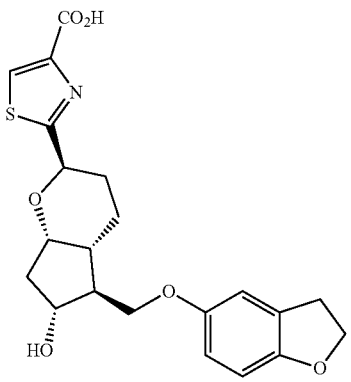 [SMILES: O=C(O)c1csc([C@H]2CC[C@@H]3[C@@H](COc4ccc5c(c4)CCO5)[C@H](O)C[C@@H]3O2)n1]

TLC: Rf 0.44 (dichloromethane:methanol=10:1, COOH Silica);

$^1$H-NMR (CDCl$_3$): δ8.31, 6.78, 6.70-6.61, 5.21, 4.59, 4.20, 4.01, 3.88, 3.18, 2.42, 2.32-2.21, 2.17, 2.06, 1.99, 1.87, 1.72.

Example 16-38

2-{(2R,4aR,5S,6R,7aS)-6-Hydroxy-5-[(3-methoxyphenoxy)methyl]octahydrocyclopenta[b]pyran-2-yl}-1,3-thiazole-4-carboxylic acid (Compound 16-38)

LC-MS/ELSD retention time: 0.78 minute;
MASS (ESI, Pos.): 406 (M+H)$^+$;
$^1$H-NMR (DMSO-$d_6$): δ8.41, 7.15, 6.52-5.45, 5.08, 4.88, 4.15-4.03, 3.96-3.84, 3.71, 2.26-2.05, 1.89-1.60.

Reference Example 29: Propan-2-yl

2-[(2R,4aR,5S,6R,7aS)-5-({[tert-butyl(diphenyl)silyl]oxy}methyl)-6-methoxyoctahydrocyclopenta[b]pyran-2-yl]-1,3-thiazole-4-carboxylate (Reference Compound 29)

Acetonitrile (60 mL), methyl iodide (4.04 mL) and silver oxide (15 g) were added to Reference Compound 22 (3.76 g), and the resultant solution was stirred at room temperature for 48 hours under light-blocking conditions. The reaction solution was filtered through Celite, and a filtrate was concentrated under a reduced pressure. A residue was purified by silica gel column chromatography (hexane:ethyl acetate=9:1→1:1) to produce the title compound (474 mg) having the following physical property value.
TLC: Rf 0.85 (hexane:ethyl acetate=1:1).

Example 17

2-{(2R,4aR,5S,6R,7aS)-5-[(2,3-Dihydro-1H-inden-5-yloxy)methyl]-6-methoxyoctahydrocyclopenta[b]pyran-2-yl}-1,3-thiazole-4-carboxylic acid (Compound 17)

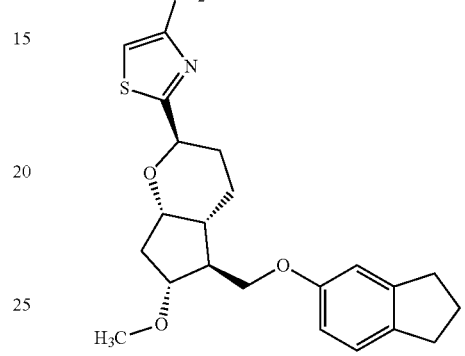

The same procedures as in Reference Example 9→Reference Example 15→Example 1 were carried out, except that Reference Compound 29 was used and 5-indanol was used in place of 3-fluorophenol, thereby producing a compound of the present invention having the following physical property values.
TLC: Rf 0.50 (chloroform:methanol:acetic acid=9:1:0.1);
$^1$H-NMR (CDCl$_3$): δ8.27, 7.10, 6.78, 6.67, 5.15, 4.29, 3.98, 3.78, 3.37, 2.84, 2.39, 2.32-2.18, 2.16-1.92, 1.78.

Reference Example 30: Propan-2-yl

2-{(2R,4aR,5S,6R,7aS)-5-({[tert-butyl(diphenyl)silyl]oxy}methyl)-6-[(4-methylbenzene-1-sulfonyl)oxy]octahydrocyclopenta[b]pyran-2-yl}-1,3-thiazole-4-carboxylate Reference Compound 30

Pyridine (1.5 mL) and para-toluenesulfonyl chloride (165 mg) were added to Reference Compound 22 (387 mg), and the resultant solution was stirred at 50° C. for 12 hours. A 1.0 M aqueous hydrochloric acid solution was added to the reaction solution, and the resultant solution was extracted with ethyl acetate. An organic layer was washed with water and saturated saline, was then dried over anhydrous sodium sulfate, and was then concentrated under a reduced pressure to produce the title compound (472 mg) having the following physical property value.
TLC: Rf 0.77 (hexane:ethyl acetate=1:1).

Reference Example 31: Propan-2-yl

2-[(2R,4aR,5S,7aS)-5-({[tert-butyl(diphenyl)silyl]oxy}methyl)octahydrocyclopenta[b]pyran-2-yl]-1,3-thiazole-4-carboxylate (Reference Compound 31)

Dimethoxyethane (6.0 mL) and water (0.4 mL) were added to Reference Compound 30 (472 mg), and the resultant solution was stirred at room temperature. Sodium iodide (399 mg) and zinc (350 mg) were added to the reaction solution, and the resultant solution was stirred at 90° C. for 6 hours. The reaction solution was filtered through Celite using ethyl acetate. A filtrate was washed with water and saturated saline, was then dried over anhydrous sodium sulfate, and was then concentrated under a reduced pressure. A residue was purified by silica gel column chromatography (hexane:ethyl acetate=9:1→2:2) to produce the title compound (234 mg) having the following physical property value.

TLC: Rf 0.86 (hexane:ethyl acetate=2:1).

Examples 18-1 to 18-2

The same procedures as in Reference Example 9→Reference Example 15→Example 1 were carried out, except that Reference Compound 31 was used and a corresponding phenol compound was used in place of 3-fluorophenol. In this manner, compounds of the present invention having the following physical property values were produced.

Example 18-1

2-{(2R,4aR,5S,7aS)-5-[(2,3-Dihydro-1H-inden-5-yloxy)methyl]octahydrocyclopenta[b]pyran-2-yl}-1,3-thiazole-4-carboxylic acid (Compound 18-1)

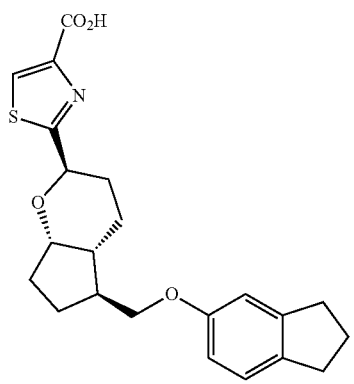 [SMILES: O=C(O)c1csc([C@H]2CC[C@@H]3[C@@H](COc4ccc5c(c4)CCC5)CC[C@@H]3O2)n1]

TLC: Rf 0.43 (dichloromethane:methanol=9:1);
$^1$H-NMR (CDCl$_3$): δ8.26, 7.09, 6.79, 6.67, 5.09, 4.28, 3.85, 2.85, 2.38, 2.23, 2.07, 2.01, 1.87, 1.70, 1.51.

Example 18-2

2-[(2R,4aR,5 S,7aS)-5-(Phenoxymethyl)octahydro cyclopenta[b]pyran-2-yl]-1,3-thiazole-4-carboxylic acid (Compound 18-2)

TLC: Rf 0.26 (dichloromethane:methanol=9:1);
$^1$H-NMR (CDCl$_3$): δ8.26, 7.23, 6.93, 6.98, 5.09, 4.28, 3.89, 2.42, 2.23, 2.12, 2.02, 1.91, 1.73.

Example 19

2-{(2R,4aR,5S,7aS)-5-[(2,3-Dihydro-1H-inden-5-yloxy)methyl]-6,6-difluorooctahydrocyclopenta[b]pyran-2-yl}-1,3-thiazole-4-carboxylic acid (Compound 19)

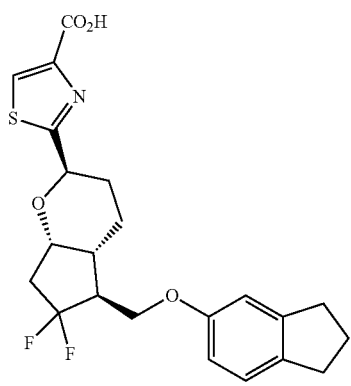 [SMILES: O=C(O)c1csc([C@H]2CC[C@H]3[C@H](CC(F)(F)[C@@H]3COc3ccc4c(c3)CCC4)O2)n1]

The same procedures as in Reference Example 15→Example 1→Example 4→Reference Example 10→Reference Example 17→Example 1 were carried out, except that Reference Compound 9 was used and 5-indanol was used in place of 3-fluorophenol to produce a compound of the present invention having the following physical property values.

TLC: Rf 0.63 (dichloromethane:methanol:water=90:10:1);
$^1$H-NMR (DMSO-d$_6$): δ8.48, 7.08, 6.81, 6.67, 5.22, 4.17, 4.04, 2.94, 2.78, 2.37, 2.14-1.89, 1.77.

Example 20

2-{(2R,4aR,5S,6S,7aS)-5-[(4-Chloro-3-methylphenoxy)methyl]-6-fluorooctahydrocyclopenta[b]pyran-2-yl}-1,3-thiazole-4-carboxylic acid (Compound 20)

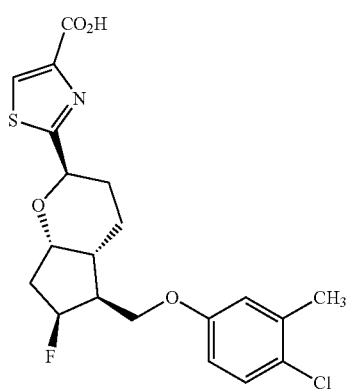 [SMILES: Cc1cc(OC[C@@H]2[C@H]3CC[C@H](c4nc(C(=O)O)cs4)O[C@H]3C[C@@H]2F)ccc1Cl]

The same procedures as in Reference Example 15→Example 1→Example 4 were carried out, except that Reference Compound 9 was used and 4-chloro-3-methyl-phenol was used in place of 3-fluorophenol, thereby producing a compound. N,N-Diethylaminosulfur trifluoride (DAST) (104 mg) was added to a solution of the compound (100 mg) in dichloromethane (3 mL) at −78° C., and the resultant solution was stirred for 30 minutes. A saturated aqueous sodium hydrogen carbonate solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=97:3→7:3) to produce an ester compound (57.4 mg). The same procedure as in Example 1 was carried out using the ester compound to produce a compound of the present invention having the following physical property values.

TLC: Rf 0.48 (chloroform:methanol:acetic acid=90:10:1);
$^1$H-NMR (CDCl$_3$): δ8.30, 7.23, 6.79, 6.70, 5.48-5.22, 5.11, 4.34, 4.18, 3.99, 2.69, 2.49, 2.34, 2.34-2.22, 2.21-2.03, 1.66.

Reference Example 32: Ethyl 4-[(2R,4aR,5S,6R,7aS)-6-(acetyloxy)-5-({[tert-butyl(diphenypsilyl]oxy}methyl)octahydrocyclopenta[b]pyran-2-yl]thiophene-2-carboxylate (Reference Compound 32)

Under an argon stream, 5-ethoxycarbonyl-2-thienylzinc bromide was added to a solution of Reference Compound 5 (490 mg) in acetonitrile (9 mL) at 0° C., and the resultant solution was stirred for 5 minutes. Aluminum chloride (256 mg) was added to the reaction solution, and the resultant solution was stirred at 0° C. for 1 hour. A saturated aqueous potassium sodium L-tartrate solution was added to the reaction solution, and the resultant solution was extracted with ethyl acetate. An organic layer was washed with saturated saline, was then dried over anhydrous sodium sulfate, and was then concentrated under a reduced pressure. A residue was purified by silica gel column chromatography (hexane:ethyl acetate=98:2→85:15) to produce the title compound (517 mg) having the following physical property value.

TLC: Rf 0.63 (hexane:ethyl acetate=7:3).

Example 21

4-{(2R,4aR,5S,6R,7aS)-5-[(4-Chloro-3-methylphenoxy)methyl]-6-hydroxyoctahydrocyclopenta[b]pyran-2-yl}-2-thiophene carboxylic acid (Compound 21)

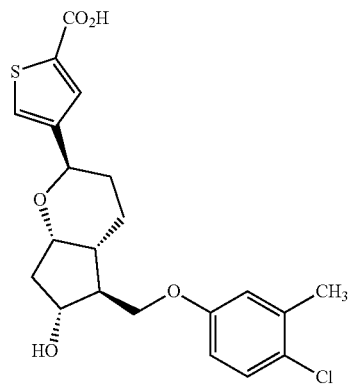 [SMILES: Cc1cc(OC[C@@H]2[C@H]3CC[C@H](c4csc(C(=O)O)c4)O[C@H]3C[C@H]2O)ccc1Cl]

The same procedures as in Reference Example 9→Reference Example 15→Example 1 were carried out, except that Reference Compound 32 was used and 4-chloro-3-methylphenol was used in place of 3-fluorophenol. In this manner, the title compound having the following physical property values was produced.

TLC: Rf 0.39 (dichloromethane:methanol:acetic acid=9:1:0.1);
$^1$H-NMR (CDCl$_3$): δ7.82, 7.46, 7.18, 6.75, 6.64, 5.03, 4.14, 4.06, 3.98, 3.90, 2.45, 2.33, 2.24, 1.98, 1.77.

Example 22

4-{(2R,4aR,5S,6R,7aS)-5-[(4-Chloro-3-methylphenoxy)methyl]-6-hydroxyoctahydrocyclopenta[b]pyran-2-yl}-2-furoic acid (Compound 22)

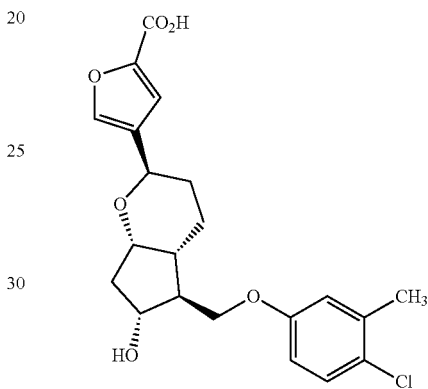

The same procedures as in Reference Example 32→Reference Example 9→Reference Example 15→Example 1 were carried out, except that 5-ethoxycarbonyl-2-furanylzinc bromide was used in place of 5-ethoxycarbonyl-2-thienylzinc bromide and 4-chloro-3-methylphenol was used in place of 3-fluorophenol. In this manner, the title compound having the following physical property values was produced.

TLC: Rf 0.43 (dichloromethane:methanol:acetic acid=9:1:0.1);
$^1$H-NMR (CDCl$_3$): δ7.54, 7.30, 7.20, 6.75, 6.64, 5.01, 4.14, 4.06, 3.99, 3.91, 2.46, 2.33, 2.22, 2.09-1.92, 1.85-1.60.

PHARMACOLOGICAL EXPERIMENTAL EXAMPLE

In Vitro Test
(1) Measurement of Agonist Activity on Various Prostanoid Receptors Using Chem1 cells or CHO cells in which various prostanoid receptors were forcibly expressed, respectively, agonist activities of test compounds on various prostanoid receptors was determined employing, as a measure, an intracellular cyclic AMP (hereinbelow, abbreviated as "cAMP") production amount or an intracellular calcium concentration.

<Compound Treatment>
Each of the test compound and a control substance (PGE$_2$ and PGF$_{2\alpha}$) was dissolved in dimethyl sulfoxide (DMSO) to prepare a 10 mmol/L solution. The 10 mmol/L solution thus prepared was thawed upon use, was then serially diluted with DMSO, and was then diluted with a buffered solution for measurement or a buffered solution for measurement 2, and then the resulting solution was subjected to an experiment.

<Culture of Cells>

Cells, in which various prostanoid receptors were respectively forcibly expressed, were subjected to static culture at 37° C. in the presence of 5% $CO_2$ using a DMEM medium (Sigma) (for culturing FP-Chem1 cells) containing inactivated (56° C., 30 minutes) 9.8 vol % nondialysed-FBS (Life Technologies), 1 vol % Non Essential Amino Acids (Life Technologies), 10 mmol/L HEPES Buffered solution (Life Technologies), 0.5 vol % GENETICIN (Life Technologies) and 1% penicillin-streptomycin (Life Technologies) or an α-MEM medium (Sigma) (for culturing EP2-CHO cells) containing inactivated (56° C., 30 minutes) 9.8 vol % dialysed-FBS (Life Technologies) and penicillin-streptomycin-glutamine (Life Technologies). Subculturing was carried out in the following manner.

The medium was removed from a culture, and the culture was washed with $Ca^{2+}$-free and $Mg^{2+}$-free phosphate-buffered physiological saline one time. A proper amount of trypsin-EDTA (Life Technologies) was added to the washed product, and then the resultant product was incubated at 37° C. The cells were detached, and then a medium in a volume that is 10-fold the volume of trypsin-EDTA was added thereto to terminate the enzymatic reaction. The cells were collected in a centrifuge tube and then centrifuged at room temperature at 120 g for 3 minutes, and the supernatant was discarded therefrom. The cells were suspended in a proper amount of the medium and seeded in a culture flask.

(1-1) Measurement of EP2 Agonist Activity (Measurement of cAMP Concentration)

On the day of measurement, a medium was removed and EP2-CHO cells were washed one time with a phosphate-buffered physiological saline containing 2 mmol/L EDTA and not containing $Ca^{2+}$ and $Mg^{2+}$. A proper amount of the phosphate-buffered physiological saline containing 2 mmol/L EDTA and not containing $Ca^{2+}$ and $Mg^{2+}$ was added to the cells, and this was incubated at 37° C. in the presence of 5% $CO_2$. Subsequently, the cells were detached, then collected in a centrifuge tube and then centrifuged at room temperature at 550 g for 3 minutes, and the supernatant was removed therefrom. The cells were suspended in a proper amount of a buffered solution for measurement 1 (a MEM medium (Invitrogen) containing 1.0 w/v % of bovine serum albumin (Sigma) and 2 µmol/L of diclofenac (Sigma)), and the suspension was centrifuged at room temperature at 200 g for 3 minutes, and the supernatant was removed. The cells were suspended in a buffered solution for measurement 2 (MEM medium (Invitrogen) containing 1.0 w/v % of bovine serum albumin (Sigma), 2 µmol/L of diclofenac (Sigma) and 1 mmol/L of 3-isobutyl-1-methylxanthine), and each 25 µL of the suspension was dispensed into a 96-well ½ area plate so that the number of cells per well became $1.25 \times 10^6$. The buffered solution for measurement 2 (25 µL) containing a compound at each of various concentrations was added to each well to carry out a reaction at room temperature for 30 minutes. Measurement of a cAMP concentration was carried out using cAMP HTRF HiRange kit (CIS bio International). In accordance with the two-step protocol of the kit manual, each 25 µL of cAMP-D2 and Cryptase each diluted with a lysis buffer were added. The reaction solution was incubated at room temperature for 1 hour, and then time resolution fluorescence at each of 620 nm and 660 nm when excited at 340 nm was measured using SpectraMax M5e (Molecular Device). A ratio (TRF ratio) was obtained, and a cAMP concentration was calculated from a calibration line.

(1-2) Measurement of FP Agonist Activity (Measurement of Intracellular Calcium Concentration)

Regarding FP-Chem1, by the same method as that of subculturing, cells were peeled and suspended. Before two days from measurement, the cells were seeded on a 96-well UV plate so that the number of cells per well became $0.5 \times 10^4$, and then standing-cultured at 37° C. in the presence of 5% $CO_2$. On the measurement day, after the medium was removed from each well of the 96-well UV plate, each well was washed with a phosphate-buffered physiological saline not containing $Ca^{2+}$ and $Mg^{2+}$ one time. To each well was added 120 µL of a buffered solution for measurement (Hank's balanced salt solution (Invitrogen) containing 0.1 w/v % of bovine serum albumin, 2.8 µmol/L of diclofenac, 1.25 mmol/L of Probenecid and 20 mmol/L of HEPES (Invitrogen)) containing FLIPR Calcium 5 Assay Kit (Molecular Devices), and this was incubated at room temperature for about 60 minutes under light-shielding conditions, which was subjected to an experiment.

The 96-well UV plate was set in a fluorescent spectral photometer (FDSS-7000EX, Hamamatsu Photonics K.K.), and an intracellular calcium concentration was measured. A buffered solution for measurement (30 µL) containing a compound at each of a variety of concentrations was added to each well to carry out a reaction. An intracellular calcium concentration was determined by irradiating the cells with excited light having a wavelength of 485 nm and measuring a fluorescent intensity at 525 nm.

<Results>

Using the measurement values obtained by the above-mentioned method, an $EC_{50}$ value was calculated as a measure for the agonist activity of a compound of the present invention on a human EP2 receptor.

The results are shown in the following table.

TABLE 1

| Example No. | $EC_{50}$ (nM) |
| --- | --- |
| 2-1 | 1.8 |
| 2-2 | 3.9 |
| 2-4 | 14 |
| 2-9 | 5.8 |
| 2-16 | 1.3 |
| 8 | 0.40 |
| 10 | 0.29 |
| 10-3 | 0.11 |
| 11-2 | 0.10 |
| 13-20 | 5.7 |

As shown below, the compounds according to the present invention exerted potent EP2 agonist activities.

On the other hand, compounds each having an analogous structure to that of the compound according to the present invention, i.e., the following compound which is disclosed in International Publication No. 2011/013651 pamphlet:

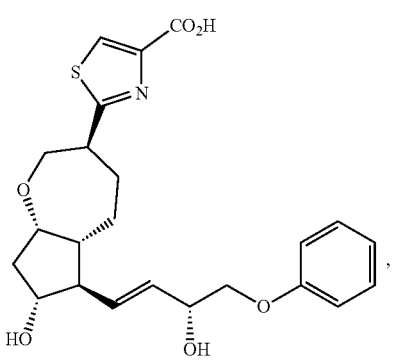 [SMILES: O=C(O)c1csc([C@H]2CC[C@@H]3[C@@H](/C=C/[C@@H](O)COc4ccccc4)[C@H](O)C[C@@H]3OC2)n1]

the following compound which is disclosed in Japanese Patent Laying-Open No. 61-218588:

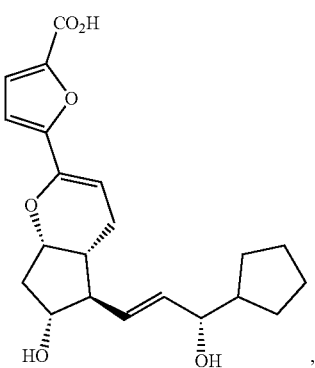 [SMILES: O=C(O)c1ccc(C2=CC[C@@H]3[C@@H](/C=C/[C@@H](O)C4CCCC4)[C@H](O)C[C@@H]3O2)o1]

and the following compounds which is disclosed in Japanese Patent Laying-Open No. 55-89261:

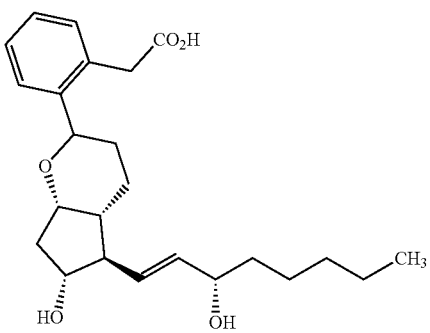

were also determined on their EP2 agonist activities. All of the compounds had $EC_{50}$ values of 10 μM or more which were extremely poor compared with those of the compounds of the present application.

In Vivo Test

As can be easily understood by a person skilled in the art, in an in vivo test, since regarding all test compounds, carboxylic acid which is an active body has poor corneal permeability, pharmacological action of the active body was evaluated by ocular instillation administration of a compound which had been converted into an ester such as an ethyl ester or an isopropyl ester, or an alcohol.

(2) Intraocular Pressure Lowering Activity

A test compound-containing solution (30 μL) which had been adjusted to each of various concentrations was ocular instillation-administered to the left or right eye of a male rabbit (NZW (Healthy)) under consciousness, and an intraocular pressure was measured before the administration and 8 hours after the administration. An intraocular pressure before the administration was measured on a day before the administration. In measurement of an intraocular pressure, the rabbit was fixed on a wood-made restrainer, and the rabbit was anesthetized by the ocular instillation-administration of an ocular surface anesthetic agent (Benoxil eye drops 0.4%, Santen Pharmaceutical Co., Ltd.). After fitting a blepharostat (Handaya Co., Ltd.) to the rabbit, intraocular pressures of both eyes were measured (6 cases per group) with a pneumatic applanation flat tonometer (Model 30 Classic, REICHERT). A difference between an intraocular pressure value before the administration of a test compound and an intraocular pressure value after the administration of the test compound was calculated as an intraocular pressure lowering rate in accordance with the equation shown below, and the sustainability of intraocular eye lowering action was evaluated.

$$\text{Intraocular pressure lowering rate (\%)} = \frac{\begin{array}{c}\text{(intraocular pressure value before}\\ \text{administration of test substance)} -\\ \text{(intraocular pressure value after}\\ \text{administration of test substance)}\end{array}}{\text{intraocular pressure value before administration of test substance}} \times 100 \quad \text{[Equation 1]}$$

<Results>

The results are shown in the following table. The administered concentrations were selected on the basis of the EP2 agonist activities measured by the above-mentioned method.

TABLE 2

| Example No. | Administration concentration (μg/mL) | Intraocular pressure lowering rate (%) |
|---|---|---|
| 4 | 10 | 19.1 |
| 4-3 | 10 | 12.1 |
| 14 | 10 | 23.6 |

As shown above, the compounds according to the present invention exerted potent intraocular pressure lowering actions. Therefore, it was demonstrated that the compounds according to the present invention were effective on ocular diseases which is one type of EP2 receptor-related diseases.

PREPARATION EXAMPLES

Representative preparation examples used in the present invention will be shown below.

1. Injectables

Compound 1 (200 g), mannitol (20 g) and distilled water (50 L) are mixed by an ordinary method, the resulting solution is sterilized by an ordinary method and then filled in ampules at a volume of 5 mL per ampule. The ampules are lyophilized by an ordinary method. In this manner, 10,000 ampules each containing 20 mg of an active ingredient are produced.

2. Tablets

Compound 4 (50 g), calcium carboxymethyl cellulose (20 g), magnesium stearate (10 g) and crystalline cellulose (920 g) are mixed by an ordinary method, and the resulting mixture is tableted. In this manner, 10,000 tablets each containing 5 mg of an active ingredient are produced.

3. Eye Drops

Glycerin (2.5 g) and Polysorbate 80 (500 mg) are added to sterile purified water, compound 3 (1 mg) is then added and dissolved therein, sterile purified water is then added to a total amount of 100 mL, and this is sterile-filtered through a membrane filter and filled into a predetermined container. In this manner, an eye drop is produced.

INDUSTRIAL APPLICABILITY

The compound according to the present invention has an EP2 agonist activity and is highly safe, and is therefore useful as a therapeutic agent for diseases associated with EP2 receptors, such as immune diseases, allergic diseases, neuronal death, dysmenorrhea, premature birth, miscarriage, baldness, ocular diseases, erectile dysfunction, arthritis, lung injury, pulmonary fibrosis, pulmonary emphysema, bronchitis, chronic obstructive pulmonary disease, liver injury, acute hepatitis, cirrhosis, shock, nephritis, renal failure, cardiovascular diseases, systemic inflammatory response syndrome, sepsis, hemophagocytic syndrome, macrophage activation syndrome, Still's disease, Kawasaki disease, burn injury, systemic granuromatous disease, colitis ulcerosa, Crohn's disease, hypercytokinemia on dialysis, multiple organ failure, bone diseases and cartilage injury.

The invention claimed is:
1. A compound of formula (I):

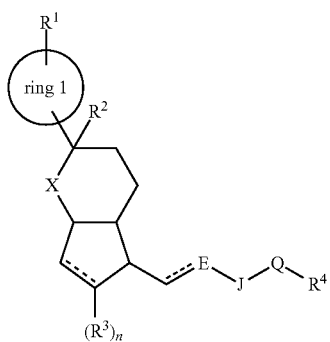

(I)

wherein
ring 1 is a 5-membered monocyclic aromatic ring;
$R^1$ is —$(CH_2)_p$—COOH, —$(CH_2)_q$—COOR$^{11}$, —$(CH_2)_r$—OH, —$(CH_2)_s$—OR$^{12}$, —$CH_2NR^{13}R^{14}$ or —CONR$^{13}R^{14}$;
p is an integer of 0 to 4;
q is an integer of 0 to 4;
r is an integer of 1 to 4;
s is an integer of 1 to 4;
$R^{11}$ is a C1-4 alkyl group;
$R^{12}$ is a C1-4 alkyl group or a C1-4 acyl group;
$R^{13}$ is a hydrogen atom or a C1-4 alkyl group and $R^{14}$ is a hydrogen atom, a C1-4 alkyl group, a C1-4 acyl group, or a $R^{15}O(C=O)$—C1-4 alkylene group, or $R^{13}$, $R^{14}$ and a nitrogen atom to which $R^{13}$ and $R^{14}$ are bound together to form a saturated 5- to 8-membered cyclic amine group;
$R^{15}$ is a hydrogen atom or a C1-4 alkyl group;
X is —O—;
$R^{16}$ is a hydrogen atom, a C1-4 alkyl group, or a C1-4 acyl group;
$R^2$ is a hydrogen atom, or a C1-4 alkyl group;
$R^3$ is a hydrogen atom, a halogen atom, or —OR$^{31}$;
$R^{31}$ is a hydrogen atom, a C1-4 alkyl group, or a C1-4 acyl group;
n is an integer of 1 or 2;
$R^3$'s may be the same as or different from each other when n is 2;
E is —O—, —S—, —SO—, —SO$_2$—, —CH$_2$—, =CH—, or —NR$^{17}$—;
$R^{17}$ is a hydrogen atom, a C1-4 alkyl group, or a C1-4 acyl group;
J is —$(CR^7R^8)_m$—;
m is an integer of 0 to 4;
$R^7$ and $R^8$ independently are a hydrogen atom, a halogen atom, a hydroxy group or a C1-4 alkyl group which may be substituted by a halogen atom, wherein two or more $R^7$'s and $R^8$'s may be the same as or different from each other, or $R^7$ and $R^8$ on the same carbon atom and the carbon atom to which $R^7$ and $R^8$ are bound may together form a C3-6 saturated carbon ring;
Q is a bond, —CH$_2$—, —O—, —O—CH$_2$—, —S—, —SO—, —SO$_2$—, or —NR$^{18}$—;
with proviso that at least one of R3's is a halogen atom when Q is a bond and m is 0;
$R^{18}$ is a hydrogen atom, a C1-4 alkyl group, or a C1-4 acyl group;
$R^4$ is a C1-4 alkyl group, a C2-4 alkenyl group, a C2-4 alkynyl group, or a 3- to 15-membered ring, wherein the 3- to 15-membered ring may be substituted by 0 to 5 $R^5$'s;
$R^5$ is (1) a C1-8 alkyl group, (2) a C2-8 alkenyl group, (3) a C2-8 alkynyl group, (4) a C3-8 cycloalkyl group, (5) a C1-8 alkoxy group, (6) a C3-8 cycloalkyloxy group, (7) a C1-8 acyl group, (8) a C1-8 acyloxy group, (9) a C1-8 alkylthio group, (10) a C3-8 cycloalkylthio group, (11) a C1-8 alkylsulfinyl group, (12) a C3-8 cycloalkylsulfinyl group, (13) a C1-8 alkylsulfonyl group, (14) a C3-8 cycloalkylsulfonyl group, (15) a C1-8 alkoxycarbonyl group, (16) a 5- or 6-membered cyclic group, (17) a (5- or 6-membered cyclic group)-C1-4 alkyl group, (18) a (5- or 6-membered cyclic group)-C1-4 alkoxy group, (19) a (5- or 6-membered cyclic group)-C1-4 acyl group, (20) a halogen atom, (21) a hydroxy group, (22) a nitro group, (23) a cyano group, (24) —NR$^{51}R^{52}$, (25) —CONR$^{53}R^{54}$, or (26) —SO$_2NR^{55}R^{56}$;
$R^{51}$, $R^{52}$, $R^{53}$, $R^{54}$, $R^{55}$ and $R^{56}$ independently are a hydrogen atom, a C1-8 alkyl group, a C1-8 acyl group, or a C1-8 alkylsulfonyl group;
$R^5$'s may be the same as or different from each other when the 3- to 15-membered ring is substituted by multiple $R^5$'s, wherein each of the groups (1) to (19) for $R^5$ may be substituted by 1 to 3 $R^6$'s;
$R^6$ is a C1-4 alkyl group, a C1-4 alkoxy group, a C1-4 acyl group, a C3-8 cycloalkyl group, OH, —NR$^{61}R^{62}$, or a halogen atom, wherein $R^6$'s may be the same as or different from each other when each of the groups (1) to (19) is substituted by multiple $R^6$'s;
$R^{61}$ and $R^{62}$ independently are a hydrogen atom or a C1-4 alkyl group; and
the following bond

===== independently is a single bond or a double bond, or a salt or N-oxide thereof.

2. The compound according to claim 1, or a salt or N-oxide thereof, wherein Q is —CH$_2$—, —O—, —O—CH$_2$—, —S—, —SO—, —SO$_2$— or —NR$^{18}$—.

3. The compound according to claim 1, or a salt or N-oxide thereof, wherein Q is a bond and at least one of R$^3$'s is a halogen atom.

4. The compound according to claim 1, or a salt or N-oxide thereof, wherein E is —CH$_2$— or =CH—.

5. The compound according to claim 1, or a salt or N-oxide thereof, wherein X is —O—.

6. A compound of formula (I-1):

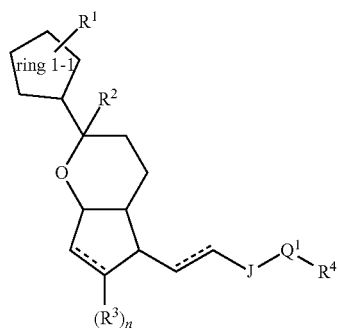

(I-1)

wherein ring 1-1 is a 5-membered monocyclic aromatic heterocyclic ring; Q$^1$ is —CH$_2$—, —O—, —O—CH$_2$—, —S—, —SO—, —SO$_2$—, or —NR$^{18}$—; and other symbols are as defined in claim L, or a salt or N-oxide thereof.

7. The compound according to claim 6, or a salt or N-oxide thereof, wherein ring 1-1 is an oxazole ring, a thiazole ring, a furan ring, or a thiophene ring.

8. The compound according to claim 1, or a salt or N-oxide thereof, wherein the compound is selected from:

(1) 2-{(2R,4aR,5R,6R,7aS)-5-[(1E)-3-(3-fluorophenoxy)-1-propen-1-yl]-6-hydroxyoctahydrocyclopenta[b]pyran-2-yl}-1,3-thiazole-4-carboxylic acid;

(2) 2-{(2R,4aR,5R,6R,7aS)-6-hydroxy-5-[(1E)-5-(4-methoxyphenoxy)-1-penten-1-yl]octahydrocyclopenta[b]pyran-2-yl}-1,3-thiazole-4-carboxylic acid;

(3) 2-{(2R,4aR,5R,6R,7aS)-6-hydroxy-5-[(1E)-4-phenoxy-1-buten-1-yl]octahydrocyclopenta[b]pyran-2-yl}-1,3-thiazole-4-carboxylic acid;

(4) 2-{(2R,4aR,5R,6R,7aS)-6-hydroxy-5-[(1E)-3-phenoxy-1-propen-1-yl]octahydrocyclopenta[b]pyran-2-yl}-1,3-thiazole-4-carboxylic acid;

(5) 2-{(2R,4aR,5R,6R,7aS)-6-hydroxy-5-[(1E)-5-phenoxy-1-penten-1-yl]octahydrocyclopenta[b]pyran-2-yl}-1,3-thiazole-4-carboxylic acid;

(6) 2-{(2R,4aR,5R,6R,7aS)-5-[(1E)-3-(2-fluorophenoxy)-1-propen-1-yl]-6-hydroxyoctahydrocyclopenta[b]pyran-2-yl}-1,3-thiazole-4-carboxylic acid;

(7) 2-{(2R,4aR,5R,6R,7aS)-5-[(1E)-3-(4-fluorophenoxy)-1-propen-1-yl]-6-hydroxyoctahydrocyclopenta[b]pyran-2-yl}-1,3-thiazole-4-carboxylic acid;

(8) 2-{(2R,4aR,5R,6R,7aS)-6-hydroxy-5-[(1E)-3-(2-methylphenoxy)-1-propen-1-yl]octahydrocyclopenta[b]pyran-2-yl}-1,3-thiazole-4-carboxylic acid;

(9) 2-{(2R,4aR,5R,6R,7aS)-6-hydroxy-5-[(1E)-3-(3-methylphenoxy)-1-propen-1-yl]octahydrocyclopenta[b]pyran-2-yl}-1,3-thiazole-4-carboxylic acid;

(10) 2-{(2R,4aR,5R,6R,7aS)-6-hydroxy-5-[(1E)-3-(4-methylphenoxy)-1-propen-1-yl]octahydrocyclopenta[b]pyran-2-yl}-1,3-thiazole-4-carboxylic acid;

(11) 2-{(2R,4aR,5R,6R,7aS)-5-[(1E)-3-(2-chlorophenoxy)-1-propen-1-yl]-6-hydroxyoctahydrocyclopenta[b]pyran-2-yl}-1,3-thiazole-4-carboxylic acid;

(12) 2-{(2R,4aR,5R,6R,7aS)-5-[(1E)-3-(3-chlorophenoxy)-1-propen-1-yl]-6-hydroxyoctahydrocyclopenta[b]pyran-2-yl}-1,3-thiazole-4-carboxylic acid;

(13) 2-{(2R,4aR,5R,6R,7aS)-5-[(1E)-3-(4-chlorophenoxy)-1-propen-1-yl]-6-hydroxyoctahydrocyclopenta[b]pyran-2-yl}-1,3-thiazole-4-carboxylic acid;

(14) 2-[(2R,4aR,5R,6R,7aS)-6-hydroxy-5-{(1E)-3-[2-(trifluoromethoxy)phenoxy]-1-propen-1-yl}octahydrocyclopenta[b]pyran-2-yl]-1,3-thiazole-4-carboxylic acid;

(15) 2-[(2R,4aR,5R,6R,7aS)-6-hydroxy-5-{(1E)-3-[3-(trifluoromethoxy)phenoxy]-1-propen-1-yl}octahydrocyclopenta[b]pyran-2-yl]-1,3-thiazole-4-carboxylic acid;

(16) 2-[(2R,4aR,5R,6R,7aS)-6-hydroxy-5-{(1E)-3-[4-(trifluoromethoxy)phenoxy]-1-propen-1-yl}octahydrocyclopenta[b]pyran-2-yl]-1,3-thiazole-4-carboxylic acid;

(17) 2-[(2R,4aR,5R,6R,7aS)-6-hydroxy-5-{(1E)-3-[2-(trifluoromethyl)phenoxy]-1-propen-1-yl}octahydrocyclopenta[b]pyran-2-yl]-1,3-thiazole-4-carboxylic acid;

(18) 2-[(2R,4aR,5R,6R,7aS)-6-hydroxy-5-{(1E)-3-[3-(trifluoromethyl)phenoxy]-1-propen-1-yl}octahydrocyclopenta[b]pyran-2-yl]-1,3-thiazole-4-carboxylic acid;

(19) 2-[(2R,4aR,5R,6R,7aS)-6-hydroxy-5-{(1E)-3-[4-(trifluoromethyl)phenoxy]-1-propen-1-yl}octahydrocyclopenta[b]pyran-2-yl]-1,3-thiazole-4-carboxylic acid;

(20) 2-{(2R,4aR,5R,6R,7aS)-6-hydroxy-5-[(1E)-3-(2-methoxyphenoxy)-1-propen-1-yl]octahydrocyclopenta[b]pyran-2-yl}-1,3-thiazole-4-carboxylic acid;

(21) 2-{(2R,4aR,5R,6R,7aS)-6-hydroxy-5-[(1E)-3-(3-methoxyphenoxy)-1-propen-1-yl]octahydrocyclopenta[b]pyran-2-yl}-1,3-thiazole-4-carboxylic acid;

(22) 2-{(2R,4aR,5R,6R,7aS)-6-hydroxy-5-[(1E)-3-(4-methoxyphenoxy)-1-propen-1-yl]octahydrocyclopenta[b]pyran-2-yl}-1,3-thiazole-4-carboxylic acid;

(23) 2-[(2R,4aR,5R,6R,7aS)-6-hydroxy-5-{(1E)-5-[4-(trifluoromethoxy)phenoxy]-1-penten-1-yl}octahydrocyclopenta[b]pyran-2-yl]-1,3-thiazole-4-carboxylic acid;

(24) 2-{(2R,4aR,5R,6R,7aS)-5-[(1E)-5-(4-chloro-3-fluorophenoxy)-1-penten-1-yl]-6-hydroxyoctahydrocyclopenta[b]pyran-2-yl}-1,3-thiazole-4-carboxylic acid;

(25) (2R,4aR,5R,6R,7aS)-2-[4-(hydroxymethyl)-1,3-thiazol-2-yl]-5-[(1E)-5-(4-methoxyphenoxy)-1-penten-1-yl]octahydrocyclopenta[b]pyran-6-ol;

(26) isopropyl 2-{(2R,4aR,5R,6R,7aS)-6-hydroxy-5-[(1E)-5-(4-methoxyphenoxy)-1-penten-1-yl]octahydrocyclopenta[b]pyran-2-yl}-1,3-thiazole-4-carboxylate;

(27) isopropyl 2-{(2R,4aR,5R,6R,7aS)-6-hydroxy-5-[(1E)-4-phenoxy-1-buten-1-yl]octahydrocyclopenta[b]pyran-2-yl}-1,3-thiazole-4-carboxylate;

(28) isopropyl 2-[(2R,4aR,5R,6R,7aS)-6-hydroxy-5-{(1E)-3-[2-(trifluoromethyl)phenoxy]-1-propen-1-yl}octahydrocyclopenta[b]pyran-2-yl]-1,3-thiazole-4-carboxylate;

(29) 2-{(2R,4aR,5R,6R,7aS)-5-[(1E)-3-(benzyloxy)-1-propen-1-yl]-6-hydroxyoctahydrocyclopenta[b]pyran-2-yl}-1,3-thiazole-4-carboxylic acid;

(30) 2-{(2R,4aR,5R,6R,7aS)-5-[3-(benzyloxy)propyl]-6-hydroxyoctahydrocyclopenta[b]pyran-2-yl}-1,3-thiazole-4-carboxylic acid;
(31) 2-[(2R,4aR,5R,6R,7aS)-6-hydroxy-5-(3-phenoxypropyl)octahydrocyclopenta[b]pyran-2-yl]-1,3-thiazole-4-carboxylic acid;
(32) 2-[(2R,4aR,5R,6R,7aS)-6-hydroxy-5-(5-phenoxypentyl)octahydrocyclopenta[b]pyran-2-yl]-1,3-thiazole-4-carboxylic acid;
(33) 2-[(2R,4aR,5R,6R,7aS)-6-hydroxy-5-(4-phenoxybutyl)octahydrocyclopenta[b]pyran-2-yl]-1,3-thiazole-4-carboxylic acid;
(34) 2-{(2R,4aR,5R,6R,7aS)-5-[(1E)-3,3-difluoro-1-octen-1-yl]-6-hydroxyoctahydrocyclopenta[b]pyran-2-yl}-1,3-thiazole-4-carboxylic acid;
(35) 2-{(2R,4aR,5R,6R,7aS)-5-[(1E)-4,4-difluoro-3-hydroxy-1-octen-1-yl]-6-hydroxyoctahydrocyclopenta[b]pyran-2-yl}-1,3-thiazole-4-carboxylic acid;
(36) 2-{(2R,4aR,5R,6R,7aS)-5-[(1E)-5-(4-cyanophenyl)-3-hydroxy-1-penten-1-yl]-6-hydroxyoctahydrocyclopenta[b]pyran-2-yl}-1,3-thiazole-4-carboxylic acid;
(37) 2-{(2R,4aR,5R,6R,7aS)-6-hydroxy-5-[(1E)-3-hydroxy-1-octen-1-yl]octahydrocyclopenta[b]pyran-2-yl}-1,3-thiazole-4-carboxylic acid;
(38) 2-{(2R,4aR,5R,6R,7aS)-5-[(1E)-5-cyclopentyl-3-hydroxy-1-penten-1-yl]-6-hydroxyoctahydrocyclopenta[b]pyran-2-yl}-1,3-thiazole-4-carboxylic acid;
(39) 2-{(2R,4aR,5R,6R,7aS)-6-hydroxy-5-[(1E)-3-hydroxy-5-(2-naphthyl)-1-penten-1-yl]octahydrocyclopenta[b]pyran-2-yl}-1,3-thiazole-4-carboxylic acid;
(40) 2-{(2R,4aR,5R,6R,7aS)-6-hydroxy-5-[(1E)-3-hydroxy-1-decen-1-yl]octahydrocyclopenta[b]pyran-2-yl}-1,3-thiazole-4-carboxylic acid;
(41) 2-{(2R,4aR,5R,6R,7aS)-6-hydroxy-5-[(1E)-3-hydroxy-4-phenyl-1-buten-1-yl]octahydrocyclopenta[b]pyran-2-yl}-1,3-thiazole-4-carboxylic acid;
(42) 2-{(2R,4aR,5R,6R,7aS)-6-hydroxy-5-[(1E)-4-hydroxy-1-octen-1-yl]octahydrocyclopenta[b]pyran-2-yl}-1,3-thiazole-4-carboxylic acid;
(43) 2-{(2R,4aR,5R,6R,7aS)-5-[(1E,4S)-4-(1-ethylcyclobutyl)-4-hydroxy-1-buten-1-yl]-6-hydroxyoctahydrocyclopenta[b]pyran-2-yl}-1,3-thiazole-4-carboxylic acid;
(44) 2-{(2R,4aR,5R,6R,7aS)-6-hydroxy-5-[(1E,3S)-3-hydroxy-1-octen-1-yl]octahydrocyclopenta[b]pyran-2-yl}-1,3-thiazole-4-carboxylic acid;
(45) 2-[(2R,4aR,5R,6R,7aS)-6-hydroxy-5-(2-phenoxyethyl)octahydrocyclopenta[b]pyran-2-yl]-1,3-thiazole-4-carboxylic acid;
(46) 2-{(2R,4aR,5R,6R,7aS)-6-hydroxy-5-[2-(3-methylphenoxy)ethyl]octahydrocyclopenta[b]pyran-2-yl}-1,3-thiazole-4-carboxylic acid;
(47) 2-{(2R,4aR,5R,6R,7aS)-6-hydroxy-5-[2-(2-methylphenoxy)ethyl]octahydrocyclopenta[b]pyran-2-yl}-1,3-thiazole-4-carboxylic acid;
(48) 2-{(2R,4aR,5R,6R,7aS)-6-hydroxy-5-[2-(4-methylphenoxy)ethyl]octahydrocyclopenta[b]pyran-2-yl}-1,3-thiazole-4-carboxylic acid;
(49) 2-{(2R,4aR,5R,6R,7aS)-5-[2-(2-fluorophenoxy)ethyl]-6-hydroxyoctahydrocyclopenta[b]pyran-2-yl}-1,3-thiazole-4-carboxylic acid;
(50) 2-{(2R,4aR,5R,6R,7aS)-5-[2-(3-fluorophenoxy)ethyl]-6-hydroxyoctahydrocyclopenta[b]pyran-2-yl}-1,3-thiazole-4-carboxylic acid;
(51) 2-{(2R,4aR,5R,6R,7aS)-5-[2-(4-fluorophenoxy)ethyl]-6-hydroxyoctahydrocyclopenta[b]pyran-2-yl}-1,3-thiazole-4-carboxylic acid;
(52) 2-{(2R,4aR,5R,6R,7aS)-5-[2-(2-chlorophenoxy)ethyl]-6-hydroxyoctahydrocyclopenta[b]pyran-2-yl}-1,3-thiazole-4-carboxylic acid;
(53) 2-{(2R,4aR,5R,6R,7aS)-5-[2-(3-chlorophenoxy)ethyl]-6-hydroxyoctahydrocyclopenta[b]pyran-2-yl}-1,3-thiazole-4-carboxylic acid;
(54) 2-{(2R,4aR,5R,6R,7aS)-5-[2-(4-chlorophenoxy)ethyl]-6-hydroxyoctahydrocyclopenta[b]pyran-2-yl}-1,3-thiazole-4-carboxylic acid;
(55) 2-[(2R,4aR,5R,6R,7aS)-6-hydroxy-5-{2-[2-(trifluoromethoxy)phenoxy]ethyl}octahydrocyclopenta[b]pyran-2-yl]-1,3-thiazole-4-carboxylic acid;
(56) 2-[(2R,4aR,5R,6R,7aS)-6-hydroxy-5-{2-[3-(trifluoromethoxy)phenoxy]ethyl}octahydrocyclopenta[b]pyran-2-yl]-1,3-thiazole-4-carboxylic acid;
(57) 2-[(2R,4aR,5R,6R,7aS)-6-hydroxy-5-{2-[4-(trifluoromethoxy)phenoxy]ethyl}octahydrocyclopenta[b]pyran-2-yl]-1,3-thiazole-4-carboxylic acid;
(58) 2-[(2R,4aR,5R,6R,7aS)-6-hydroxy-5-{2-[2-(trifluoromethyl)phenoxy]ethyl}octahydrocyclopenta[b]pyran-2-yl]-1,3-thiazole-4-carboxylic acid;
(59) 2-[(2R,4aR,5R,6R,7aS)-6-hydroxy-5-{2-[3-(trifluoromethyl)phenoxy]ethyl}octahydrocyclopenta[b]pyran-2-yl]-1,3-thiazole-4-carboxylic acid;
(60) 2-[(2R,4aR,5R,6R,7aS)-6-hydroxy-5-{2-[4-(trifluoromethyl)phenoxy]ethyl}octahydrocyclopenta[b]pyran-2-yl]-1,3-thiazole-4-carboxylic acid;
(61) 2-{(2R,4aR,5R,6R,7aS)-6-hydroxy-5-[2-(2-methoxyphenoxy)ethyl]octahydrocyclopenta[b]pyran-2-yl}-1,3-thiazole-4-carboxylic acid;
(62) 2-{(2R,4aR,5R,6R,7aS)-6-hydroxy-5-[2-(3-methoxyphenoxy)ethyl]octahydrocyclopenta[b]pyran-2-yl}-1,3-thiazole-4-carboxylic acid;
(63) 2-{(2R,4aR,5R,6R,7aS)-6-hydroxy-5-[2-(4-methoxyphenoxy)ethyl]octahydrocyclopenta[b]pyran-2-yl}-1,3-thiazole-4-carboxylic acid;
(64) 2-{(2R,4aR,5R,6R,7aS)-6-hydroxy-5-[2-(3-methyl-4-nitrophenoxy)ethyl]octahydrocyclopenta[b]pyran-2-yl}-1,3-thiazole-4-carboxylic acid;
(65) 2-{(2R,4aR,5R,6R,7aS)-5-[2-(3,4-dichlorophenoxy)ethyl]-6-hydroxyoctahydrocyclopenta[b]pyran-2-yl}-1,3-thiazole-4-carboxylic acid;
(66) isopropyl 2-{(2R,4aR,5R,6R,7aS)-6-hydroxy-5-[2-(3-methyl-4-nitrophenoxy)ethyl]octahydrocyclopenta[b]pyran-2-yl}-1,3-thiazole-4-carboxylate; and
(67) (2R,4aR,5R,6R,7aS)-5-[2-(3,4-dichlorophenoxy)ethyl]-2-[4-(hydroxymethyl)-1,3-thiazol-2-yl]octahydrocyclopenta[b]pyran-6-ol.

9. The compound according to claim 1, or a salt or N-oxide thereof, wherein the compound is selected from:
(1) 2-{(2R,4aR,5S,7aS)-5-[(2,3-dihydro-1H-inden-5-yloxy)methyl]-6,6-difluorooctahydrocyclopenta[b]pyran-2-yl}-1,3-thiazole-4-carboxylic acid; and
(2) 2-{(2R,4aR,5S,6S,7aS)-5-[(4-chloro-3-methylphenoxy)methyl]-6-fluorooctahydrocyclopenta[b]pyran-2-yl}-1,3-thiazole-4-carboxylic acid.

10. A pharmaceutical composition comprising a compound represented by general formula (I), or a salt or N-oxide thereof, and a pharmaceutically acceptable carrier.

11. A method for treating a disease associated with an EP2 receptor, comprising administering an effective amount of a compound represented by general formula (I), or a salt or N-oxide thereof to a mammal.

* * * * *

UNITED STATES PATENT AND TRADEMARK OFFICE
CERTIFICATE OF CORRECTION

PATENT NO. : 10,385,045 B2
APPLICATION NO. : 15/746617
DATED : August 20, 2019
INVENTOR(S) : Seiji Ogawa et al.

It is certified that error appears in the above-identified patent and that said Letters Patent is hereby corrected as shown below:

In the Claims

In Claim 1, Column 93, Line 58, delete "C1-4" and insert --$C_{1-4}$-- therefor;

In Claim 1, Column 93, Line 59, delete "C1-4" and insert --$C_{1-4}$-- therefor;

In Claim 1, Column 93, Line 59, delete "C1-4" and insert --$C_{1-4}$-- therefor;

In Claim 1, Column 93, Line 60, delete "C1-4" and insert --$C_{1-4}$-- therefor;

In Claim 1, Column 93, Line 61, delete "C1-4" and insert --$C_{1-4}$-- therefor;

In Claim 1, Column 93, Line 61, delete "C1-4" and insert --$C_{1-4}$-- therefor;

In Claim 1, Column 93, Line 62, delete "$R^{15}O(C=O)$-C1-4" and insert --$R^{15}O(C=O)$-$C_{1-4}$-- therefor;

In Claim 1, Column 93, Line 66, delete "C1-4" and insert --$C_{1-4}$-- therefor;

In Claim 1, Column 94, Line 1 (first occurrence), delete "C1-4" and insert --$C_{1-4}$-- therefor;

In Claim 1, Column 94, Line 1 (second occurrence), delete "C1-4" and insert --$C_{1-4}$-- therefor;

In Claim 1, Column 94, Line 3, delete "C1-4" and insert --$C_{1-4}$-- therefor;

In Claim 1, Column 94, Line 5 (first occurrence), delete "C1-4" and insert --$C_{1-4}$-- therefor;

In Claim 1, Column 94, Line 5 (second occurrence), delete "C1-4" and insert --$C_{1-4}$-- therefor;

In Claim 1, Column 94, Line 12 (first occurrence), delete "C1-4" and insert --$C_{1-4}$-- therefor;

Signed and Sealed this
Thirty-first Day of December, 2019

Andrei Iancu
*Director of the United States Patent and Trademark Office*

CERTIFICATE OF CORRECTION (continued)
U.S. Pat. No. 10,385,045 B2

In Claim 1, Column 94, Line 12 (second occurrence), delete "C1-4" and insert --$C_{1-4}$-- therefor;

In Claim 1, Column 94, Line 18, delete "C1-4" and insert --$C_{1-4}$-- therefor;

In Claim 1, Column 94, Line 23, delete "C3-6" and insert --$C_{3-6}$-- therefor;

In Claim 1, Column 94, Line 26, delete "R3's" and insert --$R^3$'s-- therefor;

In Claim 1, Column 94, Line 28 (first occurrence), delete "C1-4" and insert --$C_{1-4}$-- therefor;

In Claim 1, Column 94, Line 28 (second occurrence), delete "C1-4" and insert --$C_{1-4}$-- therefor;

In Claim 1, Column 94, Line 30, delete "C1-4" and insert --$C_{1-4}$-- therefor;

In Claim 1, Column 94, Line 30 (first occurrence), delete "C2-4" and insert --$C_{2-4}$-- therefor;

In Claim 1, Column 94, Line 30 (second occurrence), delete "C2-4" and insert --$C_{2-4}$-- therefor;

In Claim 1, Column 94, Line 34, delete "C1-8" and insert --$C_{1-8}$-- therefor;

In Claim 1, Column 94, Line 34, delete "C2-8" and insert --$C_{2-8}$-- therefor;

In Claim 1, Column 94, Line 35, delete "C2-8" and insert --$C_{2-8}$-- therefor;

In Claim 1, Column 94, Line 35, delete "C3-8" and insert --$C_{3-8}$-- therefor;

In Claim 1, Column 94, Line 36, delete "C1-8" and insert --$C_{1-8}$-- therefor;

In Claim 1, Column 94, Line 36, delete "C3-8" and insert --$C_{3-8}$-- therefor;

In Claim 1, Column 94, Line 37 (first occurrence), delete "C1-8" and insert --$C_{1-8}$-- therefor;

In Claim 1, Column 94, Line 37 (second occurrence), delete "C1-8" and insert --$C_{1-8}$-- therefor;

In Claim 1, Column 94, Line 38, delete "C1-8" and insert --$C_{1-8}$-- therefor;

In Claim 1, Column 94, Line 38, delete "C3-8" and insert --$C_{3-8}$-- therefor;

In Claim 1, Column 94, Line 39, delete "C1-8" and insert --$C_{1-8}$-- therefor;

In Claim 1, Column 94, Line 39, delete "C3-8" and insert --$C_{3-8}$-- therefor;

In Claim 1, Column 94, Line 40, delete "C1-8" and insert --$C_{1-8}$-- therefor;

In Claim 1, Column 94, Line 41, delete "C3-8" and insert --$C_{3-8}$-- therefor;

CERTIFICATE OF CORRECTION (continued)
U.S. Pat. No. 10,385,045 B2

In Claim 1, Column 94, Line 41, delete "C1-8" and insert --$C_{1-8}$-- therefor;

In Claim 1, Column 94, Line 43, delete "group)-C1-4" and insert --group)-$C_{1-4}$-- therefor;

In Claim 1, Column 94, Line 44, delete "group)-C1-4" and insert --group)-$C_{1-4}$-- therefor;

In Claim 1, Column 94, Line 46, delete "C1-4" and insert --$C_{1-4}$-- therefor;

In Claim 1, Column 94, Line 51 (first occurrence), delete "C1-8" and insert --$C_{1-8}$-- therefor;

In Claim 1, Column 94, Line 51 (second occurrence), delete "C1-8" and insert --$C_{1-8}$-- therefor;

In Claim 1, Column 94, Line 52, delete "C1-8" and insert --$C_{1-8}$-- therefor;

In Claim 1, Column 94, Line 57 (first occurrence), delete "C1-4" and insert --$C_{1-4}$-- therefor;

In Claim 1, Column 94, Line 57 (second occurrence), delete "C1-4" and insert --$C_{1-4}$-- therefor;

In Claim 1, Column 94, Line 57 (third occurrence), delete "C1-4" and insert --$C_{1-4}$-- therefor;

In Claim 1, Column 94, Line 58, delete "C3-8" and insert --$C_{3-8}$-- therefor;

In Claim 1, Column 94, Line 62, delete "C1-4" and insert --$C_{1-4}$-- therefor;

In Claim 6, Column 95, Line 30, delete "claim L," and insert --claim 1,-- therefor.